US012571800B2

(12) United States Patent
Lee et al.

(10) Patent No.: US 12,571,800 B2
(45) Date of Patent: Mar. 10, 2026

(54) MEANS AND METHODS FOR TREATING ANGIOGENESIS-RELATED DISEASES

(71) Applicant: Heidelberg Biotech GmbH, Heidelberg (DE)

(72) Inventors: Tong-Young Lee, Taipei City (TW); Amir Abdollahi, Heidelberg (DE); Kashi Javaherian, Lexington, MA (US)

(73) Assignee: Heidelberg Biotech GmbH, Heidelberg (DE)

( * ) Notice: Subject to any disclaimer, the term of this patent is extended or adjusted under 35 U.S.C. 154(b) by 0 days.

(21) Appl. No.: 17/965,967

(22) Filed: Oct. 14, 2022

(65) Prior Publication Data

US 2023/0341406 A1 Oct. 26, 2023

Related U.S. Application Data

(62) Division of application No. 14/240,273, filed as application No. PCT/EP2012/066467 on Jun. 23, 2012, now abandoned.

(60) Provisional application No. 61/526,535, filed on Aug. 23, 2011.

(30) Foreign Application Priority Data

Aug. 23, 2011 (EP) .................................... 11178509

(51) Int. Cl.
| | |
|---|---|
| *C07K 4/00* | (2006.01) |
| *A61K 38/39* | (2006.01) |
| *A61K 47/68* | (2017.01) |
| *C07K 2/00* | (2006.01) |
| *C07K 14/435* | (2006.01) |
| *C07K 14/78* | (2006.01) |
| *G01N 33/574* | (2006.01) |

(52) U.S. Cl.
CPC ....... *G01N 33/57484* (2013.01); *A61K 38/39* (2013.01); *A61K 47/6883* (2017.08); *C07K 14/435* (2013.01); *C07K 14/78* (2013.01); *C07K 2319/00* (2013.01); *C07K 2319/21* (2013.01); *C07K 2319/30* (2013.01); *C07K 2319/50* (2013.01); *G01N 2500/04* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 6,630,448 B2 | 10/2003 | O'Reilly et al. | |
| 6,825,167 B1 | 11/2004 | Yokoyama et al. | |
| 7,524,811 B2 | 4/2009 | Folkman et al. | |
| 11,548,934 B2 * | 1/2023 | Abdollahi | ............... A61P 17/00 |
| 2003/0139365 A1 | 7/2003 | Lo et al. | |
| 2004/0009920 A1 | 1/2004 | Ruoslahti | |
| 2004/0033210 A1 | 2/2004 | Gillies | |
| 2004/0180035 A1 | 9/2004 | Gillies | |
| 2005/0255547 A1 | 11/2005 | Tschopp et al. | |
| 2006/0251699 A1 | 11/2006 | Folkman et al. | |
| 2007/0015242 A1 | 1/2007 | Azar et al. | |
| 2007/0253952 A1 | 11/2007 | Alvarez Vallina et al. | |
| 2008/0269135 A1 | 10/2008 | Retsky | |
| 2010/0305303 A1 | 12/2010 | Xu | |
| 2011/0038865 A1 * | 2/2011 | Shin | ........................ A61P 35/00 |
| | | | 435/328 |
| 2012/0116057 A1 | 5/2012 | Kannan et al. | |
| 2012/0276125 A1 | 11/2012 | Ast | |
| 2013/0164286 A1 | 6/2013 | Chou et al. | |

FOREIGN PATENT DOCUMENTS

| | | |
|---|---|---|
| WO | WO 99/62944 | 12/1999 |
| WO | WO 2006/048252 A1 | 5/2006 |
| WO | WO 2009/003145 A1 | 12/2008 |

OTHER PUBLICATIONS

Yokoyama et al. Genetic modification of human endostatin: RGD-motif potentiates anti-tumor activity. (Proceedings of the American Association for Cancer Research Annual Meeting, (Mar. 2000) No. 41, pp. 488, Abs: #3113). (Year: 2000).*
Aota et al. A 27-Amino-Acid Synthetic Peptide Corresponding to the NH2-Terminal Zinc-Binding Domain of Endostatin Is Responsible for Its Antitumor Activity. JBC, 269(40):24764-24761, 1994. (Year: 1994).*
Benoit et al. The effect on osteoblast function of colocalized RGD and PHSRN epitopes on PEG surfaces. Biomaterials. Sep. 2005; 26(25):5209-20. (Year: 2005).*
Koivunen et al. Phage libraries displaying cyclic peptides with different ring sizes: ligand specificities of the RGD-directed integrins. Biotechnology (N Y) 1995; 13(3):265-70. (Year: 1995).*
Lu X et al . Preferential antagonism of the interactions of the integrin alpha IIb beta 3 with immobilized glycoprotein ligands by snake-venom RGD (Arg-Gly-Asp) proteins. Evidence supporting a functional role for the amino acid residues flanking the tripeptide RGD in . . . (1994) Biochem J 304: 929-936 (Year: 1995).*
Shroff et al. Fibronectin-mimetic peptide-amphiphile nanofiber gels support increased cell adhesion and promote ECM production. Soft Matter, 2010, 6, 5064-5072. (Year: 2010).*
Kolozsi et al. N-terminal fragment of the anti-angiogenic human endostatin binds copper(II)with very high affinity. Journal of Inorganic Biochemistry 103 (2009) 940-947. (Year: 2009).*

(Continued)

*Primary Examiner* — Maher M Haddad

(74) *Attorney, Agent, or Firm* — Foley & Lardner LLP

(57) ABSTRACT

The present invention is concerned with a protein oligomer comprising at least two NC-1 monomers of human collagen 18 or fragments of an NC-1 monomer of human collagen 18 for use in the treatment or prevention of an angiogenesis-related disease. The invention further pertains to a fusion protein comprising a NC-1 monomer of human collagen 18 and a Fc domain of an immunoglobulin. The invention also relates to a fusion protein comprising: a) an endostatin peptide or endostatin-derived peptide and b) the RGD motif and/or PHSRN motif of Fibronectin. The invention further relates to a kit comprising the protein oligomer or fusion proteins of the invention.

4 Claims, 32 Drawing Sheets

Figure 1:
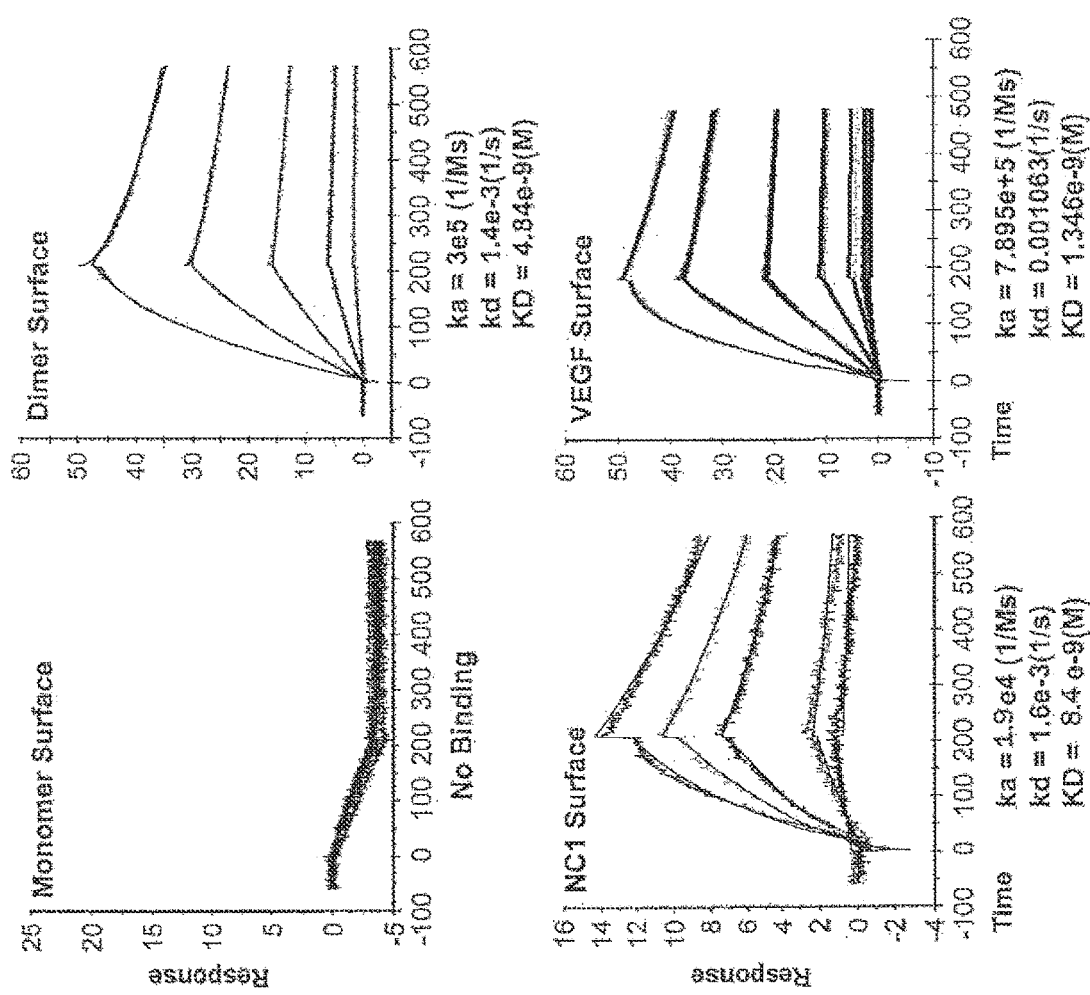

Specification includes a Sequence Listing.

(56)            References Cited

OTHER PUBLICATIONS

European Search Report issued in related European Patent Application No. 11178509, completed Feb. 8, 2012.
Abdollahi et al., "Combined Therapy with Direct and Indirect Angiogenesis Inhibition Results in Enhanced Antiangiogenic and Antitumor Effects," Cancer Res., vol. 63, pp. 8890-8898 (2003).
Abdollahi et al., "Endostatin: The logic of antiangiogenic therapy," Drug Resistance Updates, vol. 8, pp. 59-74 (2005).
Abdollahi et al., "Endostatin's Antiangiogenic Signaling Network," Mol. Cell, vol. 13, pp. 649-663 (2004).
Abe et al., "Identification of a novel collagen chain represented by extensive interruptions in the triple-helical region," Biochem. Biophy. Res. Comm., vol. 196, pp. 576-582 (1993).
Bergers et al., "Effects of Angiogenesis Inhibitors on Multistage Carcinogenesis in Mice," Science, vol. 284, pp. 808-812 (1999).
Boehm et al., "Zinc-Binding of Endostatin Is Essential for Its Antiangiogenic Activity," Biochem. Biophys. Res. Comm., vol. 252, pp. 190-194 (1998).
Capon et al., "Designing CD4 immunoadhesins for AIDS therapy," Nature, vol. 337, pp. 525-531 (1989).
Ding et al., "Zinc-dependent dimers observed in crystals of human endostatin," Proc. Natl. Acad. Sci. USA, vol. 95, pp. 10443-10448 (1998).
Folkman J., "Antiangiogenesis in cancer therapy—endostatin and its mechanisms of action," Exper. Cell Res., vol. 312, pp. 594-607 (2006).
Gordon et al., "Phase I Safety and Pharmacokinetic Study of Recombinant Human Anti-Vascular Endothelial Growth Factor in Patients With Advanced Cancer," J. Clin. Oncology, vol. 19, pp. 843-850 (2001).
Heljasvaara et al., "Generation of biologically active endostatin fragments from human collagen XVIII by distinct matrix metalloproteases," Exp. Cell Res., vol. 307, pp. 292-304 (2005).
Holash et al., "VEGF-Trap: A VEGF blocker with potent antitumor effects," PNAS, vol. 99, pp. 11393-11398 (2002).
Italiano Jr., et al., "Angiogenesis is regulated by a novel mechanism: pro- and antiangiogenic proteins are organized into separate platelet α granules and differentially released," Blood, vol. 111, pp. 1227-1233 (2008).
Javaherian et al., "Laminin Modulates Morphogenic Properties of the Collagen XVIII Endostatin Domain," J. Biol. Chem., vol. 277, pp. 45211-45218 (2002).
Jing et al., "Inhibition of ovarian cancer by RGD-P125A-endostatin-Fc fusion proteins," Int. J. Cancer, vol. 129, pp. 751-761 (2011).
Kuo et al., "Oligomerization-dependent Regulation of Motility and Morphogenesis by the Collagen XVIII NC1/Endostatin Domain," J. Cell. Biol., vol. 152, pp. 1233-1246 (2001).
Lee et al., "Linking Antibody Fc Domain to Endostatin Significantly Improves Endostatin Half-life and Efficacy," Clin. Cancer Res., vol. 14, pp. 1487-1493 (2008).
Li et al., "Efficacy and Safety of Endostar Combined with Chemotherapy in Patients with Advanced Solid Tumors," Asian Pacific J. of Cancer Prevention, vol. 11, pp. 1119-1123 (2010).
Li et al., "RGD-Modified Endostatin Peptide 30 Derived from Endostatin Suppresses Invasion and Migration of HepG2 Cells Through the αvβ3 Pathway," Cancer Biotherapy and Radiopharmaceuticals, vol. 26, pp. 529-538 (2011).
Ling et al., "Endostar, a novel recombinant human endostatin, exerts antiangiogenic effect via blocking VEGF-induced tyrosine phosphorylation of KDR/Flk-1 of endothelial cells," Biochem. Biophy. Res. Comm., vol. 361, pp. 79-84 (2007).
Lo et al., "High level expression and secretion of Fc-X fusion proteins in mammalian cells," Protein Engineering, vol. 11, pp. 495-500 (1998).
Sanchez-Arevalo et al., "Enhanced antiangiogenic therapy with antibody-collagen XVIII NC1 domain fusion proteins engineered to exploit matrix remodeling events," Int. J. Cancer, vol. 119, pp. 455-462 (2006).

O'Reilly et al., "Endostatin: An Endogenous Inhibitor of Angiogenesis and Tumor Growth," Cell, vol. 88, pp. 277-285 (1997).
Oh et al., "Isolation and sequencing of cDNAs for proteins with multiple domains of Gly-Xaa-Yaa repeats identify a distinct family of collagenous proteins," Proc. Natl. Acad. Sci. USA, vol. 91, pp. 4229-4233 (1994).
Rehn et al., "Interaction of endostatin with integrins implicated in angiogenesis," PNAS, vol. 98, pp. 1024-1029 (2001).
Sasaki et al., "Endostatins Derived from Collagens XV and XVIII Differ in Structural and Binding Properties, Tissue Distribution and Anti-angiogenic Activity," J. Mol. Biol., vol. 301, pp. 1179-1190 (2000).
Sim et al., "Zinc ligand-disrupted recombinant human Endostatin: Potent inhibition of tumor growth, safety and pharmacokinetic profile," Angiogenesis, vol. 3, pp. 41-51 (1999).
Sjin et al., "A 27-Amino-Acid Synthetic Peptide Corresponding to the NH2-Terminal Zinc-Binding Domain of Endostatin Is Responsible for Its Antitumor Activity," Cancer Res., vol. 65, pp. 3656-3663 (2005).
Wen et al., "The Generation of Endostatin Is Mediated by Elastase," Cancer Res., vol. 59, pp. 6052-6056 (1999).
Wickström et al., "Endostatin Associates with Integrin $\alpha_5\beta_1$ and Caveolin-1, and Activates Src via a Tyrosyl Phosphatase-dependent Pathway in Human Endothelial Cells," Cancer Res., vol. 62, pp. 5580-5589 (2002).
Wijelath et al., "Heparin-II Domain of Fibronectin Is a Vascular Endothelial Growth Factor-Binding Domain: Enhancement of VEGF Biological Activity by a Singular Growth Factor/Matrix Protein Synergism," Cir. Res., vol. 99, pp. 853-860 (2006).
Yi et al., "Antiangiogenic proteins require plasma fibronectin or vitronectin for in vivo activity," PNAS, vol. 100, pp. 11435-11438 (2003).
International Preliminary Report on Patentability issued in related International Patent Application No. PCT/EP2012/066467, completed Mar. 6, 2014.
Ackley et al., "The NC1/Endostatin Domain of Caenorhabditis elegans Type XVIII Collagen Affects Cell Migration and Axon Guidance," The Journ. Of Cell Biology, vol. 152, No. 6, pp. 1219-1232 (Mar. 2001).
Cuesta, et al., "Improved Stability of Multivalent Antibodies containing the Human Collagen XV Trimerization Domain," mAbs, vol. 4, No. 2, pp. 226-232 (Mar./Apr. 2012).
Yoshida et al., "Inhibition of Corneal Neovascularization by Subconjunctival Injection of Fc-Endostatin, a Novel of Angiogenesis," Journal of Ophthalmologyi, vol. 2015, 8 pages (Jan. 2015).
International Search Report issued in related International Patent Application No. PCT/EP2012/066467, completed Feb. 13, 2013.
Peters et al., "Prolonged Activity of Factor IX as a Monomeric Fc Fusion Protein," Blood, vol. 115, pp. 2057-2064 (2010).
Ritzenthaler et al., "Stimulation of Lung Carcinoma Cell Grown by Fibronectin-integrin Signaliing," Mol. BioSyst., vol. 4, pp. 1160-1169 (2008).
Yu et al., "E-Selectin is Required for the Antiangiogenic Activity of Endostatin," Proc. Natl. Acad. Sci., vol. 101, No. 21, pp. 8005-8010 (2004).
Yokoyama et al., "Binding of Endostatin to Human Ovarian Cancer Cells Inhibits Cell Attachment," Int. J. Cancer, vol. 121, pp. 2402-2409 (2007).
Li et al., "Increased Angiogenic Response in Aortic Explants of Collagen XVIII/Endostatin-Null Mice," American Journ. of Pathology, vol. 165, No. 2, pp. 415-424 (2004).
Chen, et al., "NC1 Domain of Type VII Collagen Binds to the β3 Chain of Laminin 5 Via a Unique Subdomain within the Fibronectin-Like Repeats," J. Invest. Dermatol., vol. 112, pp. 177-183 (1999).
Xu et al., "An RGD-Modified Endostatin-Derived Synthetic Peptide Shows Antitimor Activity in Vivo," Bioconjugate Chem., vol. 19, No. 10, 1980-1986 (2008).
Livant, et al., "The PHSRN sequence induces extracellular matrix invasion and accelerates wound healing in obese diabetic mice," J. Clin. Invest., vol. 105, No. 11, pp. 1537-1545 (2000).
Jing, et al., "Inhibition of Ovarian Cancer by RGD-P125A-endostatin-Fc fusion proteins," Int. J. Cancer, vol. 129, No. 3, pp. 751-761 (2011).

(56)                  References Cited

OTHER PUBLICATIONS

Jing, et al., "Fusion protein containing RGD-endostatin and human Fc of IgG4improves anti-angiogenic and anti-tumor activity," *Cancer Research*, vol. 70, No. 8, Suppl 1, Abstract No. 1385 (Apr. 2010).

Search Report issued in co-pending European Patent Application No. 22206486 dated Jun. 21, 2023 (13 pages).

Sabatino et al., "Serum vascular endothelial growth factor and fibronectin predict clinical response to high-dose interleukin-2 therapy," Journal of Clinical Oncology, Jun. 1, 2009, vol. 27, No. 16 (pp. 2645-2652).

* cited by examiner

Fig1.A
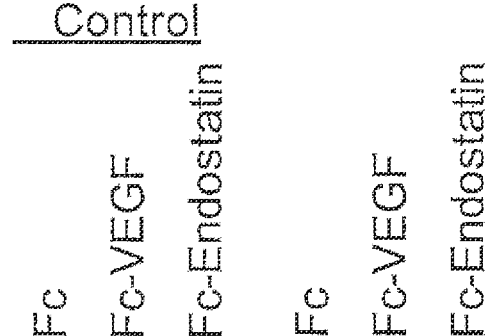
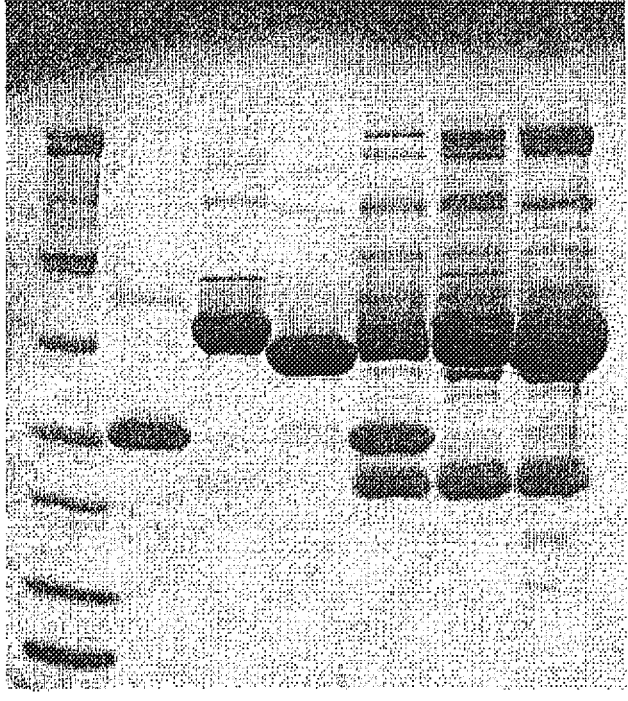

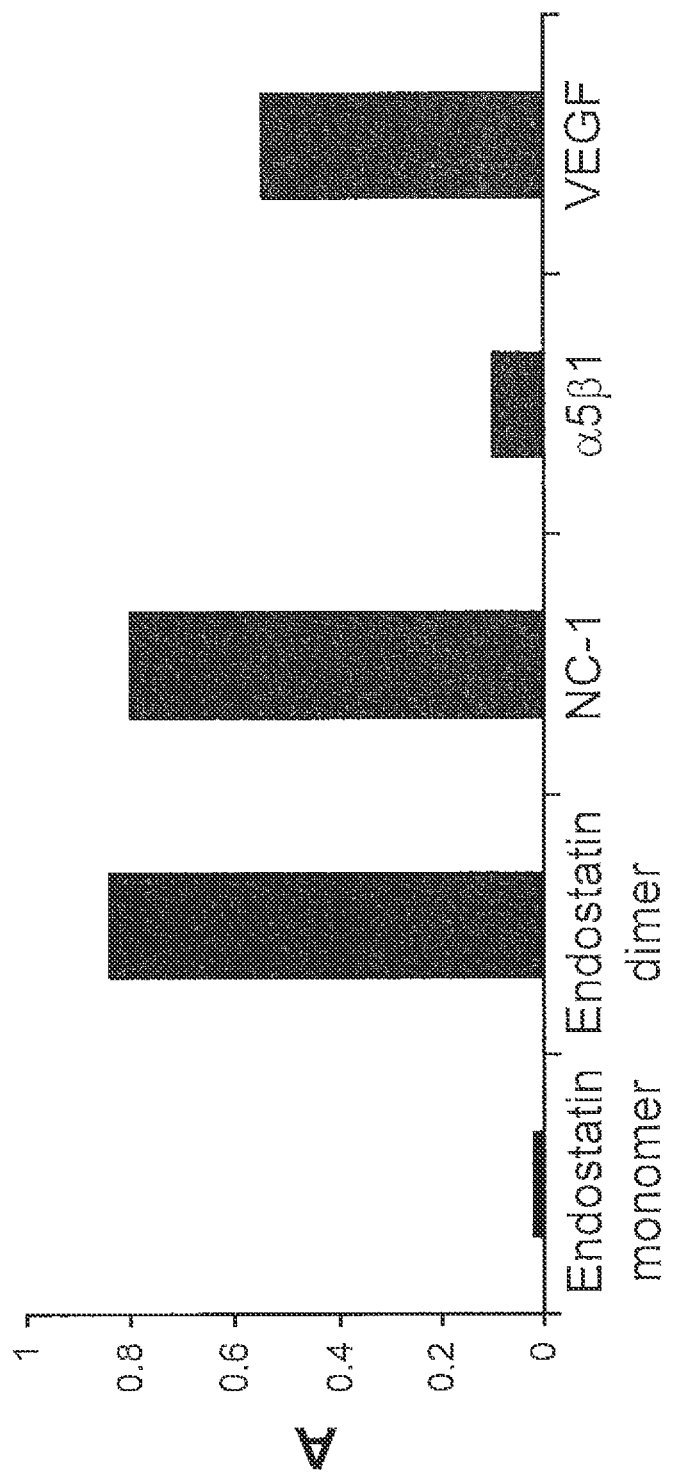
Fig1.B

Anti-ColXVIII          Anti-FN          Merge

Anti-FN                    Anti-VEGF                    Anti-FcES

Fig. 8.1
LLC Tumor Growth Inhibition
- Control (n=18)
- mFc-Endostatin (20/d, n=5)
- mFc-Angiostatin (100/6d, n=5)

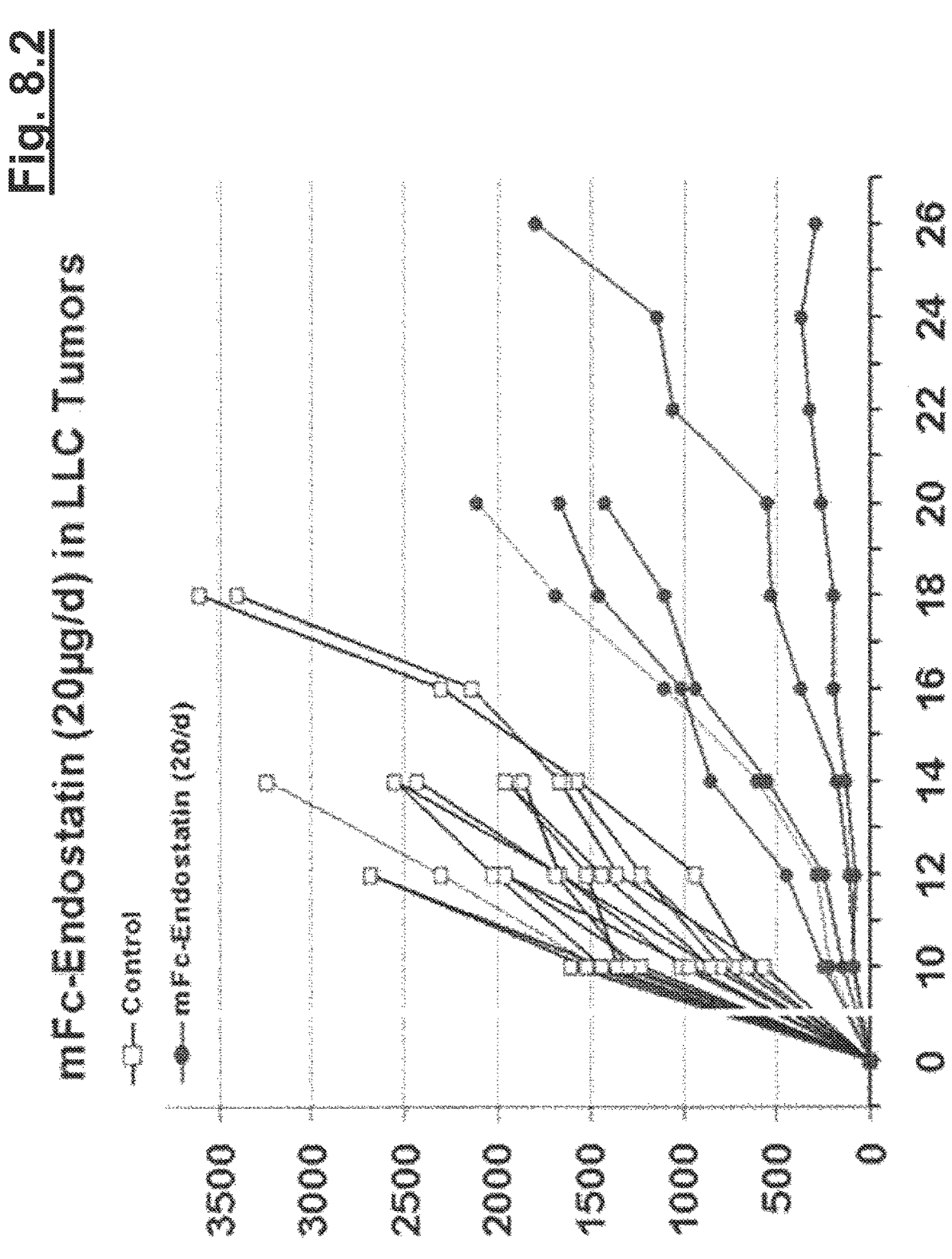
Fig. 8.2

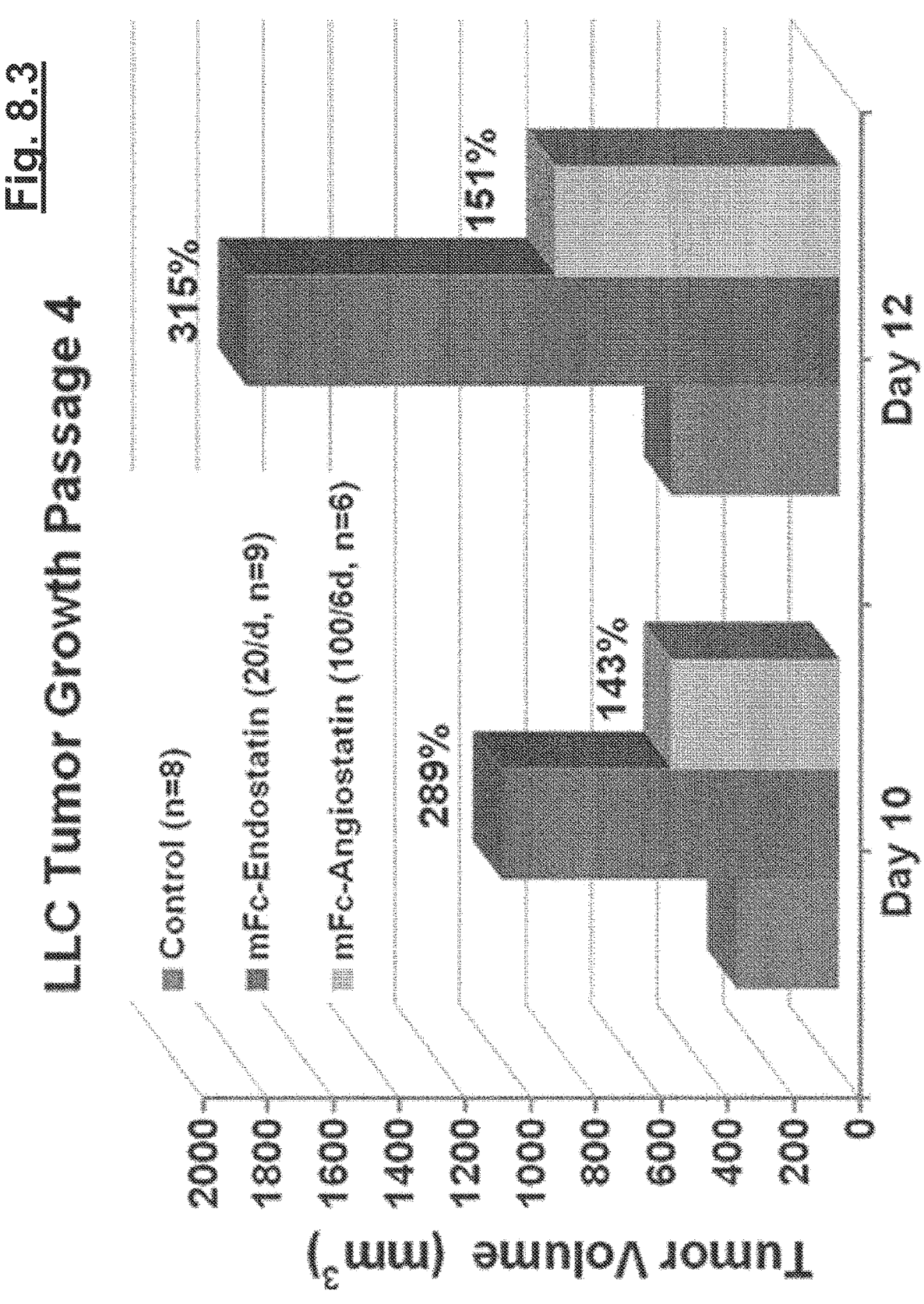
Fig. 8.3

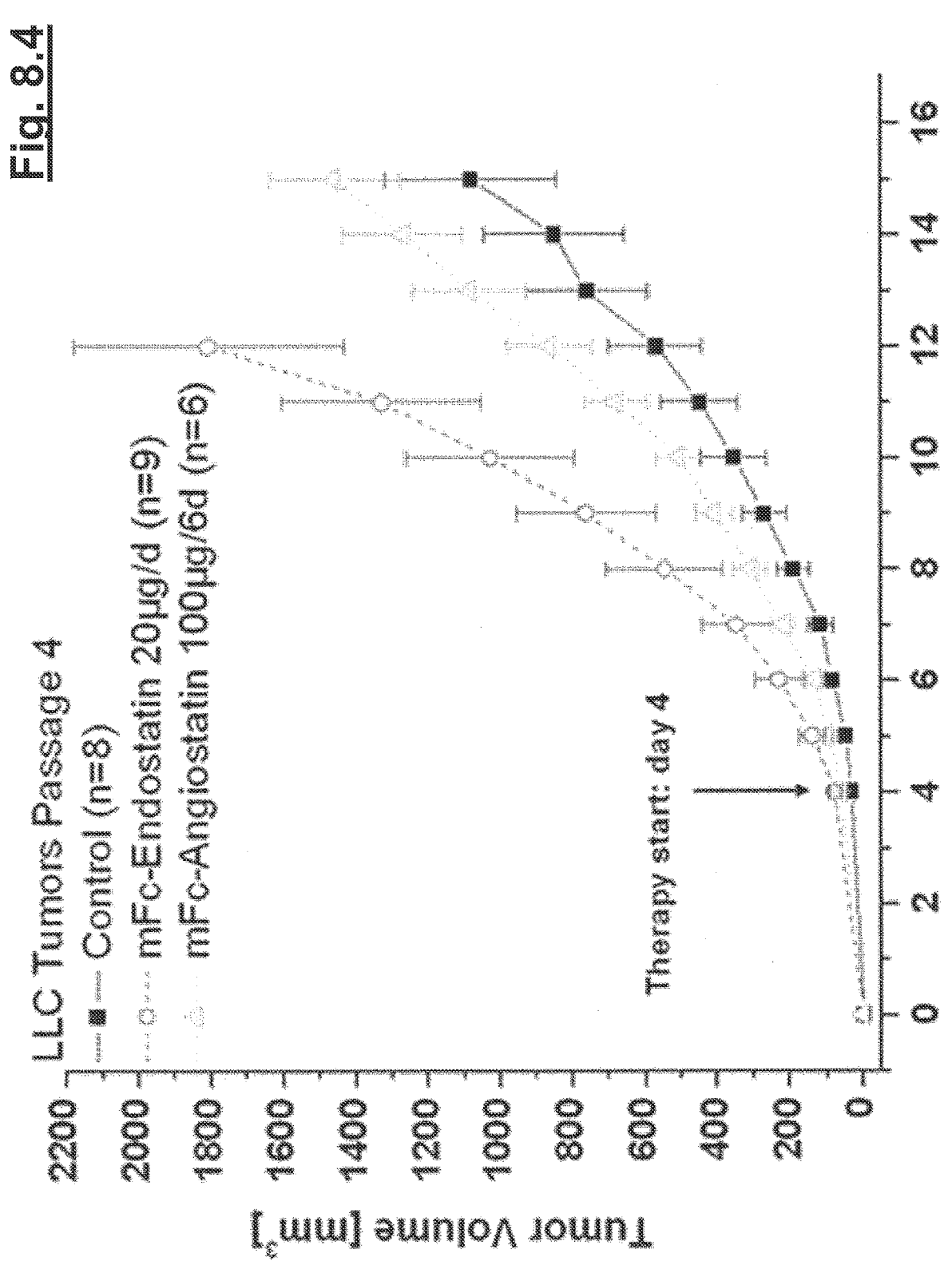
Fig. 8.4

FIG. 9.1
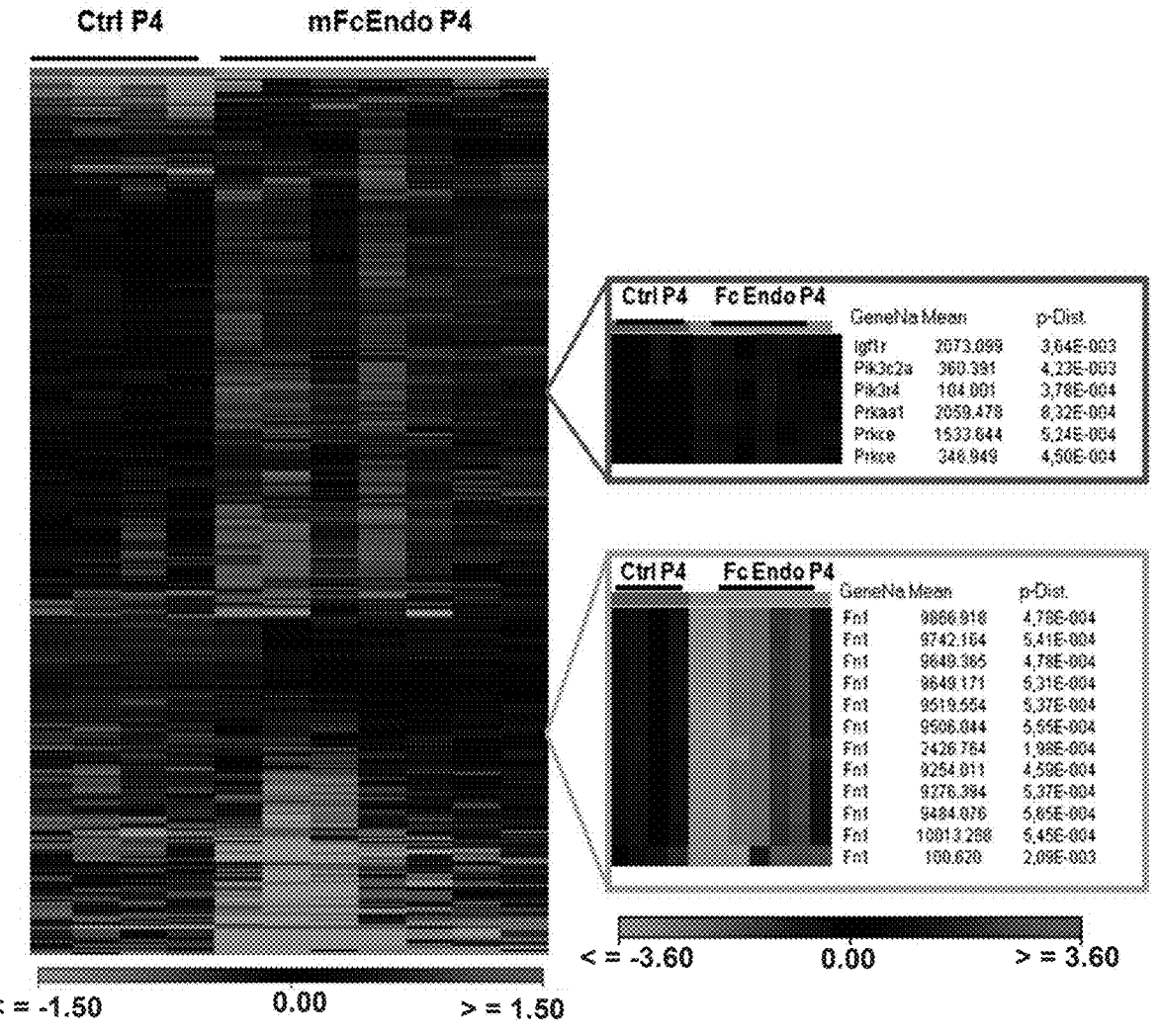

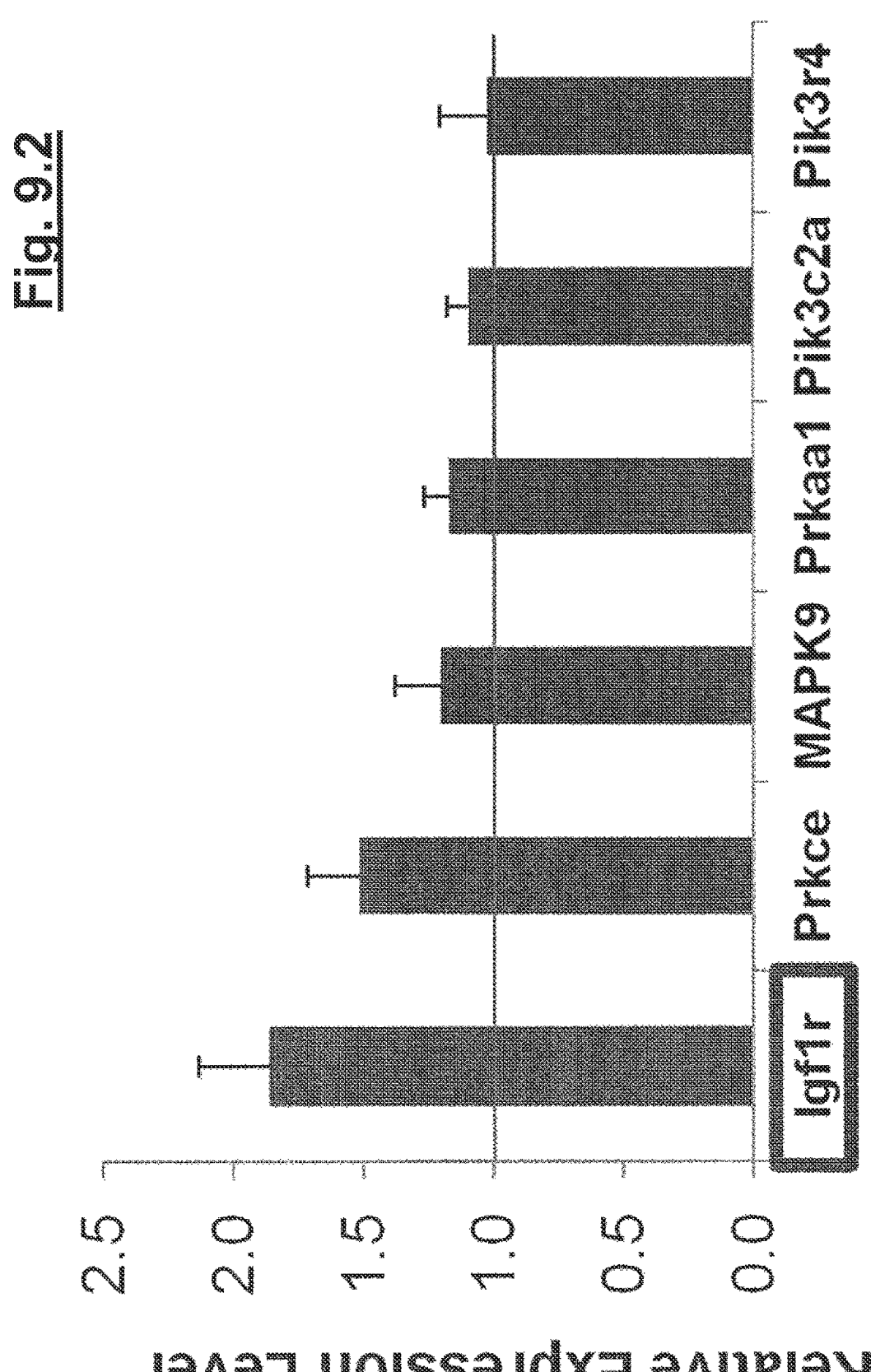
Fig. 9.2

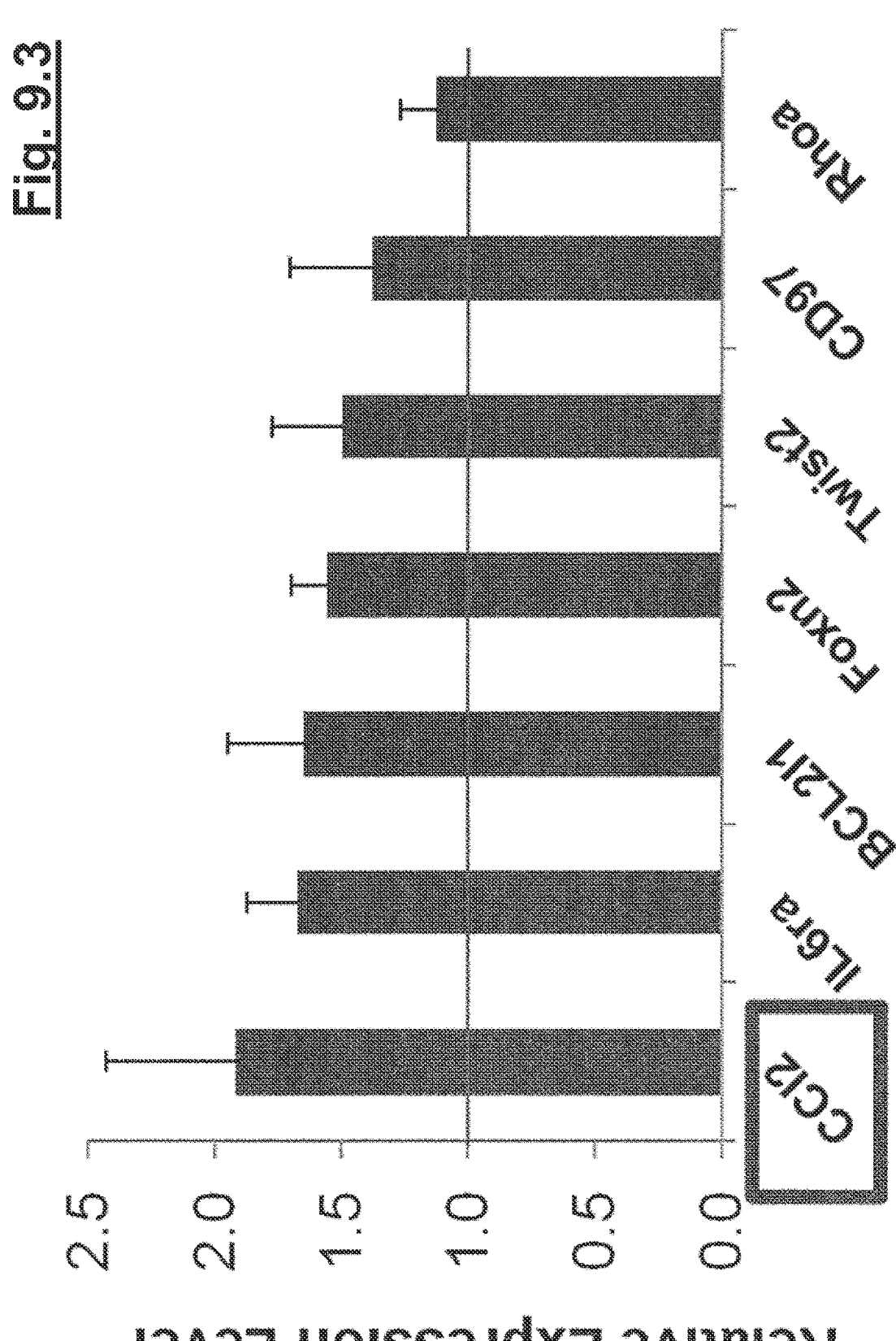
Fig. 9.3

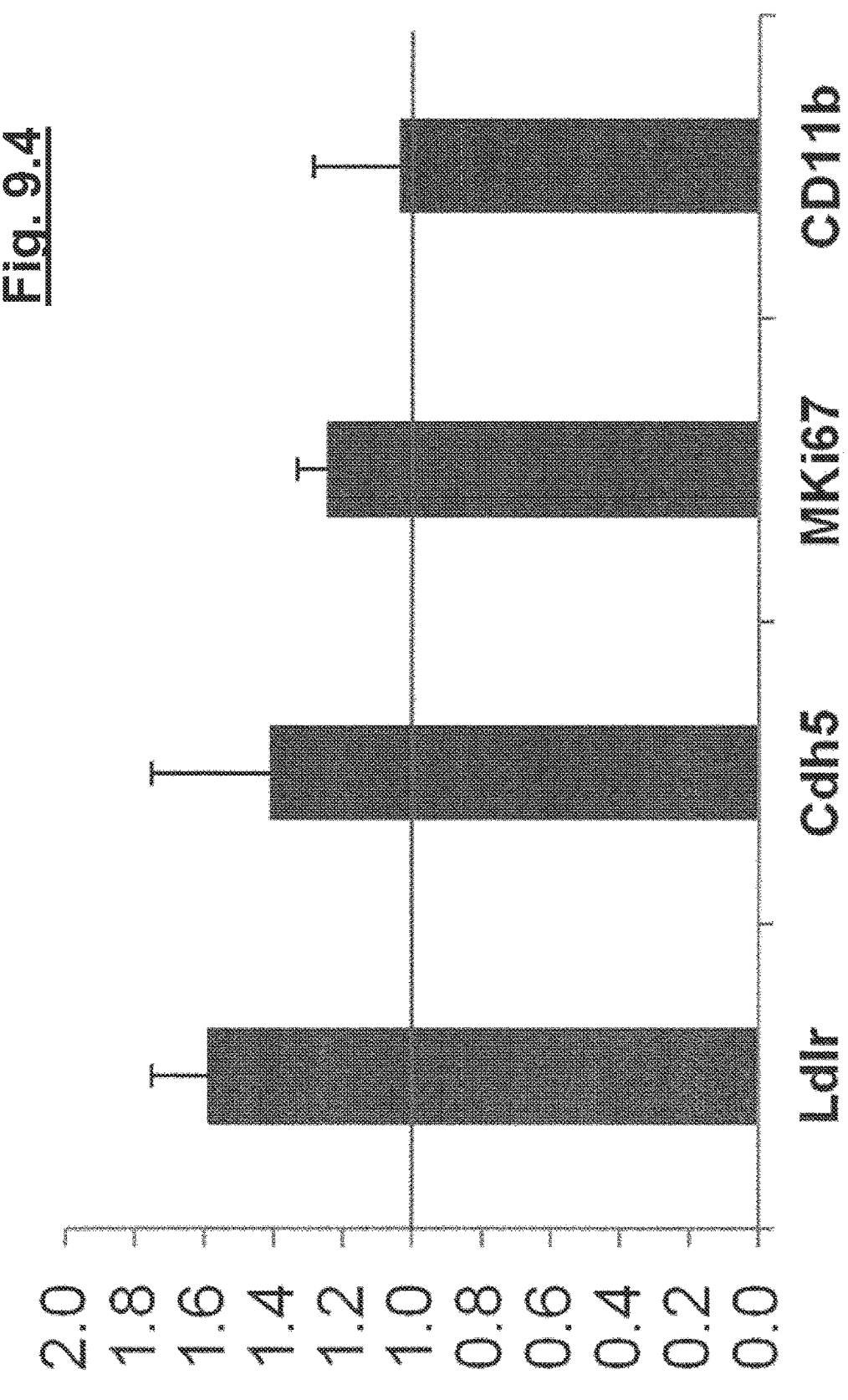
Fig. 9.4

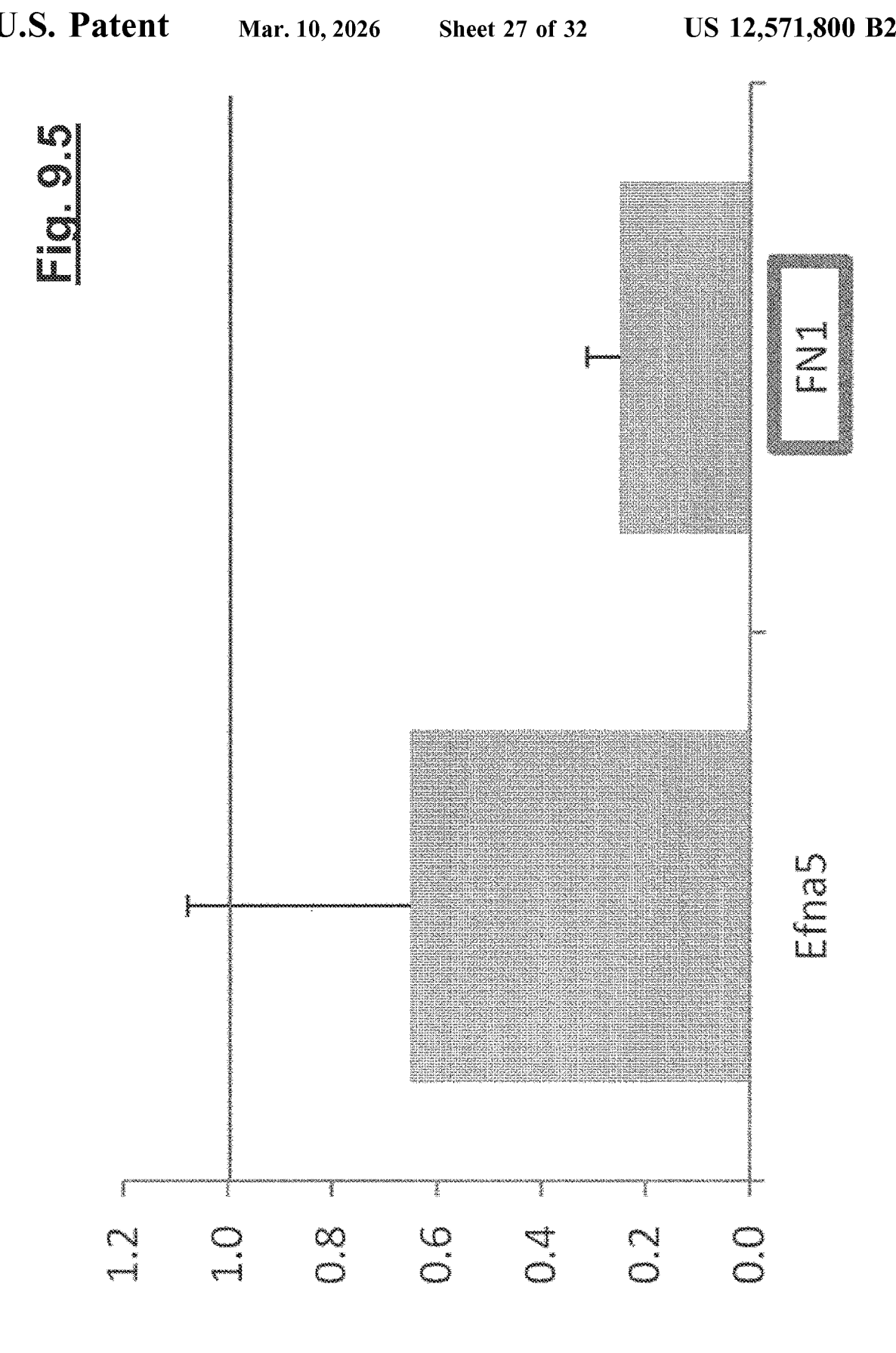
Fig. 9.5

MEANS AND METHODS FOR TREATING ANGIOGENESIS-RELATED DISEASES

CROSS-REFERENCE TO RELATED APPLICATIONS

This application is a Divisional of U.S. patent application Ser. No. 14/240,273, filed Jun. 24, 2014, which is the U.S. National Phase of International Patent Application No. PCT/EP2012/066467, filed Aug. 23, 2012, which claims priority from U.S. Provisional Patent Application No. 61/526,535, filed Aug. 23, 2011, and European Patent Application No. 11178509.3, filed Aug. 23, 2011. The contents of these applications are incorporated herein by reference in their entirety.

SEQUENCE LISTING

The instant application contains a Sequence Listing which has been submitted in XML format via Patent Center and is hereby incorporated by reference in its entirety. Said XML copy, created on Oct. 22, 2024, is named 097147-0158.xml, and is 22,854 bytes.

The present invention is concerned with a protein oligomer comprising at least two NC-1 monomers of human collagen 18 or fragments of an NC-1 monomer of human collagen 18 for use in the treatment or prevention of an angiogenesis-related disease. The invention further pertains to a fusion protein comprising a NC-1 monomer of human collagen 18 and a Fc domain of an immunoglobulin. The invention also relates to a fusion protein comprising: a) an endostatin peptide or endostatin-derived peptide and b) the RGD motif and/or PHSRN motif (SEQ ID NO: 20) of Fibronectin. The invention further relates to a kit comprising the protein oligomer or fusion proteins of the invention.

Endostatin, a 183-amino acid proteolytic cleavage fragment corresponding to the C-terminus of collagen 18 (or collagen XVIII), has been the subject of investigation by a number of laboratories because of its anti-tumor activity and its potential application as an anti-angiogenic cancer therapeutic (O'Reilly et al., 1997, *Cell* 88, 277; Folkman et al., 2006, *Exp Cell Res* 312, 594; Bergers et al., 1999, *Science* 284, 808). The anti-tumor activity of endostatin is well established. Although the number of separate mechanisms for endostatin action has been proposed, a general consensus on its mechanism is yet absent.

Clinical trials of human endostatin in phase I and II used a recombinant molecule that was expressed in yeast. This formulation of endostatin carried two major handicaps. The half-life of the protein in circulation was very short and 50% of the injected recombinant human endostatin used in the original clinical trials lacked four amino acids at the N-terminus, including two histidines crucial for zinc binding, hence an inactive molecule (Lee et al., 2008, *Clin Cancer Res* 14, 1487; Boehm et al., 1998, *Biochem Biophys Res Commun* 252, 190; Tjin et al., 2005, Cancer Res 65, 3656; Sim et al., 1999, Angiogenesis 3, 41). To overcome these deficiencies, a novel recombinant human endostatin expressed and purified in *Escherichia coli* with an additional nine-amino acid sequence and forming another his-tag structure, called Endostar, was approved by the SDFA in 2005 for the treatment of non-small-cell lung cancer. Endostar suppressed the VEGF-stimulated proliferation, migration, and tube formation of human umbilical vein endothelial cells (HUVECs) in vitro and blocked microvessel sprouting from rat aortic rings in vitro. Moreover, it could inhibit the formation of new capillaries from pre-existing vessels in the chicken chorioallantoic membrane (CAM) assay and affect the growth of vessels in tumor. It has further been found that the antiangiogenic effects of endostar were correlated with the VEGF-triggered signaling (Ling et al. *Biochem Biophys Res Com* 361, 79). In another study, endostatin fused to the Fc domain of an IgG antibody has been constructed (Lee et al., 2008, *Clin Cancer Res* 14, 1487). The presence of Fc increased the half-life to longer than a week, analogous to the two angiogenesis inhibitors bevacizumab (Avastin) and VEGF-Trap (Gordon et al., 2001, *J Clin Oncol* 19, 843; Holash et al., 2002, *Proc Natl Acad Sci USA* 99, 11393).

Although numerous clinical trials proved that endostatin is a very safe drug in a variety of dose schedules, the results did not demonstrate substantial endostatin anti-tumor activity. The dose and schedules may have been sub-optimal, and/or bulky disease in late stage patients may not be optimally responsive to recombinant human endostatin. Therefore, in current clinical trials in China, endostatin is mainly used in combination with chemotherapeutics in order to improve anti-tumor activity of endostatin. For example, in one study, 45 patients with solid tumors were enrolled. All received Endostar at a dose of 7.5 mg/m²/day as an intravenous infusion for more than 7 days, in combination with chemotherapy, from 2006 to 2008. No treatment related death occurred in this study. Main reported toxicities included myelosuppression, hepatic impairment, anorexia, nausea, vomiting, diarrhea, febrile and fatigue. No complete response was observed. Two of 42 patients had partial response, twenty-one remained stable, and nineteen had progressive disease. Median time to tumor progression was 3.0 months. Median overall survival was 30.0 months and one year survival rate was 81.0%. This data showed that toxicity of Endostar combined with chemotherapy in the treatment of solid tumors was tolerable with moderate efficacy (Li et al. 2010, *Asian Pac J Cancer Prev.* 11, 1119-23).

Anti-angiogenic gene therapy has been proposed as an alternative way to continuously provide high concentrations of the anti-angiogenic factors. Gene transfection of anti-angiogenic agents using a viral vector can inhibit the growth of tumors in several mouse models. Viral vectors, however, may cause inflammation and immunological response on repeated injection, and toxicity/safety considerations may preclude the use in humans in the near future. In addition, use of gene-transduced hematopoietic stem cells has been ineffective in an animal model, despite sustained production of endostatin. Furthermore, dosing of biological products using gene vectors is very difficult to standardize due to variation in vector titer, transduction efficiency and expression levels.

There is, thus, a need in the art for improved therapies of angiogenesis-related diseases.

The technical problem underlying the present invention could be seen as the provision of means and methods which comply with the afore-mentioned needs. This technical problem has been solved by the embodiments characterized in the claims and herein below.

Accordingly, the present invention relates to a protein oligomer comprising at least two NC-1 monomers of human collagen 18 or fragments of an NC-1 monomer of human collagen 18 for the treatment or prevention of an angiogenesis-related disease.

The term "collagen 18" and "collagen XVIII" as used herein are used interchangeably and refer to the same protein. The cloning of the mouse and human collagen 18 proteins has been described by Oh et al. (PNAS 1994, 91, 4229; Genomics 1994, 19, 494). The Type XVIII collagen belongs to a unique and novel subclass of the collagen superfamily for which the name "MULTIPLEXIN family" has been proposed. The nucleotide and amino acid sequences of mouse collagen 18 are shown in accession number NM_001109991.1 whereas the corresponding human sequences are shown in NM_030582.3. Further, the amino acid sequences of mouse and human collagen 18 are shown in SEQ ID NOs: 1 and 2, respectively. More specifically, collagen 18 consists of a central, interrupted triple-helical domain flanked at the N-terminus (NC-11 domain) and C-terminus (NC-1 domain) by larger non-triple helical, globular structures (Oh et al., loc. cit.; Abe et al. 1993, *Biochem Biophys Res Commun* 196, 576).

The C-terminal NC-1 domain (or briefly NC-1) of collagen 18 includes an N-terminal association region (of about 50 amino acid residues), a central protease-sensitive hinge region (of about 70 amino acid residues) and a C-terminal stable endostatin domain (of about 180 amino acid residues) (Sasaki et al., 1998, EMBO J 17, 4249). The endostatin domain comprises a zinc binding site which mediates binding to zinc and is located at the N terminus of endostatin (Ding et al., 1998, PNAS 95, 10443; U.S. Pat. No. 7,524, 811). Interestingly, this zinc binding site has been shown to be responsible for the anti-tumor/anti-angiogenic activity of endostatin (Boehm et al., 1998, *Biochem. Biophys. Res. Commun.* 252, 190). The amino acid sequence of the NC-1 domain of the mouse collagen 18 is depicted in SEQ ID NO: 3, whereas the corresponding sequence of the NC-1 domain of human collagen 18 sequence is shown in SEQ ID NO: 4. The association domain of the human NC-1 domain comprising amino acid residues from about 10 to about 60 of the amino acid sequence shown in SEQ ID NO: 4 is responsible for non-covalent trimerization of the NC-1 monomer to form a globular trimer. The proteolytic cleavage-sensitive hinge region comprises amino acid residues from about 61 to about 129 of the amino acid sequence shown in SEQ ID NO: 4. The compact endostatin domain comprises amino acid residues from about 130 to about 308 of the amino acid sequence shown in SEQ ID NO: 4; see, e.g., Sasaki, loc. cit.; Kuo 2001, *JCB* 152, 1233; Tjin et al. 2005, *Cancer Res* 65, 3656. The association region and the endostatin domain in the NC-1 domain are connected by the hinge region (see Sasaki et al., loc. cit.). The hinge region has been found to be cleaved, for instance, by matrix metalloproteinases (MMPs), such as MMP-3, -7, -9, -13 and -20 (Heliasvaara et al., *Exp Cell Res* 2005, 307, 192). The above-indicated domain structure of NC-1 is based on structural data. The term "about" as used for the positioning of the domains within NC-1 reflects the fact that the exact boundaries between the mentioned domains may differ from the indicated positions by one, two, three or even more amino acid residues. The exact boundary between, for example, the association domain and the hinge region can be determined, for example, by generating an association domain comprising amino acid residues from about 10 to about 60 of SEQ ID NO: 4 as a starting point and producing shorter fragments thereof, e.g. with a length of 49, 48, 47, 46, 45 and so on, amino acid residues. Said shorter fragments can then be analyzed for their oligomerization properties, i.e. whether they are still able to form oligomers, such as trimers, as the complete association domain does. Alternatively, the endostatin domain may serve as a starting point to address the oligomerization properties of the domains of NC-1. As indicated elsewhere herein, the invention provides for a further method for identifying the exact boundaries of the monomer, dimer and/or trimer transitions in the NC-1 domain as defined herein. However, the above-mentioned domain model fits the gene structure remarkably well, with exons 38 and 39 encoding the association domain, exon 40 the hinge region, and three more exons the endostatin domain (Sasaki et al., loc. cit.).

The term "protein" or "polypeptide" or "peptide" as used herein encompasses isolated or essentially purified (poly) peptides being essentially free of other host cell polypeptides. The term "peptide" as used herein comprises at least two, three, four, five, six, seven, eight, nine, ten, 11, 12, 13, 14, 15, 16, 17, 18, 19, 20, 21, 22, 23, 24, 25, 26, 27, 28, 29, 30, 35, 40 or even more amino acid residues where the alpha carboxyl group of one is bound to the alpha amino group of another. The term "peptide" as used herein encompasses peptidomimetics. As known in the art, peptidomimetics are compounds whose essential elements (pharmacophore) mimic a natural peptide or protein in 3D space and which retain the ability to interact with the biological target and produce the same biological effect; see, e.g., the review by Vagner et al. 2008, Current Opinion in Chemical Biology 12, Pages 292-296. Peptidomimetics are designed to circumvent some of the problems associated with a natural peptide: e.g. stability against proteolysis (duration of activity) and poor bioavailability. Certain other properties, such as receptor selectivity or potency, often can be substantially improved. According to the present invention, the protein or peptide is in one aspect an oligomer. In another aspect, the protein or peptide is a fusion protein, as further defined below. An "oligomer" as used herein means a molecule that comprises a few monomer units, in contrast to a polymer that, at least in principle, comprises an unlimited number of monomers. Preferably, the oligomer is a protein oligomer, i.e. the oligomer comprises two, three, four, five or even more protein monomers, i.e. the oligomer can be, e.g., a dimer, trimer, tetramer, pentamer and so on. A dimer is per definition a macromolecular complex formed by two, usually non-covalently bound, molecules like proteins or peptides. Such a complex can also be formed by protein domains which are parts of protein sequences and structures that can evolve, function, and exist independently of the rest of the protein chains. A homo-dimer is formed by two identical molecules, the underlying process is called homo-dimerization. A hetero-dimer is built by two different macromolecules which are formed by hetero-dimerization. As known in the art, most dimers in biochemistry are not connected by covalent bonds, with the exception of disulfide bridges. Some proteins contain specialized domains to ensure dimerization (or oligomerization), so called dimerization (or oligomerization) domains, as further defined herein below and well known in the art. A trimer is a macromolecular complex formed by three, usually non-covalently bound proteins or protein domains. A homo-trimer is formed by three identical molecules, whereas a hetero-trimer is built by three different molecules. For example, collagen 18 is a homo-trimeric protein. A tetramer consists of four molecules, a pentamer of five molecules, and so on. In these cases, complex formation is often mediated by oligomerization domains, as set forth above. For instance, dimerization can be mediated by an Fc domain of an immunoglobulin or by disulfide bridges as described elsewhere herein, whereas for the trimerization of NC-1 of collagen 18, the association region within the NC-1 domain can be used.

The protein or peptide oligomer of the present invention comprises at least two NC-1 monomers of collagen 18, as defined herein. However, the protein oligomer can comprise also three, four, five, six or even more of said NC-1 monomers of collagen 18, preferably, of human collagen 18. It is also encompassed by the scope of the present invention in some aspects that the protein oligomers or fusion proteins as referred to herein can oligomerize via one or more disulfide bonds. It is further envisaged, that the NC-1 monomers as defined herein are linked covalently, for instance, by chemical cross linking or other methods known in the art.

The term "protein" or "peptide" as used herein includes also protein preparations comprising the protein oligomer or peptide oligomer or fusion protein of the present invention and other proteins in addition. Moreover, the term includes, in an aspect, chemically modified protein or peptide oligomers or fusion proteins. Such modifications may be artificial modifications or naturally occurring modifications.

The protein oligomer or peptide oligomer or fusion protein of the present invention shall have the biological properties referred to herein, preferably anti-angiogenic activities. Such anti-angiogenic activities include, for example, any biological activity inhibiting the growth or migration of endothelial cells and/or pericytes, formation of tubes or endothelium, growth of new capillary blood vessels in the body, slowing or inhibiting of the growth of benign or malignant tumors by cutting off their blood supply, reduce side-effects/toxicity of other anti-tumor or anti-angiogenic agents, e.g., VEGF-Inhibitors, by interference with their mechanism of action, i.e. reduce blood pressure, modulation of inflammatory response in malignant and benign diseases, or improving the patho-physiological parameters, such as perfusion or hypoxia within a therapeutic time window after treatment that, in turn, may facilitate the efficacy of additional therapies (e.g., radiotherapy, chemotherapy or antiapoptotic therapy). The anti-angiogenic activity can be tested by in vitro assays or in vivo by animal models known in the art (Abdollahi et al., *Cancer Res.* 2003, 63, 8890; *Mol. Cell* 2004, 13, 649; PNAS 2007, 104, 12890; *Drug Resist. Update* 2005, 8, 59; Bergers et al., *Science* 1999, 284, 808; Javaherian et al., *J. Biol. Chem.* 2002, 277, 45211; Lee et al., *Clin. Cancer Res.* 2008). For instance, the anti-angiogenic activity can be tested in vitro by inhibition of the proliferation and/or migration of endothelial cells stimulated by a growth factor, e.g., by VEGF. In vivo, anti-angiogenic activity can be analyzed, for example, by a chicken chorioallantoic membrane (CAM) assay, whereas an anti-tumor activity can be tested in animal tumor models including, e.g., A549, LLC or H460 non-small cell lung carcinoma, HT29 colon carcinoma, BxPC3 Pancreatic Carcinoma, Karpas 299 lymphoma, MOLM-13 AML (acute myeloid leukemia), 786-0, A2058 cell line (melanoma) or RENCA renal cell carcinoma (RCC) and many others (Abdollahi et al., *Drug Resist.* Update 2005, loc. cit.).

The protein oligomer or peptide oligomer or fusion protein of the invention, in an aspect, can be manufactured by chemical synthesis or recombinant molecular biology techniques well known to the person skilled in the art; see, e.g., Sambrook et al. 2001, Molecular cloning: a laboratory manual/Sambrook, Joseph; Russell, David W.—. 3rd ed.— New York: Cold Spring Harbor Laboratory, 2001. In an aspect, such a method of manufacturing the protein oligomer or peptide oligomer or fusion protein of the present invention comprises (a) culturing a host cell comprising a nucleic acid encoding the protein oligomer or peptide oligomer or fusion protein of the invention and (b) obtaining from the host cell of step (a) the protein oligomer or peptide oligomer or fusion protein, and, optionally, storing the protein oligomer or peptide oligomer or fusion protein. Preferably, said method is carried out under serum-free conditions, since it has been found by the present inventors that protein oligomers comprising two or more NC-1 monomers as defined herein are susceptible to degradation in serum or cell culture medium comprising serum. In an aspect of this method, the protein oligomer or peptide oligomer or fusion protein can be obtained by conventional purification techniques from, e.g., a host cell lysate including, but not limited to, affinity chromatography, ion exchange chromatography, size exclusion chromatography and/or preparative gel electrophoresis.

In one embodiment of the protein oligomer or peptide oligomer or fusion protein of the invention, the "NC-1 monomer", "NC-1 monomer of collagen 18" or "NC-1 monomer of human collagen 18" as used herein in the protein oligomer or peptide oligomer or fusion protein of the invention comprises at least one part, i.e. at least one domain, region or fragment, of the non-collagenous NC-1 domain of human collagen 18, as defined herein. It is preferred that the NC-1 monomer is human. The NC-1 monomer as used herein comprises, in one aspect of the protein oligomer or peptide oligomer or fusion protein of the invention, at least one endostatin-derived peptide or endostatin peptide, comprising the zinc binding site/domain of the endostatin domain. The human endostatin zinc binding site is formed by histidines 1, 3 and 11 and aspartic acid 76 (Ding et al., loc. cit.). It has been reported that zinc binding of endostatin is essential for its anti-angiogenic activity (Boehm et al., loc. cit.). Further, Tjin et al. (loc. cit.) found that a 27 amino amino acid synthetic peptide corresponding to the N-terminal zinc binding domain of endostatin is responsible for its antitumor activity. The term "endostatin peptide" as used herein means that the amino acid sequence of this peptide can be found in the endostatin domain of NC-1. The term "endostatin-derived peptide" means that such a peptide can differ from the corresponding endostatin peptide in the endostatin domain of NC-1, in one, two, three, four or even more amino acid residues, while at least maintaining (or even exceeding) the biological activity (as described elsewhere herein) of the corresponding endostatin peptide in the endostatin domain of NC-1. Examples of endostatin peptides comprising said zinc binding site/domain of the endostatin domain and exhibiting anti-angiogenic and/or anti-tumor activity have been described, e.g., in Tjin et al., loc. cit., or in U.S. Pat. No. 7,524,811. Preferably, the endostatin-derived peptide or endostatin peptide is about 10 to about 40 amino acid residues in length, preferably 23 to 35, more preferably 24, 25, 26, 27, 28, 29 or 30 amino acid residues. For example, SEQ ID NO: 9 shows the corresponding murine sequence of the active motif of NC-1-endostatin domain (ED) (i.e., the amino-terminal zinc binding domain mediating antiangiogenic and/or antitumor activity) with a length of 26 amino acid residues, whereas SEQ ID NO: 10 shows the corresponding human sequence with a length of 25 amino acid residues. The Histidines in these sequences are particularly important since it has been found by the present inventors in a previous study, that substitution of said Histidines by Alanine residues abolished antitumor and antiangiogenic activity; see Example 2.10. It is within the scope of the present invention that said NC-1 monomer comprises more than one endostatin-derived peptide or endostatin peptide, for example, two, three, four or even more peptides.

In preferred embodiments of the protein oligomer or peptide oligomer or fusion protein of the invention, the NC-1 monomer of the invention comprises or consists of the endostatin domain, as defined elsewhere herein. Preferably, the mentioned endostatin-derived peptide, endostatin peptide or endostatin domain carry a single mutation of glutamine to cysteine at position 7 of the endostatin domain. Such mutants are able to form disulfide bridges and are, thus, able to form dimers; see, e.g., Kuo 2001, *JCB* 152, 1233; Tjin et al. 2005, *Cancer Res* 65, 3656.

In a further embodiment, the NC-1 monomer of the invention comprises, in addition to the zinc binding site/domain of the endostatin domain, the endostatin-derived peptide, the endostatin peptide or the endostatin domain, a hinge region. Such a construct will probably form a monomer, possibly a dimer. The formation of a dimer cannot be excluded since it appears that the hinge region may also contribute to the dimer association of such constructs. Optionally, such an NC-1 monomer comprises, in addition, to the mentioned domain constituents an association domain, i.e. the non-triple helical trimerization domain of human collagen 18, or another oligomerization domain as referred to herein. It is evident to those skilled in the art that the presence of the association domain results in the formation of a trimer. In another aspect, the NC-1 monomer comprises an endostatin domain and an association domain of the above-defined NC-1 domain and, in a still further aspect, an association domain, a hinge region and an endostatin domain, each of said NC-1 domain. In the latter aspect, the NC-1 monomer comprises the complete NC-1 domain of human collagen 18 or is, i.e. consists of, the NC-1 domain of human collagen 18 (of about 38 kDa). The NC-1 domain of human collagen 18 and the structure of said NC-1 domain has been defined, e.g., by Sasaki et al. (loc. cit.). The NC-1 domain of collagen 18 consists of a non-triple-helical sequence of 315 (mouse) or 312 (human) amino acid residues. As set forth above, the NC-1 domain has been found to associate non-covalently to form a trimer via the above-mentioned association domain.

Oligomerization of NC-1 is mediated by at least two domains of this protein: one consisting of approximately 50 amino acids at the N-terminal of the protein defining a triple-helix structure, i.e. the association domain. The second domain which participates in oligomerization is located at the N-terminus of endostatin and is able to bind to zinc. The human endostatin zinc site is formed by histidines 1, 3 and 11 and aspartic acid 76. Said domain has been shown to form a dimer at high concentration of endostatin (Ding et al., loc. cit.). It is also possible that the protease sensitive hinge region plays a role in oligomerization of NC-1, as already indicated above. Accordingly, in some aspects of the invention, the NC-1 monomer can further comprise a hinge region of the NC-1 domain.

The NC-1 monomer of the invention is preferably longer than 20, 30, 40, 50, 60, 70, 80, 90, 100, 110, 120, 130, 140, 150, 160, 170, 180, 190, 200, 210, 220, 230, 240, 250, 260, 270, 280, 290, 300, or 310 amino acid residues. In case the NC-1 monomer comprises the association domain, the hinge region and the zinc binding site/domain of endostatin domain or the complete endostatin domain, it is preferred that the NC-1 monomer is longer than 312 amino acid residues and comprises even more preferred at least 315, 320, 330, 340, 350, 400, 500 or even more amino acid residues.

The term "oligomerization domain" as used herein refers generally to a protein domain which mediates the sub-unit assembly of the two or more NC-1 monomers, as defined herein. As indicated above, the oligomerization domain mediates dimerization, trimerization, and/or tetramerization and so on, of the NC-1 monomers. Such oligomerization leads, e.g., to functional advantages of multivalency and high binding strength, increased structure stabilization and combined functions of different domains, resulting in enhanced biological activity, such as improved or increased anti-angiogenic and/or anti-tumor activity. In one aspect, the oligomerization domain comprises the association domain of the NC-1 domain mentioned above, i.e. the non-triple helical trimerization domain of collagen 18 which is responsible for non-covalent oligomerization of the NC-1 monomers or the collagen 18 helices. In another aspect, the oligomerization domain can comprise other scaffold constructs/domains providing oligomerization and longer half life, well known in the art; see, e.g. Ali and Imperiali 2005, *Bioorganic and Medicinal Chemistry* 13, 5013. Such an oligomerization domain replaces structurally and functionally the association domain as found in the natural human NC-1 domain referred to above, or is used, in addition, to said association domain. In a further embodiment of the protein oligomer or fusion protein of the invention, the oligomerization is mediated by an Fc domain of an immunoglobulin, i.e. the oligomerization domain of the NC-1 monomer as defined herein comprises or is a Fc domain of an immunoglobulin. It is known in the art that fusion of a Fc domain to, e.g., a peptide or protein mediates a longer half life in circulation. It is to be understood that the Fc domain may be used in said NC-1 monomer, in addition, to the association domain of the NC-1 domain mentioned above (as shown, for instance in the following examples) or may replace the association domain. The Fc domain confers a dimeric structure on the NC-1 monomer as defined herein since Fc is a dimer itself. In another embodiment, the oligomerization can be mediated by the introduction of a structural modification, e.g., a mutation into the NC-1 monomer which results in the formation of disulfide bonds, as set forth in more detail below. It is further envisaged that the protein oligomers or peptide oligomers or fusion proteins of the invention can be formed covalently.

The invention further relates to a method for identifying the exact boundaries of the monomer, dimer and/or trimer transitions in the NC-1 domain as defined herein, the method comprising: a) generating a series of recombinant peptides from or derived from the NC-1 domain, starting with a peptide consisting of the endostatin domain, followed by increasing the size of said peptide consisting of the endostatin domain in steps of about 10 to 20 amino acid residues, and b) testing the recombinant peptides of step a) for their oligomerization properties, i.e. whether said peptides are able to form dimers or trimers and identifying peptides which are able to form oligomers, and c) determining the exact boundaries of the monomer, dimer and/or trimer transitions in the NC-1 domain. The method can comprise a further step d) of constructing an oligomer or fusion protein of the invention using the recombinant peptides identified in step b) which are able to form dimers or trimers. For generating a series of recombinant peptides from or derived from the NC-1 domain, peptide or protein synthesis known in the art can be used. The term "derived from" has been defined elsewhere herein and applies *Mutatis mutandis* to peptides derived from the NC-1 domain. For testing the oligomerization properties of said fragments, Western blot analysis, immunoprecipitation, SDS-PAGE, chromatographic methods or other methods well known in the art can be utilized. The recombinant peptides generated by the above-indicated method can be used to produce oligomers or fusion proteins, such as Fc fusion proteins, of the invention which can then further be tested for their anti-angiogenic and/or anti-tumor activity. The invention further pertains to the recombinant peptides from or derived from the NC-1 domain identified by such a method which show the biological activity as defined elsewhere herein, preferably anti-angiogenic and/or anti-tumor activity. An oligomer or fusion protein of the invention comprising such peptides is particularly useful as a pharmaceutical composition, as set forth elsewhere herein. The invention also relates to recombinant peptides from or derived from the NC-1 domain which are generated by increasing the size of the endostatin domain in steps of about 10 to 20 amino acid residues. Each of these peptides is a candidate for exploring their anti-angiogenic and/or anti-tumor activity by using in vitro and/or in vivo assays described elsewhere herein.

The "NC-1 monomer" of human collagen 18 as defined herein can comprise additional protein domains or subunits, for instance, the above-mentioned Fc domains of immunoglobulins, or protein tags, for example, His tags or the like, which can be used, e.g., for purification and/or detection. As well known in the art, protein tags are peptide sequences genetically grafted onto a recombinant protein. These tags can in one aspect be removable by chemical agents or by enzymatic means, such as proteolysis or intein splicing. Such tags are attached to the NC-1 monomer as referred to herein. Affinity tags are appended to proteins so that they can be purified from their crude biological source such as a cell lysate using an affinity technique well known in the art. These include, for example, chitin binding protein (CBP), maltose binding protein (MBP), Fc domains of immunoglobulins or glutathione-S-transferase (GST). The poly(His) tag is a widely-used protein tag; it binds to metal matrices. Solubilization tags are used, especially for recombinant proteins expressed in chaperone-deficient species such as E. coli, to assist in the proper folding in proteins and keep them from precipitating. These include, e.g., thioredoxin (TRX) and poly-(NANP). Some affinity tags have a dual role as a solubilization agent, such as MBP, and GST. Chromatography tags are used to alter chromatographic properties of the NC-1 monomer to afford different resolution across a particular separation technique. Often, these consist of polyanionic amino acids, such as the FLAG-tag. Epitope tags are short peptide sequences which are chosen because high-affinity antibodies can be reliably produced in many different species. These are usually derived from viral genes, which explain their high immunoreactivity. Epitope tags include, for instance, V5-tag, c-myc-tag, and HA-tag. These tags are useful, e.g., for western blotting and immunoprecipitation experiments, although they also find use in protein purification. Fluorescence tags are used to give visual readout on a protein. GFP and its variants are the most commonly used fluorescence tags. More advanced applications of GFP include using it as a folding reporter (fluorescent if folded, colorless if not). Protein tags find many other usages, such as specific enzymatic modification (such as biotin ligase tags) and chemical modification (Flash tag). The various tags can also be combined to produce multifunctional modifications of the NC-1 monomer. The NC-1 monomer of human collagen 18 as defined herein can also comprise radioisotopes, e.g. $^{124}$I $^{125}$I $^{131}$I, Cu-64, Cu-67, Y-86, Zr-89, Y-90, Re-188, Ga-68; or radionuclides binding to chelates such as DTPA; toxins, e.g. Diphtheria toxin, or apoptosis inducing agents; or chemicals, e.g. chemotherapies such as taxols, or gemcitabine, which may be useful in improving and/or detecting the anti-angiogenic activity of the protein oligomer or fusion protein of the invention. In other embodiments, the protein oligomer or fusion protein of the invention is pegylated. Pegylation is the process of covalent attachment of polyethylene glycol (PEG) polymer chains to another molecule, normally a drug or therapeutic protein. Pegylation is routinely achieved by incubation of a reactive derivative of PEG with the target macromolecule. The covalent attachment of PEG to a drug or therapeutic protein can "mask" the agent from the host's immune system (reduced immunogenicity and antigenicity), increase the hydrodynamic size (size in solution) of the agent which prolongs its circulatory time by reducing renal clearance. Pegylation can also provide water solubility to hydrophobic drugs and proteins. Pegylation of compounds is well known in the art; see, e.g., Damodaran and Fee 2010, *European Pharmaceutical Review* 15, 18.

The term "Fc region" or "Fc domain" as used herein means the fragment crystallizable region which is the tail region of an antibody or immunoblobulin that interacts with cell surface receptors, i.e. Fc receptors, and some proteins of the complement system. This property allows antibodies to activate the immune system. In IgG, IgA and IgD antibody isotypes, the Fc domain is composed of two identical protein fragments, derived from the second and third constant domains of the antibody's two heavy chains; IgM and IgE Fc domains contain three heavy chain constant domains (CH domains 2-4) in each polypeptide chain. The Fc domains of IgGs bear a highly conserved N-glycosylation site. Glycosylation of the Fc fragment is essential for Fc receptor-mediated activity. The N-glycans attached to this site are predominantly core-fucosylated diantennary structures of the complex type. In addition, small amounts of these N-glycans also bear bisecting GlcNAc and α-2,6 linked sialic acid residues. Fusion of the Fc domain of immunoglobulins to proteins has been found to enhance the production and secretion of the fusion proteins in mammalian cells (Lo et al., 1998, *Protein Eng* 11, 495, Capon et al., 1989, *Nature* 337, 525). In addition, linking of angiogenesis inhibitors to an immunoglobulin Fc domain have shown to increase the half life of said inhibitors (Capon et al. 1989, *Nature* 337, 525; Gordon et al., 2001, *J Clin Oncol* 19, 843; Holash et al., 2002, *Proc Natl Acad Sci USA* 99, 11393). However, the Fc domain can not only be used for purification, solubilization and/or detection purposes but alters advantageously the biological properties of the protein oligomer or fusion protein of the invention, as set forth herein below and in the following examples. In one embodiment, the one or more Fc domains can be cleaved off by treatment with proteases, such as enterokinase or thrombin, if desired. Preferably, the Fc domain as referred to herein is from human IgG (Bergers and Javaherian *Science* 1999; Lee et al *Clin Canc Res* 2008). As evident to those skilled in the art, in principle, any IgG isoform can be used to generate the oligomer or fusion protein of the invention. Even subfragments or single chains of the Fc domain of IgG can be used in order to prolong the half life or oligomerization of the oligomer or fusion protein of the invention. The amino acid sequences of a mouse and human Fc domain which can be used for the generation of an oligomer or a fusion protein of the invention, e.g. an Fc-NC-1 or NC-1-Fc fusion protein, are shown in SEQ ID NOs: 5 and 6, respectively.

The term "angiogenesis-related disease" as used herein denotes any disorder associated with abnormal blood vessel growth, either excessive or insufficient. The term "angiogenesis-related disease" is preferably selected from the group consisting of angiogenesis-dependent cancer including solid tumors, blood born tumors such as leukemias, melanomas, tumor metastases, benign tumors such as hemangiomas, acoustic neuromas, neurofibromas, trachomas, pyogenic granulomas; rheumatoid arthritis; psoriasis; ocular angiogenic diseases such as diabetic reintopathy, retinopathy of prematurity, macular degeneration, corneal graft rejection, neovascular glaucoma, retrolental fibroplasias, rubeosis; Osler-Webber syndrome; myocardial angiogenesis; plaque neovascularization; telangiectasia; hemophiliac joints; angiofibroma; wound granulation; diseases of excessive or abnormal stimulation of endothelial cells such as interstinal adhesions, atherosclerosis, scleroderma, hypertrophic scars (keloids); diseases that have angiogenesis as a pathologic consequence such as cat scratch disease (Rochele minalia quintosa) and ulcers (*Helobacter pylori*). Preferably, the angiogenesis-related disease as referred to herein is a melanoma.

The term "treatment" as used herein denotes the improvement or even elimination of one or more symptoms associated with the angiogenesis-related disease as referred to herein, by the administration of a protein oligomer or peptide oligomer or fusion protein of the invention. An improvement may also be seen as a slowing or stopping of the progression of the angiogenesis-related disease as set forth herein.

The term "prevention" as used herein means the avoidance of the occurrence or re-occurrence of an angiogenesis-related disease as specified herein, by the administration of a protein oligomer or peptide oligomer or fusion protein of the invention.

It has unexpectedly been found by the present inventors that trimeric NC-1 (with NC-1 comprising the association domain, the hinge region and the endostatin domain) derived from human collagen 18 binds fibronectin, whereas endostatin monomer lacks binding to fibronectin. Fibronectin is recognized as a major extracellular matrix protein, binding angiogenic and anti-angiogenic reagents. Endostatin is a monomer under physiological conditions. The major precursor to endostatin is NC-1, a trimeric molecule consisting of three interlinked chains, each with approximately 330 amino acids. This shows that NC-1 trimer has distinct properties in comparison to endostatin. Furthermore, an Fc-endostatin which forms dimers as well as an artificial endostatin dimer bearing a single mutation in amino acid position 7 (glutamine to cysteine) of endostatin retains binding to fibronectin indicating the importance of oligomerization for binding to fibronectin. Following a search for endostatin-size molecules in human sera, the inventors failed to identify the conventional size endostatin (of about 20 kDa). The appearance of endostatin size molecules in human blood circulation might be due to the degradation of NC-1 trimer by proteases following collection of human sera. NC-1 trimer appeared to be the major physiological product of collagen 18 degradation, present in tissues and circulation showing distinct biological properties not shared by (monomeric) endostatin. The inventors further demonstrated high affinity binding of fibronectin to VEGF, NC-1 trimer as well as co-immunoprecipitated these three candidate interaction partners from peripheral blood platelets protein lysates. Furthermore, in-vivo co-localization of NC-1 trimer, Fibronectin, VEGF and alpha 5 beta 1 ($\alpha5\beta1$) integrin could be demonstrated, suggesting a model in which an ensemble of VEGF, NC-1 trimer, integrin $\alpha5\beta1$ with fibronectin prelude the initiation of the anti-angiogenic process. Most importantly, antitumor studies of NC-1 trimer versus endostatin showed that NC-1 trimer is a more potent anti-angiogenic protein than endostatin. The above data are specified in more detail in the following examples.

In one embodiment of the protein oligomer of the invention, the NC-1 monomer of human collagen 18 comprises an (i) oligomerization domain, (ii) a hinge region and/or (iii) endostatin domain or a fragment of said endostatin domain and, optionally recombinant protease cleavage site within the hinge region. Preferably, said fragment of the endostatin domain is a peptide comprising the zinc binding site/domain of endostatin.

In another preferred embodiment of the protein oligomer of the invention, the hinge region is interposed between the oligomerization domain and the endostatin domain. Preferably, the hinge region is located between the oligomerization domain and the zinc binding site/domain of endostatin or endostatin domain in the NC-1 monomer as referred to herein. The domain arrangement within the NC-1 monomer of human collagen 18 is preferably oligomerization domain-hinge region-endostatin domain, or endostatin domain-hinge region-oligomerization domain.

Optionally, the hinge region within the NC-1 monomer of human collagen 18 may comprise one or more recombinant protease cleavage sites, in addition to the endogenous protease cleavage sites of the hinge region. Such a recombinant protease cleavage site can be, for instance, an enterokinase or thrombin cleavage (Bergers and Javaherian; Lee et al.; loc. cit.). Cleavage by the respective protease allows for, e.g., the release of the endostatin domain(s) of the protein oligomer or fusion protein of the invention.

In a preferred embodiment of the protein oligomer or peptide oligomer or fusion protein of the invention, the oligomerization domain comprises a non-triple helical trimerization domain of human collagen 18 (i.e. the association domain), an Fe domain and/or an artificial oligomerization domain. The oligomerization domain comprises in one aspect a non-triple helical trimerization domain of human collagen 18 which is responsible for trimerization of the three chains of the NC-1 domain. In another aspect, it comprises an Fe domain. The Fc domain confers a dimeric structure on the NC-1 monomer as defined herein since the Fe domain is a dimer itself. In a third aspect, it comprises an artificial oligomerization domain, for example, cysteins resulting in disulfide bridges between two monomers which replaces structurally and functionally the association domain as found in the natural human NC-1 referred to above, or is used in addition to said association domain. It is also encompassed by the scope of the invention, that the oligomerization domain of the protein oligomer or fusion protein of the invention comprises a non-triple helical trimerization domain of human collagen 18 and a Fc domain. Further, it can comprise an artificial oligomerization domain and a Fe domain.

Preferably, the Fc domain is from IgG or other immunoglobulin isoforms as well as other scaffold constructs providing oligomerization and longer half life described in the art; see, e.g., Lo et al Protein Enginerring 1998, 11, 495. A murine Fc domain is shown, for example, in SEQ ID NO: 5. More preferably, the Fe domain is from a human IgG, even more preferred from human IgG1. Particularly preferred, the human Fe domain comprises or consists of an amino acid sequence as shown in SEQ ID NO: 6.

The oligomerization domain of the NC-1 monomer can be a Fc domain of an immunoglobulin, preferably a Fc domain from IgG1, as set forth above. The protein oligomer or peptide oligomer or fusion protein of the invention can also contain two, three or even more Fc domains. In one aspect, the Fc domain(s) may be cleaved off the protein oligomer or peptide oligomer or fusion protein of the invention, if desired. For instance, an artificial protease cleavage site such as an enterokinase or a thrombin cleavage site can be interposed between the NC-1 monomer and the Fc domain(s) in the protein oligomer or peptide oligomer of the invention, for example, via a corresponding (poly)peptide linker. Upon cleavage by the respective protease, the oligomer is released from the Fc domain(s). The Fc domain(s) can be used for purification and/or detection. In addition, the Fc domain alters the biological properties of the protein oligomer or fusion protein of the invention, such as half-life extension in circulation and improvement of biological activity, preferably improvement of anti-angiogenic activity. For example, it has been found that an Fc-endostatin fusion protein is able to bind fibronectin as a dimer, whereas endostatin monomer does not. Moreover, Fc-endostatin shows a longer half-life than endostatin.

In a further preferred embodiment of the protein oligomer or peptide oligomer or fusion protein of the invention, the artificial oligomerization domain comprises a single muta- tion at position 7 of the endostatin domain in which gluta- mine is replaced by cysteine. Preferably, the monomer as defined herein comprises in some aspects a single mutation of glutamine to cysteine at position 7 of the endostatin domain. For example, it has been found that a recombinantly introduced enterokinase cleavage site between the Fc domain and endostatin domain in a fusion protein results in the formation of a dimer upon enterokinase cleavage because of disulfide bond formation between adjacent C7 residues in the endostatin domains; see Kuo 2001, *JCB* 152, 1233. As set forth above, NC-1 trimer and endostatin dimers have distinct properties, in comparison to the endostatin monomer. The above mutation at position 7 (glutamine to cysteine) can also be introduced in the N-terminal peptide of endostatin which has been shown to represent the antitumor domain of endostatin (Tjin et al. 2005, *Cancer Res* 65, 3656). The oligomerization of the peptide can be achieved by either artificial dimerization as described above or simply by recombinant fusion to the Fc moiety without a mutation in position 7. An example for a fusion protein of the invention comprising said mutation at position 7 mediating dimerization is shown in SEQ ID NO: 15; see Example 2.10.

In another preferred embodiment of the protein oligomer or peptide oligomer of the invention, the recombinant pro- tease cleavage site within the hinge region is an enterokinase or thrombin cleavage site. The cleavage of the protein oligomer or peptide oligomer with the enterokinase or thrombin results in the release of the endostatin domains from the protein oligomer or peptide oligomer of the inven- tion.

In a further preferred embodiment of the protein oligomer or peptide oligomer of the invention, the NC-1 monomer as defined herein contains only protease cleavage sites natu- rally occurring within the hinge region, i.e. it does not comprise a recombinant protease cleavage site. In this case, the hinge region can be cleaved, e.g. by MMPs, as set forth elsewhere herein, in order to release, e.g., the endostatin domain(s). In another aspect, these naturally occurring pro- tease cleavage sites in the hinge region of the NC-1 mono- mer can be mutated so that NC-1 monomer is no longer cleaved by said proteases. In this way, the anti-angiogenic activity of the protein oligomer of the invention may still be improved.

In another embodiment of the protein oligomer or peptide oligomer of the invention, the angiogenesis-related disease to be treated is selected from the group consisting of angiogenesis-dependent cancer including solid tumors, melanomas, tumor metastases, blood born tumors such as leukemias, benign tumors such as hemangiomas, acoustic neuromas, neurofibromas, trachomas, pyogenic granulomas; rheumatoid arthritis; psoriasis, ocular angiogenic diseases such as diabetic retinopathy, retinopathy of prematurity, macular degeneration, corneal graft rejection, neovascular glaucoma, retrolental fibroplasias, rubeosis, Osler-Webber syndrome; myocardial angiogenesis; plaque neovasculariza- tion; telangiectasia; hemophiliac joints; angiofibroma, wound granulation, diseases of excessive or abnormal stimulation of endothelial cells such as intestinal adhesions, atherosclerosis, scleroderma, hypertrophic scars (keloids), diseases that have angiogenesis as a pathologic consequence such as cat scratch disease (Rochele minalia quintosa) and ulcers (*Helobacter pylori*). Preferably, the angiogenesis- related diseases are renal cell carcinoma, colorectal-, pros- tate-, breast- or lung cancer.

The protein oligomer or peptide oligomer or fusion pro- tein of the invention is preferably formulated as a pharma- ceutical composition which can be administered by standard routes. Generally, the pharmaceutical composition may be administered by the topical, transdermal, intraperitoneal, intracranial, intracerebroventricular, intracerebral, intravagi- nal, intrauterine, oral, rectal or parenteral (e.g. intravenous, intraspinal, subcutaneous or intramuscular) route.

A pharmaceutical composition comprising the protein oligomer or peptide oligomer or fusion protein of the invention as pharmaceutical active compound may be used for non-human or preferably human therapy of various angiogenesis-related diseases or disorders as specified else- where herein in a therapeutically effective dose. In an aspect, the protein oligomer or peptide oligomer or fusion protein of the invention can be present in liquid or lyophilized form. In an aspect, the protein oligomer or peptide oligomer or fusion protein can be present together with glycerol, protein stabi- lizers (e.g., human serum albumin (HSA)) or non-protein stabilizers.

The compound (i.e. the protein oligomer or peptide oli- gomer or fusion protein of the invention) is the active ingredient of the pharmaceutical composition, and is in one aspect, administered in conventional dosage forms prepared by combining the drug with standard pharmaceutical carriers according to conventional procedures. These procedures may involve mixing, granulating, and compression, or dis- solving the ingredients as appropriate to the desired prepa- ration. It will be appreciated that the form and character of the pharmaceutical acceptable carrier or diluent is dictated by the amount of active ingredient with which it is to be combined, the route of administration, and other well-known variables.

The carrier(s) must be acceptable in the sense of being compatible with the other ingredients of the formulation and being not deleterious to the recipient thereof. The pharma- ceutical carrier employed may include a solid, a gel, or a liquid. Exemplary of solid carriers are lactose, terra alba, sucrose, talc, gelatine, agar, pectin, acacia, magnesium stear- ate, stearic acid and the like. Exemplary of liquid carriers are phosphate buffered saline solution, syrup, oil, water, emul- sions, various types of wetting agents, and the like. Simi- larly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pennsylvania.

The diluent(s) is/are selected so as not to affect the biological activity, preferably, anti-angiogenic activity of the combination. Examples of such diluents are distilled water, physiological saline, Ringer's solutions, dextrose solution, and Hank's solution. In addition, the pharmaceutical com- position or formulation may also include other carriers, adjuvants, or non-toxic, non-therapeutic, non-immunogenic stabilizers and the like.

A therapeutically effective dose refers to an amount of the protein oligomer or peptide oligomer or fusion protein of the invention to be used in a pharmaceutical composition which prevents, ameliorates or treats the symptoms accompanying an angiogenesis-related disease or condition referred to in this specification. Therapeutic efficacy and toxicity of the compound can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment.

The medicament referred to herein is administered at least once in order to treat or ameliorate or prevent a disease or condition recited in this specification. However, the said medicament may be administered more than one time.

Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent. The resulting formulations are to be adapted to the mode of administration. Dosage recommendations shall be indicated in the prescribers or users instructions in order to anticipate dose adjustments depending on the considered recipient.

The pharmaceutical composition may in a further aspect of the invention comprise drugs in addition to the protein oligomer of the invention which are added to the medicament during its formulation. Finally, it is to be understood that the formulation of a pharmaceutical composition takes place under GMP standardized conditions or the like in order to ensure quality, pharmaceutical security, and effectiveness of the medicament.

In another preferred embodiment of the protein oligomer or peptide oligomer of the invention, the oligomer is a dimer or a trimer. However, encompassed by the protein oligomer of the invention are also tetramers or pentamers or oligomers with even more NC-1 monomers as defined herein.

The invention also relates to a method for producing the protein oligomer or peptide oligomer or fusion protein of the invention, comprising (a) culturing a host cell comprising a nucleic acid encoding the protein oligomer or peptide oligomer or fusion protein of the invention, preferably under serum-free conditions, (b) obtaining from the host cell of step (a) the protein oligomer or peptide oligomer or fusion protein, and, optionally, (c) storing the protein oligomer or peptide oligomer or fusion protein, preferably under serum-free conditions. As shown in the following examples, it has been found by the present inventors, that oligomeric NC-1 such as the NC-1 trimer is susceptible to degradation if kept in serum or cell culture media for longer periods of time, even at 4° C. Therefore, it is advantageous to produce and keep the protein oligomer or peptide oligomer of the invention under serum-free conditions.

Furthermore, the invention pertains to a method for the identification of an anti-angiogenic agent, comprising (a) contacting the protein oligomer or peptide oligomer of the invention with fibronectin and/or VEGF under conditions which allow binding of the protein oligomer or peptide oligomer of the invention to fibronectin and/or VEGF to form a complex, (b) contacting the complex of step a) with a panel of agents, (c) identifying and isolating those agents which are capable of binding to the complex of step (a), and (d) testing of the anti-angiogenic activity of the agent identified in step c) in an in vitro assay.

The method of the present invention can be assisted by automation. Specifically, in an aspect, step a) and/or b) and/or c) may be assisted by robotic devices and automated reader systems for mixing compounds and measuring the complex formation. Suitable systems are known in the art and depend on the type of response to be determined. Moreover, the method may comprise additional steps pertaining to the generation of the protein oligomer or peptide oligomer of the present invention.

The term "contacting" as used herein refers to bringing at least two different compounds in physical proximity as to allow physical and/or chemical interaction of said compounds. In the aforementioned method, the protein oligomer or peptide oligomer according to the present invention is first contacted with fibronectin and/or VEGF to form a complex. Thereafter, said complex is contacted with a panel of agent, e.g. a protein, peptide, chemical or aptamer library suspected to comprise a biologically active polypeptide. The protein oligomer or peptide oligomer of the invention shall be contacted with the mentioned compounds for a time and under conditions sufficient to allow complex formation. Contacting as used herein, in an aspect, occurs in a host cell containing the protein oligomer or peptide oligomer of the present invention. The said time and conditions will be dependent on the amount of protein oligomer or peptide oligomer. The person skilled in the art is well aware of which conditions need to be applied dependent on the host cell and kind of protein oligomer or peptide oligomer. In another aspect, contacting occurs in a cell free system comprising the protein oligomer or peptide oligomer of the invention. The cell free system shall allow for the complex formation of the protein oligomer or peptide oligomer and the compounds mentioned above. In vitro assays for testing anti-angiogenic activity have been set forth elsewhere herein.

Furthermore, the invention relates to a kit comprising the protein oligomer or peptide oligomer of the invention.

The term "kit" as used herein refers to a collection of means comprising the protein oligomer or peptide oligomer of the present invention which are provided in separate or common vials in a ready to use manner for carrying out the treatment of an angiogenesis-related disease as defined herein. In an aspect, the kit comprises additional means for carrying out the treatment of an angiogenesis-related disease, in an aspect, further anti-angiogenic agents which can be used in combination with the protein oligomer or peptide oligomer of the invention, such as antibodies against or small molecular kinase inhibitors to, in particular, IGF1R, c-Met, Pi3K, VEGFR, Braf, ALK-EML4, PDGFR, antagonizing antibodies against key cytokines such as CCL2, GM-CSF/CSF, Bv8, SDF1, and standard anticancer treatments such as radiotherapy and chemotherapies. Furthermore, in an aspect, the kit comprises instructions for carrying out the treatment of an angiogenesis-related disease. These instructions can be provided as a manual or can be in the form of a computer-implementable algorithm on a data storage medium which upon implementation is capable of governing one or more steps of the treatment of an angiogenesis-related disease. The instructions comprise information with respect to the dosage of the protein oligomer or peptide oligomer of the invention, time and mode of administration and the like. In an aspect, the kit is to be used for carrying out the treatment of a specific angiogenesis-related disease listed herein above, e.g. angiogenesis-related cancer.

The present invention further pertains to a fusion protein comprising a NC-1 monomer of human collagen 18 and a Fe domain of an immunoglobulin.

The terms "protein", "peptide", "NC-1 monomer" (of human collagen 18), and "Fc domain or Fc region" (of an immunoglobulin) have been defined elsewhere herein. Said definitions and the embodiments of the NC-1 monomer set forth elsewhere herein apply *Mutatis mutandis* to the fusion proteins of the invention.

The term "fusion protein" as used herein denotes a polypeptide comprising at least one NC-1 monomer as defined herein linked to at least one Fc domain derived from an immunoglobulin. Preferably, the fusion protein is human. The Fc domain can be fused either to the N-terminus or the C-terminus of the NC-1 monomer, preferably to the N-terminus.

In a preferred embodiment of the fusion protein of the invention, the fusion protein comprises an oligomerization domain, a hinge region and/or an endostatin domain and, optionally a recombinant protease cleavage site within the hinge region. The generation and expression of such an Fc-NC-1 fusion protein is shown in the following examples. In case the fusion protein of the invention comprises an association domain as defined herein and an Fe domain, it can be beneficial to use a Fc domain lacking the single disulfide bridge. The removal of the disulfide bridge may be beneficial for the following reason: Fc is a dimer, whereas NC-1 is a trimer which means that a dimer needs to attach to a trimer. Therefore, it can be helpful to construct a NC-1-Fc fusion protein which is missing the single disulfide present on Fc to prevent dimer formation of the Fc in order to avoid, for example, poor expression of the protein. This can be achieved, for example, by mutating the cysteines at the N terminus in the Fc domain (for example, the cysteine amino acid residues 11 and 14 of the human Fc domain shown in SEQ ID NO: 6) to alanine. It is expected that this approach will provide for a trimer Fc-trimer NC-1 construct, as a result of NC-1 trimerization mediated by the non-triple helical trimerization domain. In other aspects, the fusion protein can, for example, comprise an oligomerization domain and an endostatin domain. It can further comprise a hinge region, optionally with a recombinant protease cleavage site. Alternatively, it can comprise a hinge region and an endostatin domain.

In another preferred embodiment of the fusion protein of the invention, the oligomerization domain comprises a non-triple helical winterization domain of human collagen 18 and/or an artificial oligomerization domain and/or other above-mentioned mechanisms for oligomerization of the monomer.

Preferably, the Fc domain (as shown, for example, in SEQ ID NO: 5 or 6) is from IgG. In one aspect, the NC-1 monomer as defined herein is fused to the one or more Fc domains via a (poly)peptide linker. For instance, a NC-1 monomer can be fused to the Fc portion of human IgG through a poly Glycine (poly Gly) linker.

In a further preferred embodiment of the fusion protein of the invention, the oligomerization domain comprises a single mutation at position 7 of the endostatin domain in which glutamine is replaced by cysteine.

In one embodiment, the hinge region is interposed between the Fc domain and the endostatin domain in the NC-1 monomer as referred to herein. Said hinge region can comprise a recombinant protease cleavage site such as an enterokinase or thrombin cleavage site. Optionally, the hinge region within the NC-1 monomer of collagen 18 may comprise one or more recombinant protease cleavage sites, in addition to the endogenous protease cleavage sites, e.g. for MMPs, of the hinge region.

In another preferred embodiment of the fusion protein of the invention, the domain arrangement of the fusion protein is Fc domain—oligomerization domain—hinge region—endostatin domain or oligomerization domain—hinge region—endostatin domain—Fc domain or Fc domain—endostatin domain—hinge region—oligomerization domain or endostatin domain—hinge region—oligomerization domain—Fc domain. It is preferred that the domain arrangement of the fusion protein mediates oligomerization of the endostatin monomer over disulfide bound between the two Fc-fragments.

In a still further preferred embodiment of the fusion protein of the invention, the fusion protein lacks the association domain of the NC-1 domain, i.e. it comprises the Fc domain as an oligomerization domain.

In addition to the protein oligomer of the invention, an Fc-NC-1 fusion protein comprising a NC-1 monomer and a Fc domain of an immunoglobulin has recently been constructed and will be tested for anti-angiogenic activity and/or antitumor activity and longer half-life. It is expected that such a fusion protein will exhibit a still longer half-life and/or still improved anti-angiogenic activity than the protein oligomer of the invention.

In one embodiment of the fusion protein, said fusion protein is a protein oligomer, preferably a dimer, trimer or tetramer. The term "protein oligomer" has been defined elsewhere herein. The definitions and embodiments of the protein oligomer of the invention apply *Mutatis mutandis* to the fusion protein of the invention, comprising said NC-1 monomer as defined herein and an Fc domain of an immunoglobulin. It is encompassed within the scope of the invention that said fusion protein can comprise more than one NC-1 monomer as defined herein, e.g. two, three, four or even more monomers. In such embodiments, the fusion protein of the invention is being used as an oligomer. Moreover, said fusion protein can comprise more than one Fc domain, e.g., two, three, four or even more Fc domains.

In a preferred embodiment of the fusion protein of the invention, the hinge region in the fusion protein of the invention comprises a structural modification, e.g. one or more mutation(s), in a MMP protease cleavage site conferring decreased cleavage by said MMP protease.

The invention pertains also to a fusion protein comprising:
- a) an endostatin peptide or endostatin-derived peptide; and
- b) the RGD motif and/or PHSRN motif (SEQ ID NO:20) of Fibronectin.

The definitions and embodiments with respect to the protein oligomer or peptide oligomer or fusion protein (comprising a NC-1 monomer and a Fc domain) of the invention apply *Mutatis mutandis* to a fusion protein of the invention comprising the features a) and b) set forth above.

The "endostatin peptide" or "endostatin-derived peptide" such as the N-terminal zinc-binding domain of endostatin or a synthetic peptide corresponding to the N-terminal zinc-binding domain of endostatin have been described elsewhere herein and are shown in detail in the following Examples; see, for instance, the amino acid sequences of SEQ ID NOs. 9 and 10. It is encompassed by the present invention, that variants of the amino acid sequences of SEQ ID NOs. 9 and 10, e.g., shorter amino acid sequences of SEQ ID NOs. 9 and 10 can be used as well. For example, the present inventors have found that a peptide corresponding to positions 1 to 13 of SEQ ID NO: 9 or positions 1 to 12 of SEQ ID NO: 10 can be used as endostatin peptide in the above-indicated fusion protein of the invention. In addition, such a peptide can differ from the corresponding endostatin peptide or endosta-tin-derived peptide in one, two, three, four or even more amino acid residues, while at least maintaining (or even exceeding) the biological activity (as described elsewhere herein) of the corresponding endostatin peptide in the endostatin domain of NC-1. In light of this, it is important to maintain the Histidine amino acid residues corresponding to positions 1, 3 and/or 11 of SEC) ID NOs. 9 or 10 for the reasons set forth elsewhere herein. Examples of endostatin peptides exhibiting anti-angiogenic and/or anti-tumor activ-ity which can be used in the fusion proteins or oligomers of the present application have been further described, e.g., in Tjin et al., loc. cit., or in U.S. Pat. No. 7,524,811.

Similarly, the RGD motif and/or PHSRN motif (SEQ ID NO:20) within Fibronectin (FN) have been mentioned else-where herein and are further characterized in the following Examples. For instance, SEQ ID NOs. 11 and 12 provide amino acid sequences comprising the RGD motif and sur-rounding amino acid residues important for binding of Fibronectin to integrins. Briefly, Fibronectin is recognized by integrins alpha 5 beta 1 and alpha V beta 3. The primary sequence motif of fibronectin for integrin binding is a tripeptide, Arg-Gly-Asp (RGD), located on the loop con-necting the force-bearing G- and F-strands of FN-III10.

Further involved in integrin binding of fibronectin is the Pro-His-Ser-Arg-Asn (PHSRN, SEQ ID NO:20) motif which resides in the ninth domain of type III fibronectin. The corresponding amino acid sequences of murine and human Fibronectin (FN) are shown, e.g., in accession numbers NP_034363.1 and NP_997647.1, respectively. The domain structure of human FN can be derived, e.g., from the publication by Wijelath et al. 2006, Circ. Res. 99, 853-860. Preferably, the RGD motif of Fibronectin comprises or consists of SEQ ID NO. 11, 12 or 17.

Preferably, the endostatin peptide or endostatin-derived peptide is located at the amino-terminal end of the fusion protein and the RGD motif and/or PHSRN motif (SEQ ID NO:20) of Fibronectin is located at the carboxy-terminal end of the fusion protein of the invention.

Preferably, this fusion protein of the invention comprises an amino acid sequence as shown in SEQ ID NO: 7 or 13.

In another preferred embodiment of this fusion protein of the invention, the fusion protein further comprises an Fc domain or an artificial oligomerization domain as defined herein. Preferably, the fusion protein with an artificial oli-gomerization domain comprises an amino acid sequence as shown in SEQ ID NO: 15.

Figure 10:
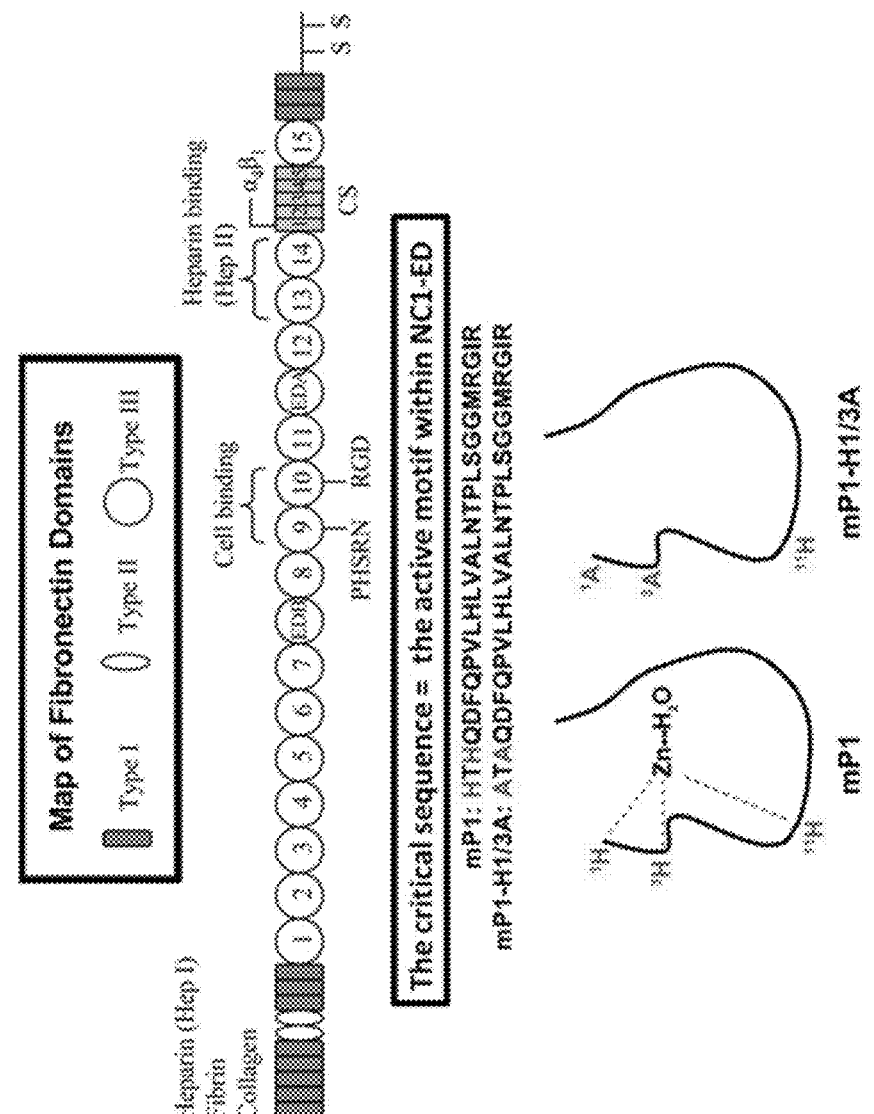

Based on the experimental data shown in the following Examples, the present inventors hypothesized that oligo-meric NC-1 may elicit its effects via fibroncectin (FN) binding via interference with at least two pivotal angiogen-esis pathways, i.e., VEGF and integrin alpha 5 beta 1 (ITGA5B1) signaling. Moreover, they found that FN is significantly down-regulated in tumors that become resistant to oligomeric NC-1 (Fc-Endostatin) after prolonged expo-sure, i.e. four serial in-vivo passages. Therefore, they pos-tulated that loss of FN might constitute a key mechanism of inherent and acquired resistance to oligomeric NC-1. To proof this concept, a minimal peptide sequence has been engineered that mimics the key effects of the endostatin (ED)—fibronectin complex. To this end, the inventors first selected the most active motif in the entire ED-domain consisting of a 27 amino acid-NH2-terminal region (Tjin Tham Sjin et al. 2005, Cancer Res. 65, 3656-63). Prelimi-nary data by the present inventors indicate that this region itself may be capable of binding to VEGF and that the two histidines (Zinc binding domain) in this peptide sequence may be critical for VEGF binding. This is conceivable, because a mutated peptide in which Histidines were replaced by Alanine residues failed to compete with VEGF-ED-dimer (Fc-Endostatin) binding. On the other hand, fibronectin contains two active motifs that are critical for its binding to ITGA5B1, i.e. a PHSRN-(SEQ ID NO:20) and a RGD-dependent motif. FIG. 10 shows a schematic overview of critical motifs within the ED-domain and FN. In order to mimic the physiological complex of oligomeric NC-1 and FN that mediated integrin signaling and other properties of the NC-1-ED, the inventors fused these two critical motifs, i.e. the above-mentioned most active motif in the NC-1-ED domain and the integrin-binding motif of fibronectin com-prising "RGD" and surrounding amino acid residues impor-tant for binding, and generated hybrid fusion proteins called "Superstatins". For each fusion protein, a mouse and a human equivalent was designed, as described in more detail below and in Example 2.10. Using the murine (C57BL6) LLC (Lewis lung carcinoma) lung cancer model, the inven-tors were able to show the efficacy of the murine Superstatin peptide to potently inhibit tumor growth; see FIG. 11. In addition, Superstatin significantly prolonged survival as compared to control. In contrast, the FN-Motif alone showed no significant improvement in prevention of tumor growth.

The corresponding amino acid sequence for the murine (m) Superstatin is shown in SEQ ID NO: 7, whereas the corresponding amino acid sequence for the human (h) Superstatin is shown in SEQ ID NO: 13. Superstatins are likely monomers. SEQ ID NO: 15 shows a variant of the human Superstatin amino acid sequence which is able to dimerize, due to the substitution of Glutamine at position 7 in SEQ ID NO: 13 by Cysteine. This fusion protein of the invention will allow analyzing the impact of dimerization on antitumor activity. Additional constructs containing the PHSRN (SEQ ID NO:20) instead of the RGD motif of FN, as well as constructs facilitating dimerization of the Super-statin via disulfide bounds or Fc regions are currently in preparation or already under in-vivo evaluation. The human Superstatin peptide (SEQ ID NO: 13) is conjugated to the complexing agent 1,4,7,10-tetraazacyclododecane-1,4,7,10-tetraacetic acid (also known as DOTA) providing the ability to conjugate the peptide with, e.g., radionuclides such as Gallium ($^{68}$Ga) for non-invasive imaging (Positron emission tomography, PET). The inventors check currently if DOTA conjugation is affecting the efficacy of the human Supersta-tin peptide in-vivo in a BxPC3 human pancreatic cancer model. In case this experiment confirms the activity of the Superstatin-DOTA constructs, in-vivo PET-Imaging evalu-ating the potential of Superstatin-DOTA as diagnostic agent is envisioned; see Example 2.10.

Accordingly, the invention further pertains to a fusion protein comprising a) an endostatin peptide or an endostatin-derived peptide and b) the RGD motif and/or PHSRN motif (SEQ ID NO:20) of Fibronectin for use as a diagnostic composition. Preferably, the human Superstatin peptide (SEQ ID NO: 13) is conjugated to the complexing agent 1,4,7,10-tetraazacyclododecane-1,4,7,10-tetraacetic acid (also known as DOTA).

In another preferred embodiment of this fusion protein of the invention, the fusion protein can be used to identify and/or characterize the region of fibronectin which binds to endostatin. Such methods are known in the art, see, e.g., BiaCore.

Further embodiments of the fusion proteins of the invention can be derived from the following Examples.

The invention further relates to a polynucleotide encoding the fusion proteins of the invention.

The term "polynucleotide" as used herein refers to single- or double-stranded DNA molecules as well as to RNA molecules. Encompassed by the said term is genomic DNA, cDNA, hnRNA, mRNA as well as all naturally occurring or artificially modified derivatives of such molecular species. The polynucleotide may be in an aspect a linear or circular molecule. Moreover, in addition to the nucleic acid sequences encoding the fusion protein of the present invention, a polynucleotide of the present invention may comprise additional sequences required for proper transcription and/or translation such as 5'- or 3'-UTR sequences. The nucleic acid sequences encoding the fusion protein of the present invention can be derived from the amino acid sequence envisaged for the fusion protein of the invention by a skilled artisan without further ado. In light of the degeneracy of the genetic code, optimized codons may be used in the nucleic acid sequences encoding the fusion protein in the polynucleotide of the present invention. Thereby, optimal expression in, e.g., a host cell of the present invention can be achieved.

It will be understood that the present invention also encompasses variants of such specific amino acid sequences of the fusion protein of the invention or nucleic acid sequences encoding them as long as these variant sequences also allow for the formation of a fusion protein of the invention. Said variants have preferably anti-angiogenic activity as defined elsewhere herein. In an aspect, a sequence variant as used herein differs from the specific amino acid sequence or a specific nucleic acid sequence as specified before by one or more amino acid or nucleotide substitutions, additions and/or deletions. In another aspect, the said variant sequence is at least 50%, at least 60%, at least 70%, at least 80%, at least 90%, at least 95%, at least 96%, at least 97%, at least 98% or at least 99% identical to the specific sequence of the fusion protein of the invention over the entire length or over at least a stretch of half of the length of the specific sequence. The term "identical" as used herein refers to sequence identity characterized by determining the number of identical amino acids between sequences wherein the sequences are aligned so that the highest order match is obtained. It can be calculated using published techniques or methods codified in computer programs such as, for example, BLASTP or FASTA (Altschul 1990, *J Mol Biol* 215, 403). The percent identity values are, in one aspect, calculated over the entire amino acid sequence or over a sequence stretch of at least 50% of the query sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, *CABIOS* 5, 151) or the programs Gap and BestFit (Needleman 1970, *J Mol Biol* 48; 443; Smith 1981, *Adv Appl Math* 2, 482), which are part of the GCG software packet (Genetics Computer Group 1991, 575 Science Drive, Madison, Wisconsin, USA 53711), may be used. The sequence identity values recited above in percent (%) are to be determined, in another aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

The invention further relates to a vector comprising the polynucleotide of the invention.

Preferably, the vector is an expression vector.

The term "vector" encompasses preferably phage, plasmid, viral or retroviral vectors as well as artificial chromosomes, such as bacterial or yeast artificial chromosomes. Moreover, the term also relates to targeting constructs which allow for random or site-directed integration of the targeting construct into genomic DNA. Such target constructs, in an aspect, comprise DNA of sufficient length for either homologous or heterologous recombination as described in detail below. The vector encompassing the polynucleotides of the present invention, in an aspect, further comprises selectable markers for propagation and/or selection in a host cell. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/ cells.

Moreover, in an aspect of the invention, the polynucleotide is operatively linked to expression control sequences allowing expression in prokaryotic or eukaryotic host cells or isolated fractions thereof in the said vector. Thus, in an aspect, the vector is an expression vector. Expression of the polynucleotide comprises transcription of the polynucleotide into a translatable mRNA. Regulatory elements ensuring expression in host cells are well known in the art. In an aspect, they comprise regulatory sequences ensuring initiation of transcription and/or poly-A signals ensuring termination of transcription and stabilization of the transcript. Additional regulatory elements may include transcriptional as well as translational enhancers. Possible regulatory elements permitting expression in prokaryotic host cells comprise, e.g., the lac-, trp- or tac-promoter in *E. coli*, and examples for regulatory elements permitting expression in eukaryotic host cells are the AOX1- or the GAL1-promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector encompassed by the present invention. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (Invitrogen) or pSPORT1 (Invitrogen). Preferably, said vector is an expression vector and a gene transfer or targeting vector. Expression vectors derived from viruses such as retroviruses, vaccinia virus, adeno-associated virus, herpes viruses, or bovine papilloma virus, may be used for delivery of the polynucleotide or vector of the invention into a targeted cell population. Methods which are well known to those skilled in the art can be used to construct recombinant viral vectors; see, for example, the techniques described in Sambrook, Molecular Cloning A Laboratory Manual, Cold Spring Harbor Laboratory (2001) N.Y. and Ausubel, Current Protocols in Molecular Biology, Green Publishing Associates and Wiley Interscience, N.Y. (1994).

The invention further relates to a host cell comprising the polynucleotide or the vector of the invention.

The term "host cell" as used herein as used herein encompasses prokaryotic and eukaryotic host cells. In an aspect the host cell is a bacterial cell. In one aspect, the said bacterial host cell is an *E. coli* host cell. Such a bacterial host cell may be used, e.g., for reproduction of the polynucleotide or the vector of the present invention.

A eukaryotic host cell, in an aspect, is a cell which comprises the fusion protein and either the polynucleotide or the vector of the present invention wherein said polynucleotide or vector are expressed in the host cell in order to generate the fusion protein. The polynucleotide may be introduced into a host cell either transiently or stably. In an aspect, the eukaryotic host cell may be a cell of a eukaryotic host cell line which stably expresses the polynucleotide of the invention. In another aspect, the host cell is a eukaryotic host cell which has been transiently transfected with the polynucleotide or vector of the invention and which expresses the polynucleotide of the invention. In another aspect, the said cell is a cell which has been genetically engineered to produce the fusion protein of the invention. How such cells can be genetically engineered by molecular biology techniques is well known to the skilled person.

The invention further relates to a method for producing the fusion proteins of the invention, comprising:

a) culturing a host cell comprising a nucleic acid encoding the fusion protein of the invention, preferably under serum-free conditions, b) obtaining from the host cell of step a) the fusion protein of the invention.

The invention further relates to a medicament, preferably a pharmaceutical composition, comprising the polynucleotide encoding the fusion proteins, the vector, the host cell, or the fusion proteins of the invention.

The term "medicament" as used herein refers, in one aspect, to a pharmaceutical composition containing the polynucleotide encoding the fusion protein, the vector, the host cell, or the fusion protein of the invention as pharmaceutical active compound, wherein the pharmaceutical composition may be used for non-human or preferably human therapy of various angiogenesis-related diseases or disorders as specified elsewhere herein in a therapeutically effective dose. Possible routes of administration have been set forth elsewhere herein. In an aspect, the polynucleotide encoding the fusion protein, the vector, the host cell, or the fusion protein of the invention can be present in liquid or lyophilized form. In an aspect, said compound can be present together with glycerol, protein stabilizers (e.g., human serum albumin (HSA)) or non-protein stabilizers. In another aspect, said compound may be pegylated.

The compound (i.e. the polynucleotide encoding the fusion protein, the vector, the host cell, or the fusion protein of the invention) is the active ingredient of the composition, and is in one aspect, administered in conventional dosage forms prepared by combining the drug with standard pharmaceutical carriers according to conventional procedures. These procedures may involve mixing, granulating, and compression, or dissolving the ingredients as appropriate to the desired preparation. It will be appreciated that the form and character of the pharmaceutical acceptable carrier or diluent is dictated by the amount of active ingredient with which it is to be combined, the route of administration, and other well-known variables.

The carrier(s) must be acceptable in the sense of being compatible with the other ingredients of the formulation and being not deleterious to the recipient thereof. The pharmaceutical carrier employed may include a solid, a gel, or a liquid. Exemplary of solid carriers are lactose, terra alba, sucrose, talc, gelatine, agar, pectin, acacia, magnesium stearate, stearic acid and the like. Exemplary of liquid carriers are phosphate buffered saline solution, syrup, oil, water, emulsions, various types of wetting agents, and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pennsylvania.

The diluent(s) is/are selected so as not to affect the biological activity, preferably, anti-angiogenic activity of the combination. Examples of such diluents are distilled water, physiological saline, Ringer's solutions, dextrose solution, and Hank's solution. In addition, the pharmaceutical composition or formulation may also include other carriers, adjuvants, or non-toxic, non-therapeutic, non-immunogenic stabilizers and the like.

A therapeutically effective dose refers to an amount of the compound to be used in medicament of the present invention which prevents, ameliorates or treats the symptoms accompanying an angiogenesis-related disease or condition referred to in this specification. Therapeutic efficacy and toxicity of the compound can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment.

The medicament referred to herein is administered at least once in order to treat or ameliorate or prevent a disease or condition recited in this specification. However, the said medicament may be administered more than one time.

Specific medicaments are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent. The resulting formulations are to be adapted to the mode of administration. Dosage recommendations shall be indicated in the prescribers or users instructions in order to anticipate dose adjustments depending on the considered recipient.

The medicament according to the present invention may in a further aspect of the invention comprise drugs in addition to the polynucleotide encoding the fusion protein, the vector, the host cell, or the fusion protein of the invention which are added to the medicament during its formulation. Finally, it is to be understood that the formulation of a medicament takes place under GMP standardized conditions or the like in order to ensure quality, pharmaceutical security, and effectiveness of the medicament.

In a further preferred embodiment of the fusion protein of the invention, the medicament or pharmaceutical composition comprising the polynucleotide encoding the fusion protein of the invention, the vector, the host cell, or the fusion protein of the invention is for the treatment or prevention of an angiogenesis-related disease selected from the group consisting of angiogenesis-dependent cancer including solid tumors, melanomas, tumor metastases, blood born tumors such as leukemias, benign tumors such as hemangiomas, acoustic neuromas, neurofibromas, trachomas, pyogenic granulomas, rheumatoid arthritis, psoriasis; ocular angiogenic diseases such as diabetic retinopathy, retinopathy of prematurity, macular degeneration, corneal graft rejection, neovascular glaucoma, retrolental fibroplasias, rubeosis; Osler-Webber syndrome; myocardial angiogenesis; plaque neovascularization; telangiectasia; hemophiliac joints, angiofibroma; wound granulation, diseases of excessive or abnormal stimulation of endothelial cells such as intestinal adhesions, atherosclerosis, scleroderma, hypertrophic scars (keloids); diseases that have angiogenesis as a pathologic consequence such as cat scratch disease (Rochele minalia quintosa) and ulcers (*Helobacter pylori*).

The invention further relates to a diagnostic composition comprising the polynucleotide, the vector, the host cell, or the fusion protein of the invention.

The invention further relates to the use comprising the polynucleotide, the vector, the host cell, or the fusion protein of the invention for determining an anti-angiogenic activity in a sample in vitro or in vivo.

The invention further relates to a kit comprising the polynucleotide, the vector, the host cell, or the fusion protein of the invention and an instruction sheet for the treatment of an angiogenesis-related disease.

The term "kit" as used herein refers to a collection of means comprising the fusion protein of the invention, the polynucleotide encoding the fusion protein, the vector and/or the host cell of the present invention which are provided in separate or common vials in a ready to use manner for carrying out the treatment of an angiogenesis-related disease. In an aspect, the kit comprises additional means for carrying out the treatment of an angiogenesis-related disease, in an aspect, further anti-angiogenic agents which can be used in combination with the protein oligomer or the fusion protein of the invention, such as those mentioned herein. Furthermore, in an aspect, the kit comprises instructions for carrying out the treatment of an angiogenesis-related disease. These instructions can be provided as a manual or can be in the form of a computer-implementable algorithm on a data storage medium which upon implementation is capable of governing one or more steps of the treatment of an angiogenesis-related disease. The instructions comprise information with respect to the dosage of the fusion protein of the invention, time and mode of administration and the like. In an aspect, the kit is to be used for carrying out the treatment of an angiogenesis-related disease specified above.

The invention further pertains to a(n) (in vitro) method for the identification of an anti-angiogenic agent, comprising a) contacting the oligomer or fusion protein of the invention with fibronectin and/or VEGF under conditions which allow binding of the oligomer or fusion protein to fibronectin and/or VEGF to form a complex, b) contacting the complex of step a) with a panel of agents, c) identifying and isolating those agents which are capable of binding to the complex of step a), and d) testing for anti-angiogenic activity of the agents identified in step c) in an in vitro assay.

The panel of agents used in step b) can be, for example, a library of proteins or antibodies, a phage display library, small organic compounds or the like. The method can further comprise a step (e), in which the regions of fibronectin responsible for binding to the oligomer or fusion protein of the invention can be identified. This information can then be used for the molecular design of anti-angiogenic and/or anti-tumor therapeutics.

The definitions and embodiments of the method using the protein oligomer of the invention apply *Mutatis mutandis.*

The invention also relates to a method for producing a mutated NC-1-Fc or Fc-NC-1 fusion protein of the invention, comprising:

a) introducing a single mutation in amino acid position 7 of the endostatin domain in the NC-1-Fc or Fc-NC-1 fusion protein by replacing glutamine by cysteine, and b) isolating the mutated NC-1-Fc or Fc-NC-1 fusion protein of step a).

Said mutation has been described elsewhere herein.

Finally, in contrast to previous reports, the inventors were able to generate tumors in mice which were resistant to Fc-endostatin. Fc-endostatin forms oligomers and, thus, mimics the oligomeric NC-1 effect described herein, for example, in that it binds to fibronectin, whereas endostatin monomer does not. These tumors were generated by sequential implantation and treatment of tumors, in murine lung cancer (LLC) and human pancreatic adenocarcinoma (BxPC3) up to 4 passages. Genome-wide expression profiling revealed down regulation of fibronectin as an important mechanism in rendering tumors resistant to Fc-endostatin treatment. This is in line with the inventor's observation of selective binding of oligomeric Fc-Endostatin and oligomeric NC-1 to fibronectin.

Accordingly, the invention pertains to a method for predicting the response of a cancer patient to an applied cancer therapy, comprising the steps of: a) measuring the level of fibronectin in a sample of the patient by using the NC-1 oligomer or fusion protein of the invention, and b) predicting the response of said patient to said cancer therapy, wherein low levels of fibronectin compared to a reference level (of a healthy subject) is indicative for a non-responding of the patient to the applied cancer therapy.

Further, the invention encompasses a kit comprising the NC-1 oligomer or fusion protein of the invention for predicting the tumor response to treatment with oligomeric NC-1 or fusion protein of the invention. As set forth above, said compounds of the invention can be used for detecting the level of fibronectin or fragments thereof in a sample of a cancer patient.

The inventors have surprisingly found that analysis of fibronectin levels by using the NC-1 oligomers or fusion proteins of the invention can be predictive for cancer therapy response. The ability of NC-1 oligomers or fusion proteins of the invention for binding to fibronectin can be used, for instance, for the determination of fibronectin levels in samples of cancer patients. Low levels of fibronectin detected by the NC-1 oligomers or fusion proteins of the invention are indicative for bad prognosis and can, therefore, be used as a molecular therapy predictor in order to identify treatment responders vs. non-responders among the cancer patients. More specifically, low fibronectin concentrations in the tumor, tumor environment, serum, plasma or urine of cancer patients undergoing an anti-tumor therapy, such as—but not limited to—treatment by NC-1 oligomers or Fc fusion proteins of the invention, chemotherapy or antibody therapy, is prognostic for a poor- or non-responding of the patient to the applied therapy.

Interestingly, the inventors identified a number of compensatory pathways being activated rendering tumors resistant to Fc-endostatin therapy. In particular, sequential treatment with IGF1R inhibitors seems promising and CCL2 seems to constitute another promising candidate target, as shown in the following examples. Since Fc-endostatin mimics the effects of NC-1 oligomers or fusion proteins of the invention, this finding is also relevant for patients resistant to therapy by said NC-1 oligomers or fusion proteins. In order to circumvent acquired drug resistance to oligomeric NC-1 or fusion proteins of the invention, concurrent or sequential therapy with anti-IGF1R, -CCL2 or -PI3K targeting agents can be used. To this end, inhibitors of the mentioned targets can be applied, such as antibodies or PI3K inhibitors described in the art.

In light of the above, the invention further relates to concurrent or sequential therapy with anti-IGF1R and/or -CCL2 targeting agents, such as—but not limited to—antibodies, to circumvent acquired drug resistance to oligomeric NC-1.

All references cited in the specification are herewith incorporated by reference with respect to their entire disclosure content and the disclosure content specifically mentioned in the specification.

In the following Figures and Examples, the term "hNC-1" corresponds to the human NC-1 domain and the term "mNC-1" to the murine NC-1 domain. The NC-1 domain is the naturally occurring trimeric NC-1 of collagen 18 comprising an association domain, a hinge region and an endostatin domain (including the zinc binding site), if not indicated otherwise.

FIGURES

FIG. 1 (A): Immunoprecipation of human Platelets.

Platelets from 15 ml of freshly collected plasma was lysed employing 25 mM Tris, 0.15 M NaCl, 1% NP-40, pH 7.5 and a cocktail of protease inhibitors (total volume was made 3 mls). The lysate was centrifuged and filtered. Proteins Fc, Fc-VEGF and Fc-endostatin (10 µg of each) were individually added to 1 ml of lysate. Protein A was employed. Incubation time was 18 h at 4° C. After three washes, the eluted samples were applied to PAGE and were stained with coomassie stain. The control lanes refer to the samples devoid of lysate. The candidate proteins were sliced out of the gel and sent out for Mass Spectra analysis.

FIG. 1 (B): Elisa.

Coating of proteins were done in PBS at concentration of 10 µg/ml. Fibronectin served as a ligand at the same concentration. All buffers contained 2% BSA, 0.1% Tween-20.

FIG. 1 (C): Biacore measurements of equilibrium constants for binding of endostatin monomer, dimer and NC-1 trimer to fibronectin.

Fibronectin samples were prepared by serial dilution into 0.01 M Hepes, pH 7.4, 0.15 M NaCl, 0.05% Surfactant containing 1 mg/ml BSA in the range 0.78 nM-100 nM and flowed over control and derivatized surfaces for three minutes at a flow-rate of 60 µl/min. Dissociation phases were monitored for 5 minutes. Zero concentration blank buffer cycles were included as negative control samples. Sensor surfaces were regenerated using a 1 minute injection of 1 M ethanolamine, pH 8.5 following each interaction analysis cycle. Non-specific binding effects to sensor surface CM4 were not observed. Calculated ka, kd and KD are shown. Different curves correspond to different concentrations of fibronectin.

FIGS. 2A-2G: Endostatin binding activity and co-localization with fibronectin in blood vessels.

Immunohistochemistry was used to verify the distribution of Fc-endostatin in ASPC-1 xenograft mice after treatments. (A) The exogenous endostatin was detected by Alexa 488-labeled antibody (green) and vessel marker, CD31 was used and detected by Alexa 594-labeled antibody (red) in tumor, heart and kidney. (B) α-SMA, pericyte marker (red) was used to confirm the endostatin binding to tumor vessels. (C) Exogenous endostatin (green) distribution is similar to fibronectin (red) in tumor. Human Fc (hFc) control shows no binding. (D) Endogenous collagen 18 (green) and fibronectin (red) were detected by polyclonal antibodies against endostatin and fibronectin in non-treated animal tumor. (E) Staining of Fc-endostatin and integrin α5β1. (F) Staining of vW and integrin α5β1. (G) E14.5 mouse brain embryonic sections were used to verify the distribution of fibronectin, VEGF and Fc-endostatin (Bar, 100 µm).

FIG. 3 (A): Binding of Fc-endostatin and collagen hNC-1 to endothelial cells.

HUVECs were incubated with Fc-endostatin and detected with Alexa 488 IgG or human NC-1 (hNC-1) trimer and detected by anti-His tag monoclonal antibody. The fibronectin staining is showed in red color (Bar, 20 µm).

FIGS. 3 (B)(a)-(c): hNC-1 inhibits endothelial cell migration.

HUVECs were plated into 24-well inserts of transwell plate in duplication. The lower chamber was filled with serum free medium containing 100 ng/ml rhesus VEGF (rhVEGF) plus different concentrations of hNC-1. After incubation for 16 h at 37° C., the cells were fixed and stained. Endothelial cells show less migration under 100 and 200 ng/ml of hNC-1 treated (a). The effect of hNC-1 in inhibition of endothelial cell migration shows a U-shape curve (b). Endostatin monomer, dimer and NC-1 were used for comparison (c).

Figure 4:

FIG. 4: Immunoprecipitation of human Sera and Platelets followed by Western analysis.

(A) M1 and M2 refer to recombinant endostatin (187 amino acids) and NC-1, respectively. 1) pre-immune and human serum. 2) endostatin antibody and human serum. (B) M contains hNC1 and endostatin markers. Lanes 1 and 2 are the same as in (A). Lanes 3 (pre-immune serum) and 4 (anti-endostatin antibody) correspond to the serum of an individual not represented in (A). (C) Affinity purification of human serum obtained from a different PRP sample than the one employed in (A) followed by Western analysis without IP step. (D) Immunoprecipitation of human platelets. hNC-1 and endostatin markers are in lane M. 1) pre-immune serum and platelets lysate. 2) anti-endostatin antibody and platelets lysate. IPs were carried out in the presence of Protein A. After subjecting the samples to PAGE and transfer, the membranes were treated with anti-endostatin monoclonal antibody PDM.

Figure 5:
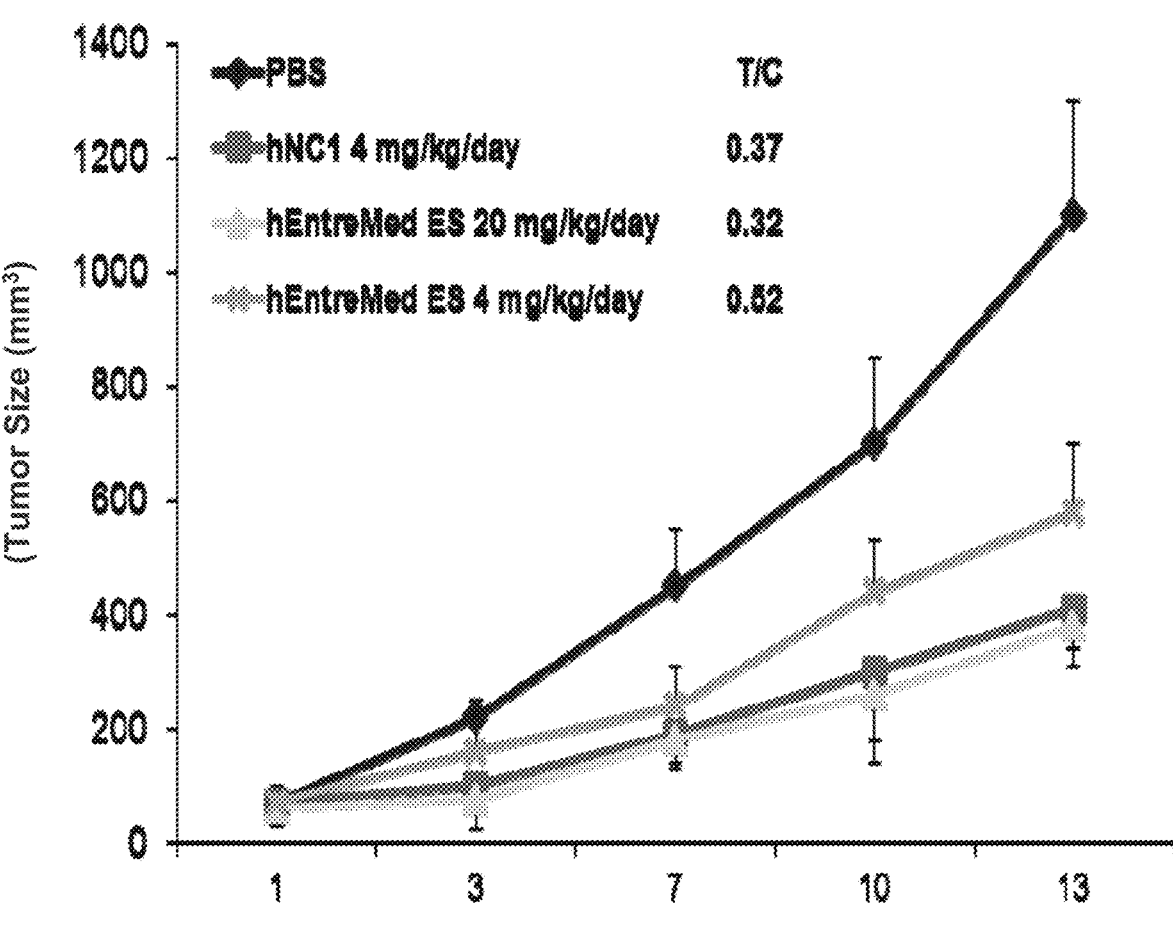

FIG. 5: Treatment of mouse bearing human melanoma cancer cells (A2058) with hNC-1.

4-6 tumor-bearing nude mice in each group were subcutaneously (s.c.) treated with hNC-1 (100 µg/mouse once a day), clinical-grade endostatin (100 and 500 µg/mouse once a day) or PBS. Treatment was stopped prior to the development of necrosis. Sites of injection were away from tumors. Tumor sizes and the ratio of treated/control (T/C) is shown. The hNC-1 treated group shows 67% inhibition of tumor growth in the end of experiment, whereas the group treated with endostatin shows only 48% inhibition.

Figure 6:
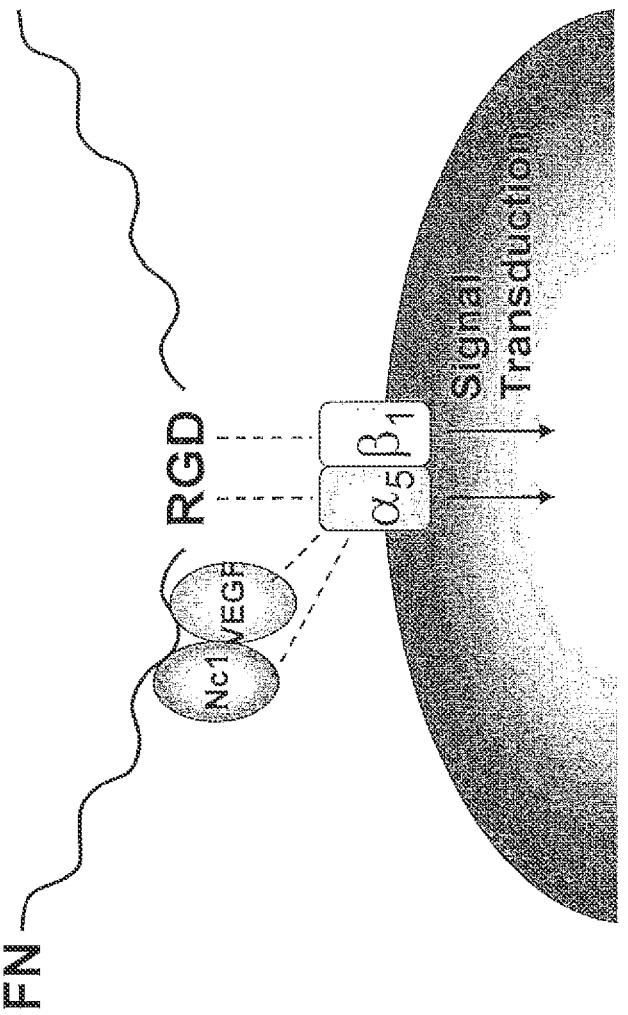

FIG. 6: Schematic model of interactions among fibronectin, integrin $\alpha5\beta1$, VEGF-A and hNC-1.

Figure 7:
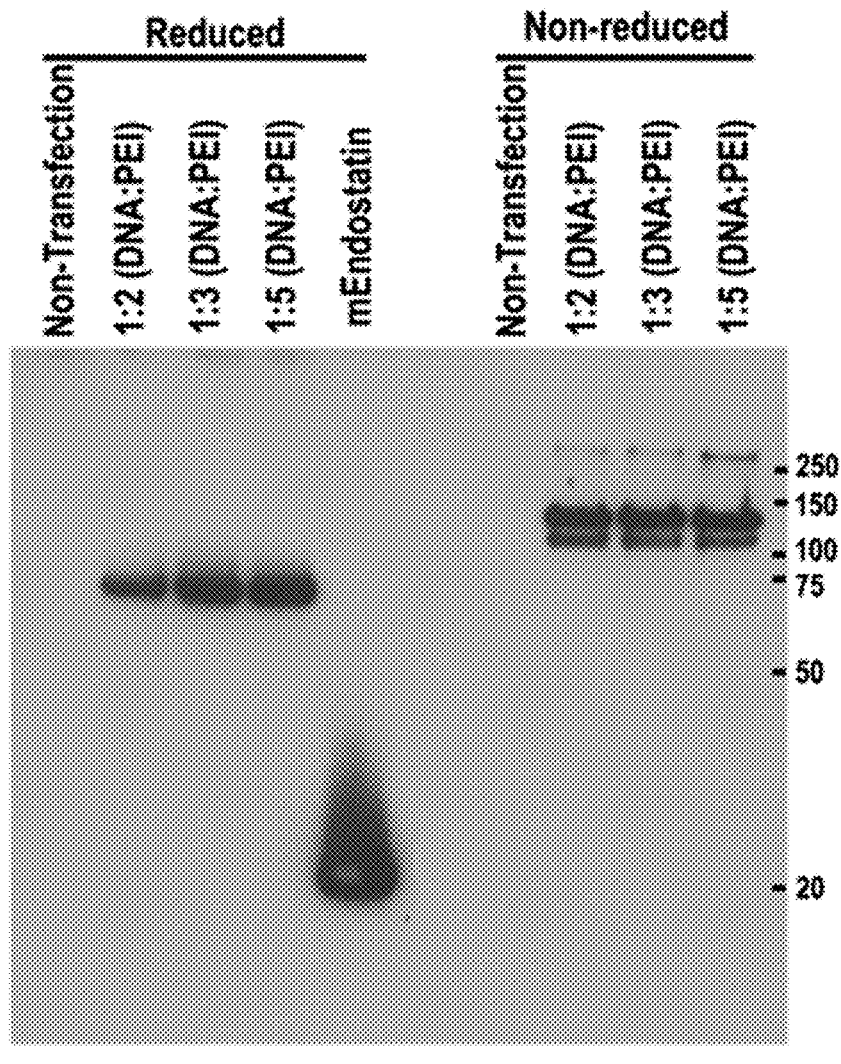

FIG. 7: SDS gel of a murine Fc-NC-1 fusion protein as a function of the amount of plasmid used in transfection of 293 kidney cells under reduced and non-reduced conditions.

Under reduced conditions, the product is a single chain consisting of Fc and NC-1. Under non-reduced conditions, the product is a dimer because Fc is disulfide bonded. The single band in the middle of the gel is due to endostatin marker which has a molecular weight of 20 Kd.

FIGS. 8.1-8.4: Generation of resistant Lewis Lung Cancer tumors in-vivo after prolonged exposure to mouse Fc-angiostatin and Fc-endostatin.

Dimerization of the NC-1 endostatin domains were achieved using IgG-Fc. After strong initial inhibition of tumor growth (p1) tumors were exposed for a prolonged period of time to Fc-endostatin anti-angiogenic therapy (up to four consecutive passages, p1-4) by re-implanting the tumors in new animals once they reached a tumor size of >1000-1500 mm$^3$. Sequential in-vivo tumor passaging was performed to achieve prolonged and continuous exposure to anti-angiogenic therapy to enrich for the resistant tumor cell population. P4 tumors, lower panel, were growing even faster than non-treated control p4 tumors despite continues exposure to oligomeric NC-1-fragment (Fc-endostatin). These data clearly show that tumors could develop acquired drug resistance to oligomeric fragments of NC-1.

FIGS. 9.1-9.5: Genome-wide expression profiling of oligomeric-NC-1 fragments (mFc-Endostatin) resistant Lewis Lung Cancer (LLC) tumors.

Expression profiling revealed that fibronectin (FN1) is markedly down regulated in murine (m)Fc-Endostatin (FcEndo) resistant tumors (heatmap, green box). The regulation of candidate genes was confirmed by q-RT-PCR and Fold-expression ratios relative to p4 control tumors are presented (diagrams). This finding supports the inventor's data demonstrating that anti-angiogenic effects of oligomeric NC-1-fragments are exerted via binding to FN1. Therefore, down regulation of FN1 in tumors render them resistant to oligomeric NC-1. Moreover, the inventors identified several key pathways such as IGF1R and CCL2 to be up regulated in Fc-endostatin resistant tumors (red box). Hence, down-regulation of the key binding partner and compensatory up regulation of alternative angiogenic pathways constitute a coordinated mechanism by which tumors may evade treatment with oligomeric NC-1 fragments. Therefore, FN1 level as well as IGF1R/CCL2 regulation might be instrumental in predicting tumor response to cancer therapies consisting of oligomeric-NC-1 fragments.

FIG. 10: A schematic overview of critical motifs within the endostatin (ED)-domain and fibronectin (FN).

The integrin binding domain within FN consists of two motifs, the RGD and PHSRN (SEQ ID NO: 20) motif. In analogy to NC1-ED, heparin binding sites such as HepII are available that mediate binding to other heparin binding factors such as VEGF. The amino-terminal Zinc binding motif of NC1-ED contains two critical histidines (H) that once mutated with Alanine (A) abrogate its activity; adapted from Tjin Tham Sjin et al. Cancer Res 2005, 65, 3656-63 and Wijelath et al. 2006, Circ. Res. 99, 853-860. The sequence of the active motif within NC1-ED containing the two critical histidines (mP1) is HTHQDFQPVLHLVAL-NTPLSGGMRGIR (SEQ ID NO: 18), and the sequence with the histidines mutated to Alanine (mP1-H1/3A) is ATAQDFQPVLHLVALNTPLSGGMRGIR (SEQ ID NO: 19).

Figure 11:
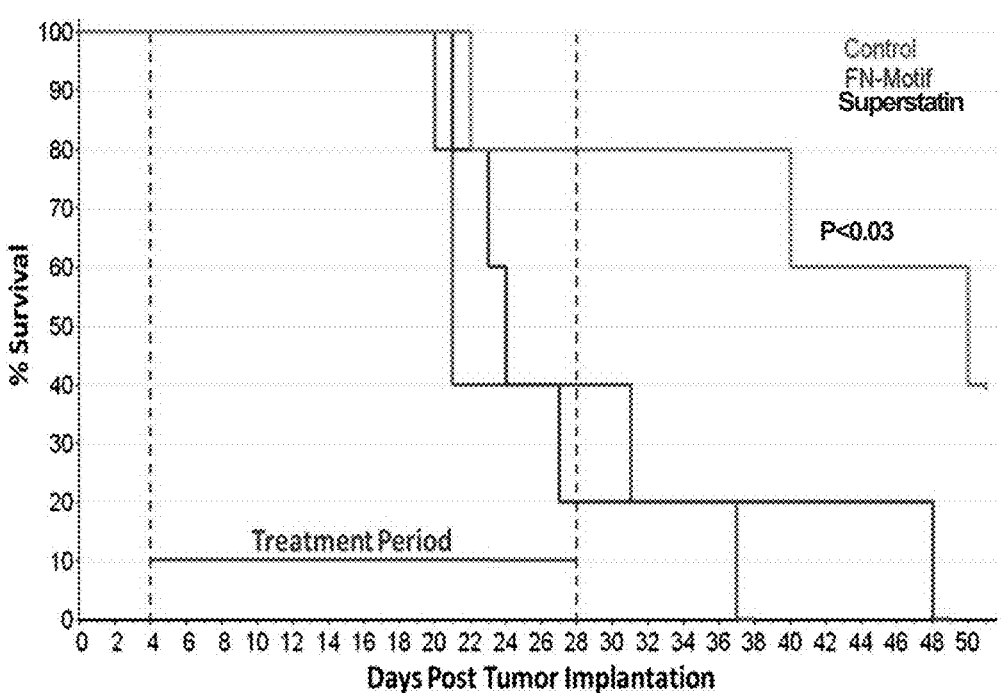

FIG. 11: Superstatin potently inhibits tumor growth.

Wild type LLC tumors (10.000 cells) were implanted s.c. in C57B16 mice. Tumors were sham treated (PBS, control), with the reference FN-mimetic-peptide ("FN-Motif") containing only the "LYAVTGRGDSPASSK" sequence (SEQ ID NO: 8) or with murine Superstatin (SEQ ID NO: 7) at the dose of 50 µg peptide in 100 µl PBS every 12 h s.c. (n: 5 in each group). Treatment was started 4 days after tumor implantation ("prevention trial") and continued for 24 days. Of note, during the treatment period only a single tumor grew in the Superstatin group. Two additional tumors appeared only after cessation of Superstatin therapy indicating that these hard-to-treat tumors were controlled by this therapy. Tumor size reaching 1000 mm$^2$ was considered as death event in the Kaplan-Meier analysis. Superstatin significantly prolonged survival (p<0.03 by log-rank test) as compared to control. In contrast, the FN-Motif alone (SEQ ID NO: 8) showed no significant improvement in prevention of tumor growth.

Figure 12:
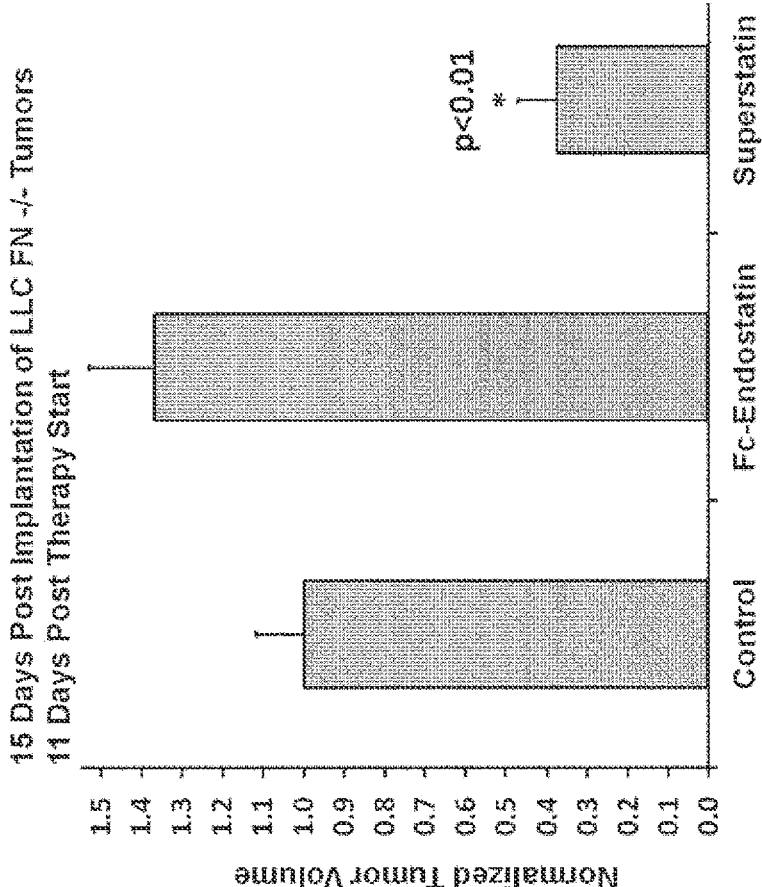

FIG. 12: Knockdown of Fibronectin (FN) rendered tumor resistant to oligomeric NC1 substrates, as exemplified for ED-Dimer (Fc-Endostatin).

In contrast, the Superstatin peptide (SEQ ID NO: 7) exerts potent tumor growth inhibition in FN −/− LLC tumors growing s.c. in C57B16 mice.

Figure 13:
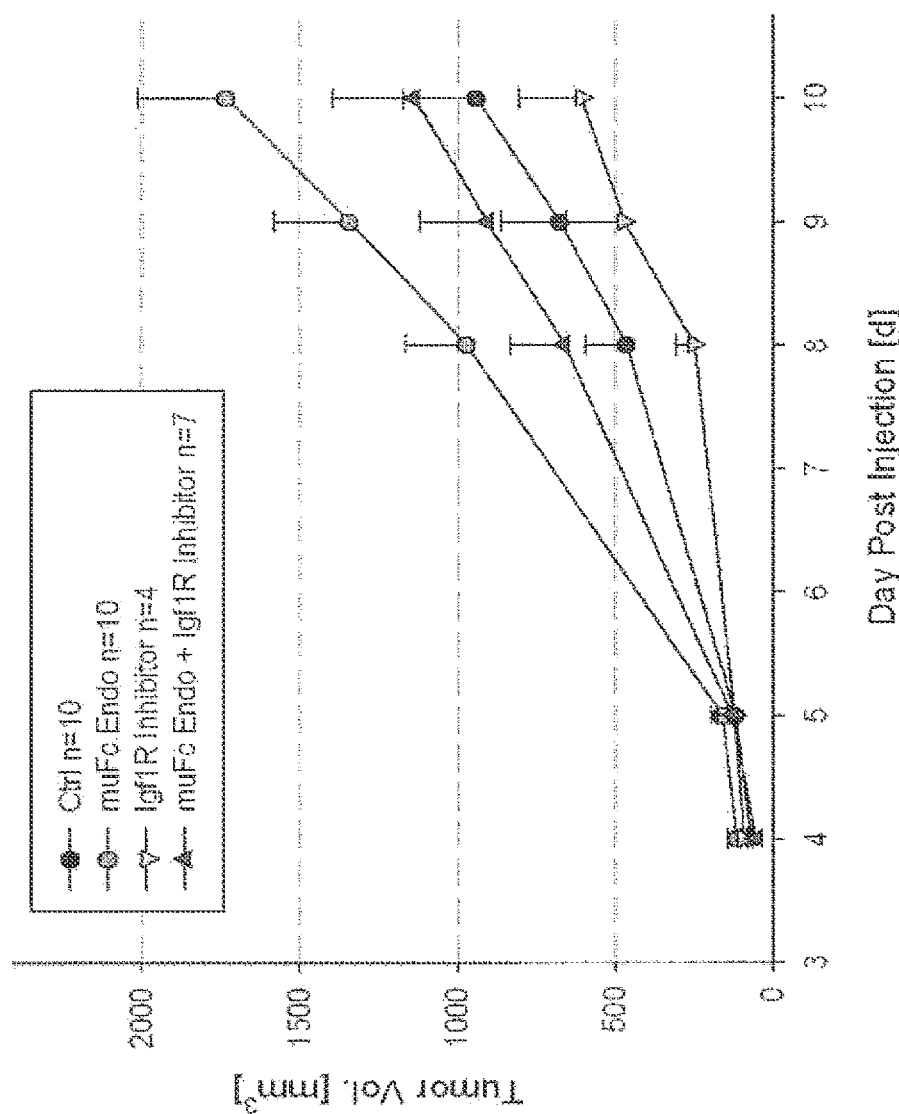

FIG. 13: Sequential treatment with IGF1R-Inhibitor is effective in treatment of murine Fc-Endostatin (muFcEndo)-resistant LLC tumors.

Previously generated passage four Fc-Endostatin-resistant LLC cells (Endo P4, as described in the following examples) were subcutaneously injected to C57B16 mice. In passage 5, tumors grew faster if endostatin selection pressure was maintained as compared to sham treated tumors (Ctrl.). Sequential inhibition of IGF1R signaling (20 mg/kg cyclolignan picropodophyllin, PPP, IP injection) inhibited tumor growth. However, concurrent administration only partially reversed the enhanced growth kinetic induced by mFc-Endo selection pressure.

Figure 14:
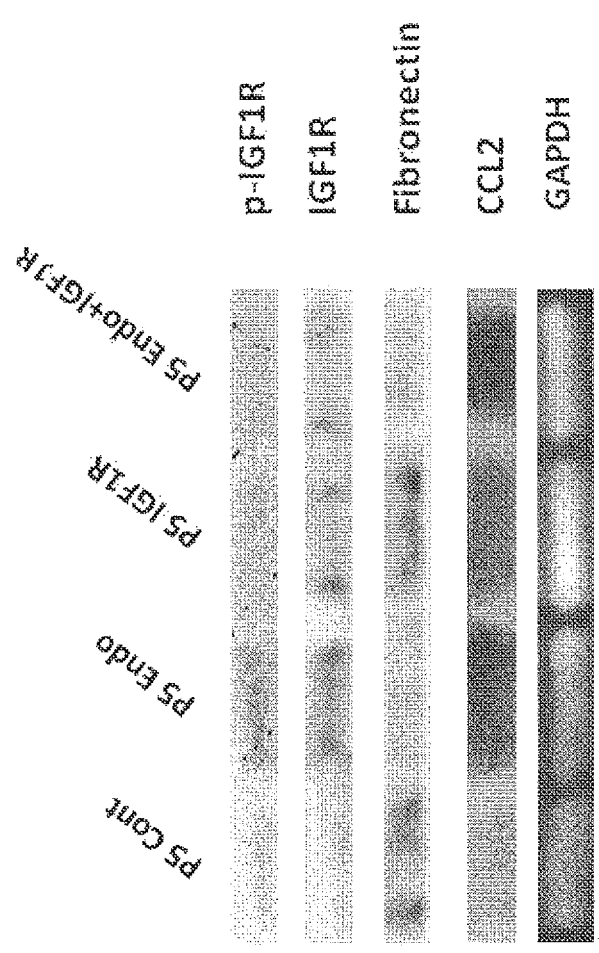

FIG. 14: Differential expression of proteins in passage 5 (P5) Fc-Endostatin-(Endo)-resistant LLC tumor cells. Protein analysis by Western blot further confirmed enhanced IGF1R expression and phosphorylation (p-IGF1R), down-regulation of Fibronectin and up-regulation of CCL2 as the function of therapy with murine Fc-Endostatin (Endo) in passage 5 LLC tumors. Sequential treatment with IGF1R inhibitor partially reversed this phenotype.

EXAMPLES

The invention will now be illustrated by examples which shall, however, not be construed as limiting the scope of the invention.

Example 1: Materials and Methods 1.1 Cell lines and cell culture. Human tumor cell lines A2058 (melanoma) and human pancreatic cancer cell line ASPC-1 were cultured in DMEM with L-glutamine and supplemented with 10% FCS and antibiotics. HUVEC (Lonza, Switzerland) was maintained in EBM endothelial growth media and EGM Bullet Kit (Lonza, Switzerland) with antibiotics.

1.2 Expression and Purification. Construction, expression and purification of human Fc-endostatin (hFc-endostatin), artificial endostatin dimer and NC-1 have been described previously (Bergers et al., 1999, *Science* 284, 808, Lo et al. 1998, *Protein Eng* 11, 495; Kuo et al. 2001, *J Cell Biol* 152, 1233; Wen et al. 1999. *Cancer Res* 59, 1233). The recombinant constructs were prepared by placing the Fc domains at the N-terminus of endostatin Stable cell lines of these constructs were produced in NS/0 murine myeloma cells. The proteins were expressed and secreted into the media. Protein A was used for purification of the recombinant proteins (at least 90% purity). Approximately, 50 mg/liter of Fc-endostatin has been obtained by employing fermentors of 10-18 liter capacity. Human collagen 18 NC-1 preparation was described previously (Wen et al., loc. cit.) The protein was expressed and secreted into the media and purified on Ni-Agarose (Invitrogen).

1.3 Surface Plasmon Resonance (SPR) binding assays. This analysis provides for a unique method for measuring equilibrium constants between two binding partners. It is able to evaluate the kinetics of an interaction by recording the rates of complex formation (ka) and dissociation (kd) followed by employing a software which determines the values of these two parameters. Equilibrium constant (KD) is obtained by calculating the ration of kd/ka Human VEGF (R&D), endostatin, endostatin dimer and human NC-1 (hNC-1) were diluted to 50 μg/ml in 10 mM Sodium Acetate, pH 5.5 and immobilized onto series S sensor chip(s) CM4 via a standard N-ethyl-N'-(dimethyl-aminopropyl)carbodiimide/N-hydroxysuccinimide (EDC/NHS) amine coupling procedures. Control surfaces were prepared similarly without protein derivatization and utilized as a reference surface for compound binding experiments.

Binding measurements were performed using a Biacore™ (GE Healthcare, Uppsala, Sweden) instrument which employs surface plasmon resonance to detect and monitor molecular interactions.

Data analysis was carried out using Biacore T100 evaluation software v1.1.1. Data were prepared by subtraction of reference surface data and blank buffer sample data, a procedure commonly referred to as 'double referencing' and fitted to a 1:1 langmuir binding model.

1.4 Animal and tumor models. All animal procedures were carried out in compliance with Children's Hospital Boston guidelines Protocols were approved by the Institutional Animal Care and Use Committee. Eight-week-old male (24-27 g) nude/nude mice (Massachusetts General Hospital, Boston, MA) were used. Mice were acclimated, caged in groups of five in a barrier care facility, and fed animal chow and water ad libitum. Animals were euthanized by $CO_2$ inhalation. Human melanoma cell line A2058 was used for animal studies. A suspension of $2 \times 10^6$ tumor cells in 0.1 ml of PBS was injected subcutaneously (s.c.) into the dorsa of mice at the proximal midline. Mice were weighed and tumors were monitored twice a week in two diameters with digital calipers. Tumor volumes were determined using $a^2 \times b \times 0.52$ (where a is the shortest and b is the longest diameter). Tumors were allowed to grow to ~100 mm³ and mice were randomized. Treatment was by bolus s.c. injections. After experiments were completed, tumors and organs were excised and fixed in either 4% paraformaldehyde or were snap frozen. Four to six mice were treated with each group.

1.5 Immunocytochemistry. HUVECs were plated and grown on cover slips. Cells were incubated with 10 μg/ml hFc-endostatin, hFc, hNC-1 or control IgG for 120 min at 37° C. and then fixed. The slips were incubated in the blocking buffer (2% BSA PBS) for 30 min. For hFc-endostatin or hFc groups, the slides were incubated with Alexa 488 antihuman IgG for imaging. For hNC-1 or IgG groups, the slides were incubated with mouse anti-His-tag monoclonal antibody, then probed by Alexa 488 anti-mouse IgG. Anti-fibronectin antibody (R&D) was used for secondary staining for all slides and probed by Alexa 594 anti-goat IgG and imaged by confocal-microscopy. DAPI counterstaining of nuclei is shown in blue.

1.6 Immunohistochemistry. Tumors sections were rinsed by cold PBS and fixed with 4% paraformaldehyde for 10 min with before staining. Human Fc-endostatin was detected by Alexa 488 anti-human IgG. Antibodies to collagen 18 (R&D), fibronectin (R&D), integrin α5 (R&D) CD31 (BD Pharmingen, San Jose, CA) and von Willebrand Factor (Dako, Carpinteria, CA), α-SMA (Dako, Carpinteria, CA) were used for staining. The primary antibodies were detected by Alexa 488 or 594-labeled secondary antibodies (Molecular Probes, Eugene, OR). The sections were imaged by confocal-microscopy (model DM IRE2: Leica).

1.7 Endothelial cell migration assay. HUVECs were washed by serum free EBM medium twice, re-suspended at $5 \times 10^4$ cells/well in 0.6 ml of medium, were plated into 24-well inserts (Coring, 8 μm pore size) in duplicates. The lower chamber was filled with 0.6 ml of serum free EBM medium containing 100 ng/ml rhesus (rh)VEGF (R&D) After incubation for 16 h at 37° C., the cells were fixed by methanol and stained with eosin and hemotoxlin. Cells on the upper side of the transwell membrane were removed by cotton swab. Cells migrating to the lower side of membrane were counted.

1.8 Flow-cytometry analysis of human Fc-endostatin (hFcES) binding on cell-surface. All operations were performed at 4° C. HUVECs were trypsinized and resuspended in PBS (2% BSA) for 30 min followed by 1 h incubation with 1 and 10 μg/ml hFcES or hFc. Cells were centrifuged and washed by cold PBS, and then incubated with FITC-labeled secondary antibodies (Sigma, St. Louis, MO) against human Fc fragment and analyzed by BD Biosciences FACS Calibur flow cytometer.

1.9 Statistical methods. Data are expressed as means plus or minus SD. Statistical significance was assessed using the Student t test.

Example 2: Results 2.1 Dimeric Endostatin and NC-1 bind Fibronectin. Because of reports demonstrating the existence of endostatin in platelets, it has been proceeded with a platelets lysate to identify proteins binding to endostatin (Italiano et al. 2008, *Blood* 111, 1227). One of the advantages of Fc-endostatin is that it enables to use this construct for immunoprecipitation (IP) without introducing an additional antibody to form a complex. Three protein constructs human Fc (control), dimeric human (h)Fc-Endostatin and hFc-VEGF were employed. The data are shown in FIG. 1(A). Comparing IP results for the three above mentioned reagents, the major difference among the lanes of coomassie stained polyacrylamidegel was in the vicinity of 200 kDa. Mass spectra analysis of this region led to identification of fibronectin as the candidate binding protein for both endostatin and VEGF. To confirm binding of endostatin and VEGF to fibronectin, Elisa was performed (FIG. 1B). Endostatin dimer, NC-1, VEGF and integrin α5β1 (a natural receptor for fibronectin) bound fibronectin whereas endostatin monomer did not. Artificial endostatin dimer was generated by introducing a single mutation in amino acid position 7 of endostatin (changing glutamine to cysteine) in the recombinant Fc-endostatin. Upon digestion of this mutant protein by enter-okinase, endostatin dimer is produced, linked by a disulfide bond (Kuo et al., loc. cit.).

In order to measure equilibrium binding constants for the above proteins, a Biacore system was employed. High affinity constants were obtained for endostatin dimer, NC-1 and VEGF (FIG. 1C). No binding was detected between endostatin monomer and fibronectin. In support of this data, VEGF binding to fibronectin has been reported by other groups previously (Wijelath et al. 2006, *Circ Res* 99, 853). Fc-endostatin imposes a dimeric structure on the two molecules of endostatin at the C-terminus of Fc dimer. Binding constant of Fc-endostatin to fibronectin is similar to endostatin dimer (data not shown).

Figure 2A:
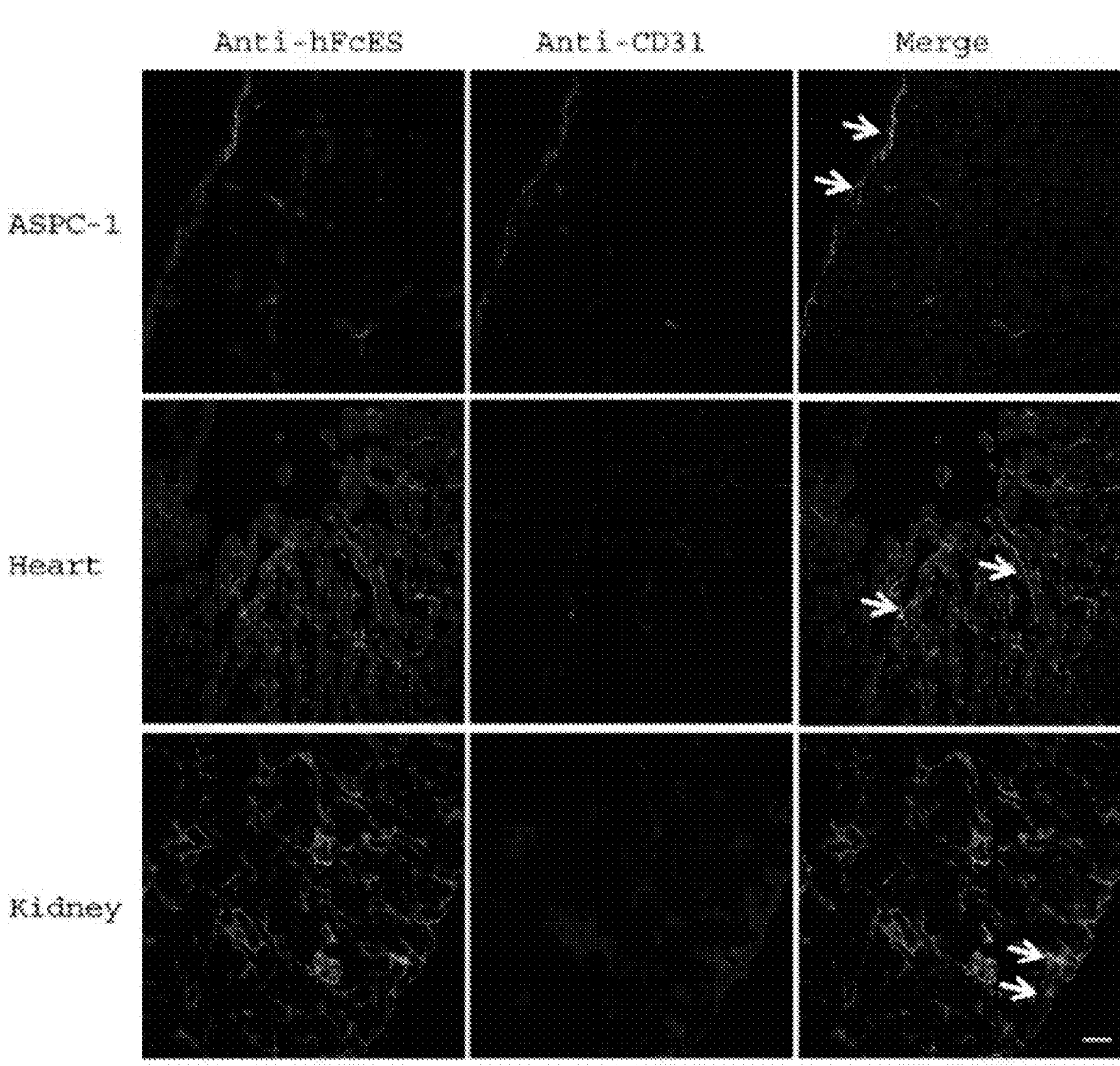
Figure 2B:
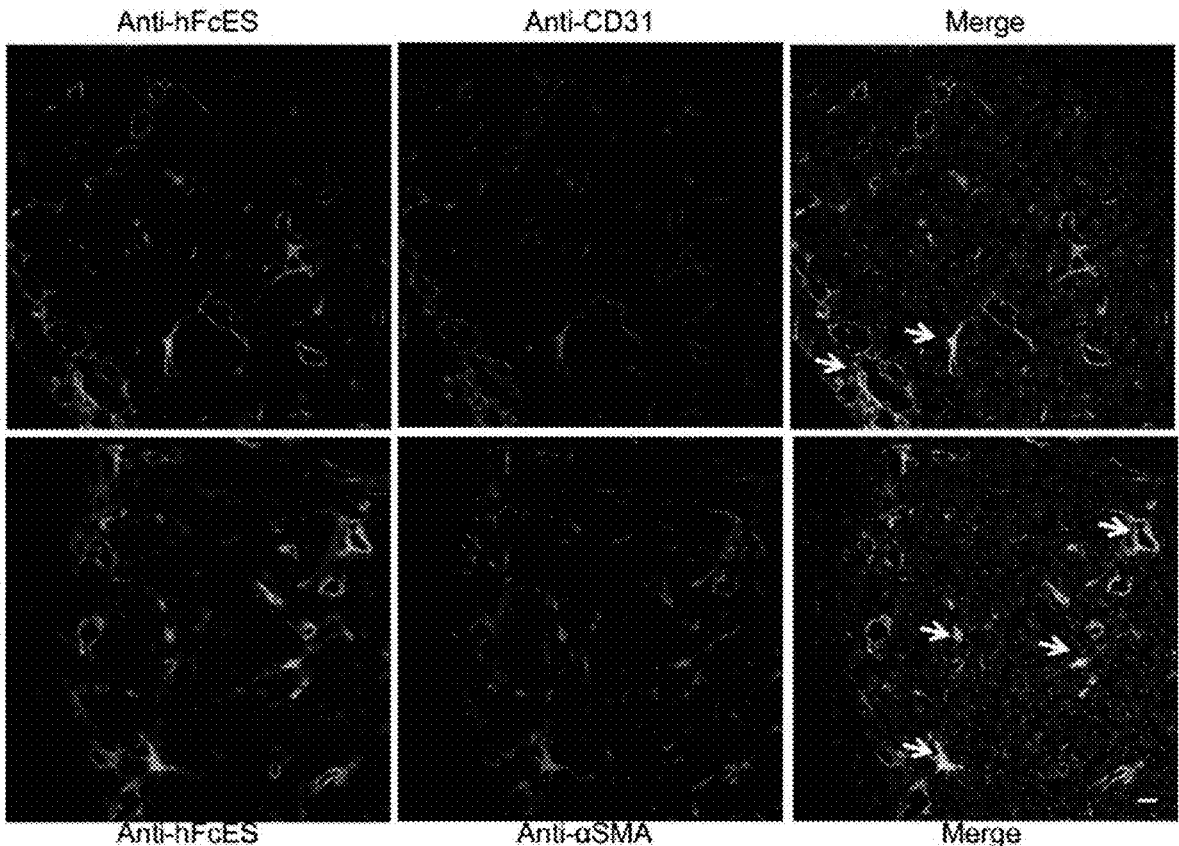
Figure 2C:
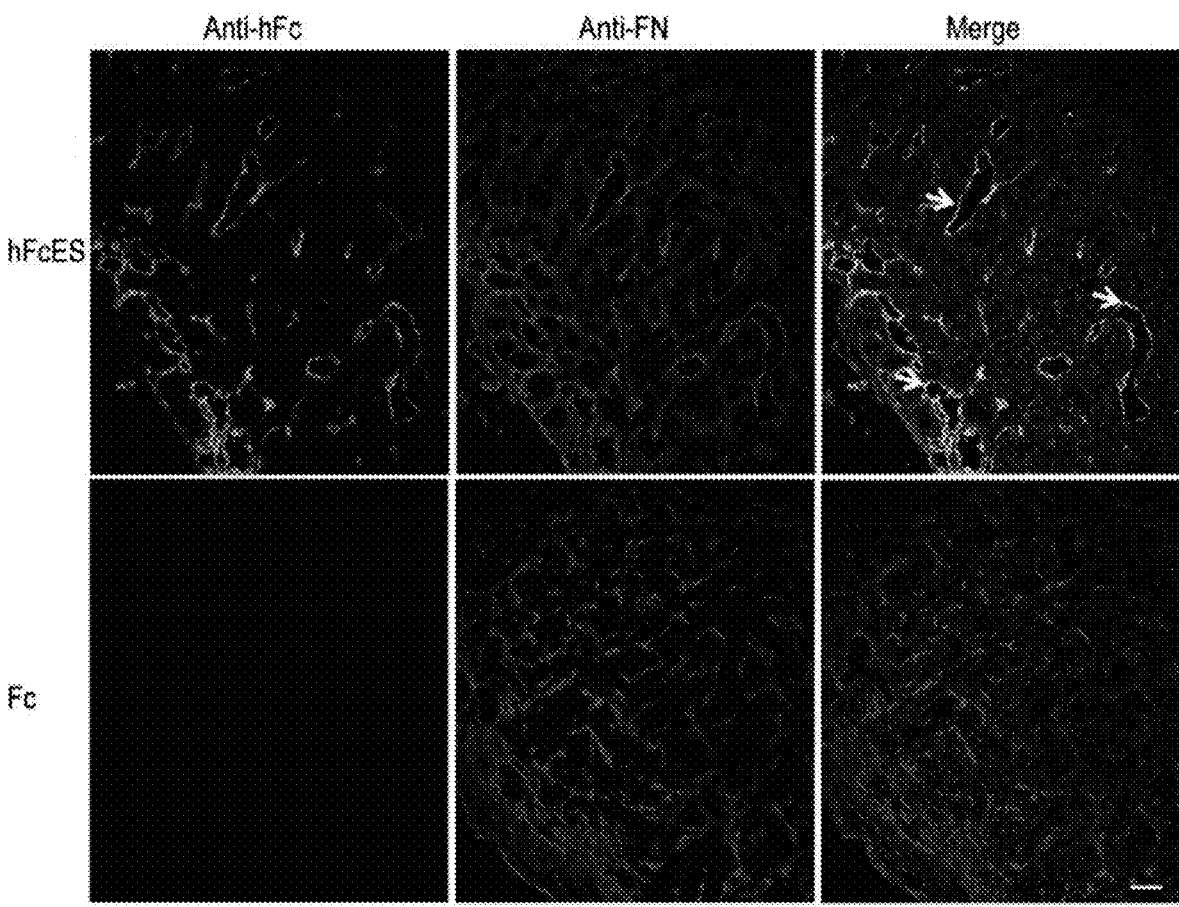
Figure 2D:
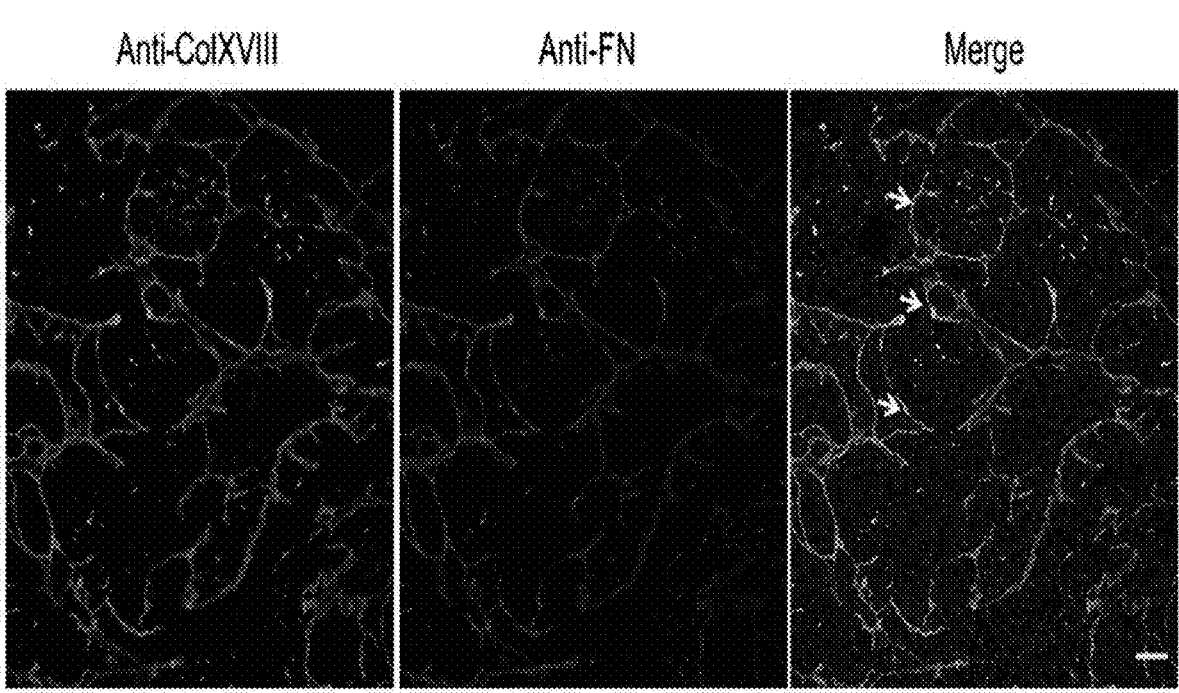
Figure 2E:
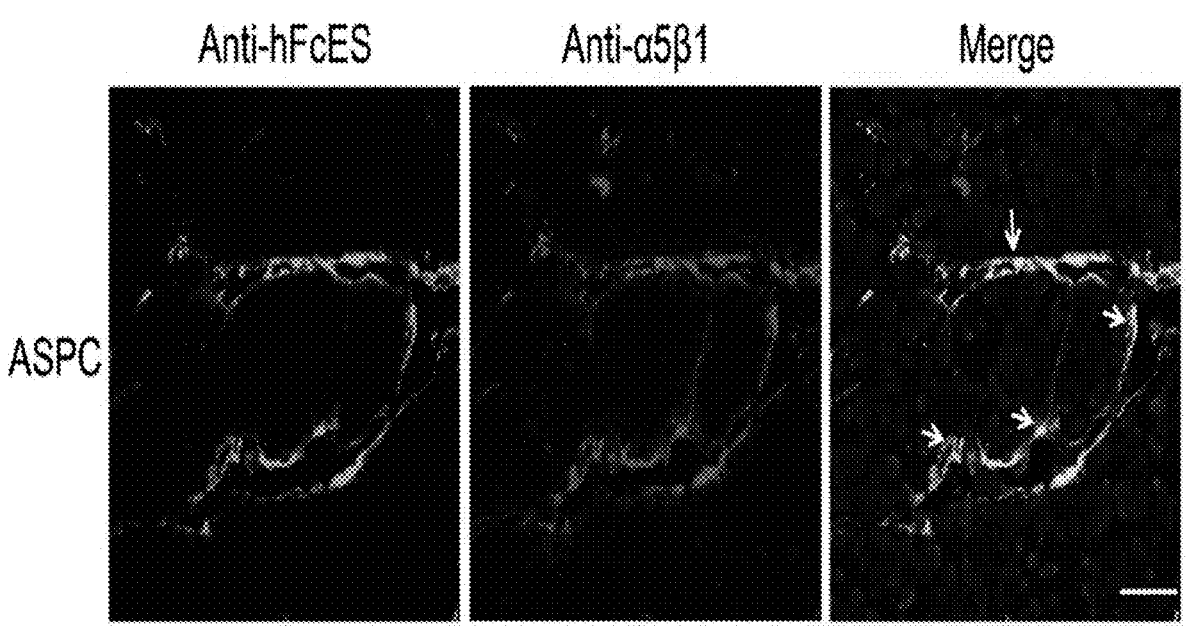
Figure 2F:
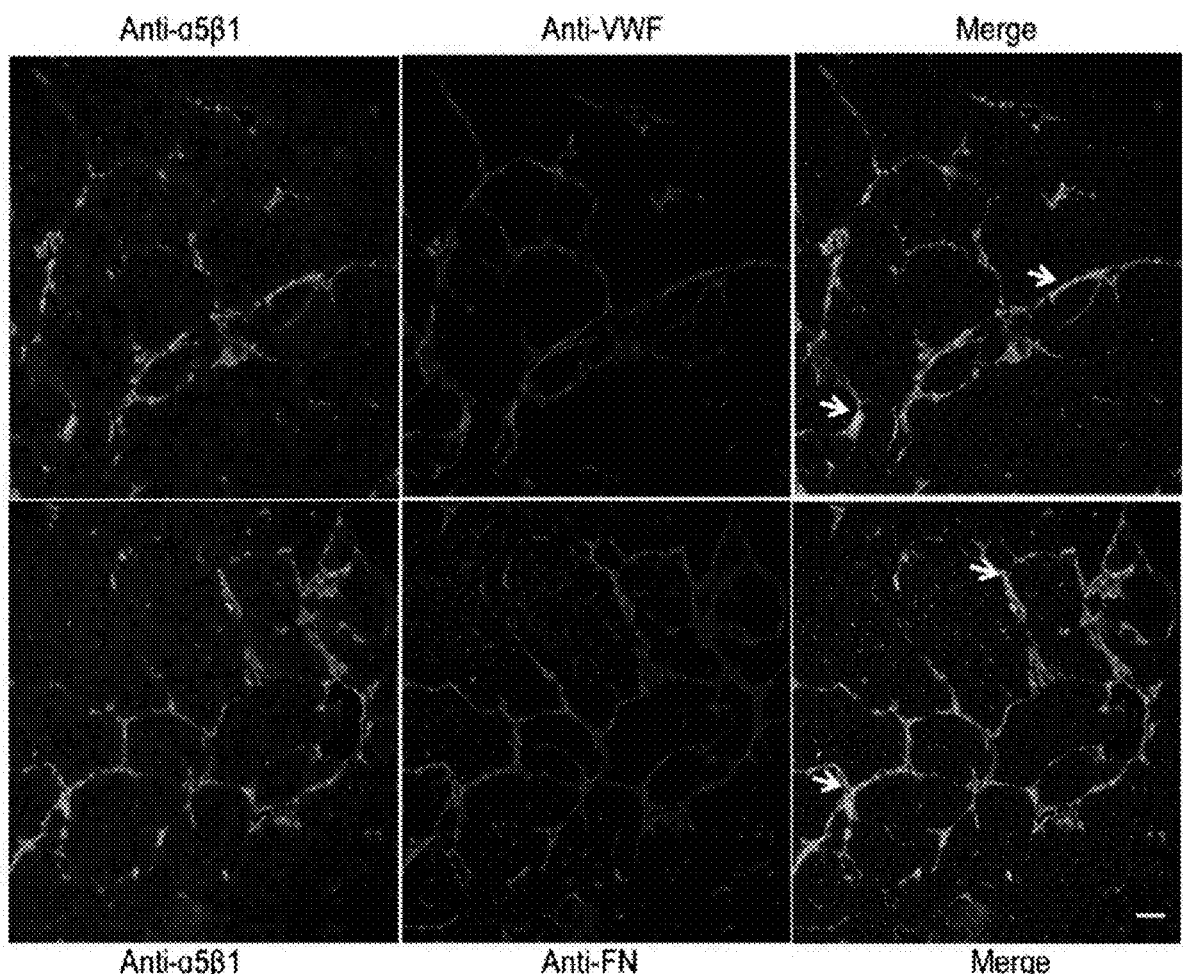
Figure 2G:
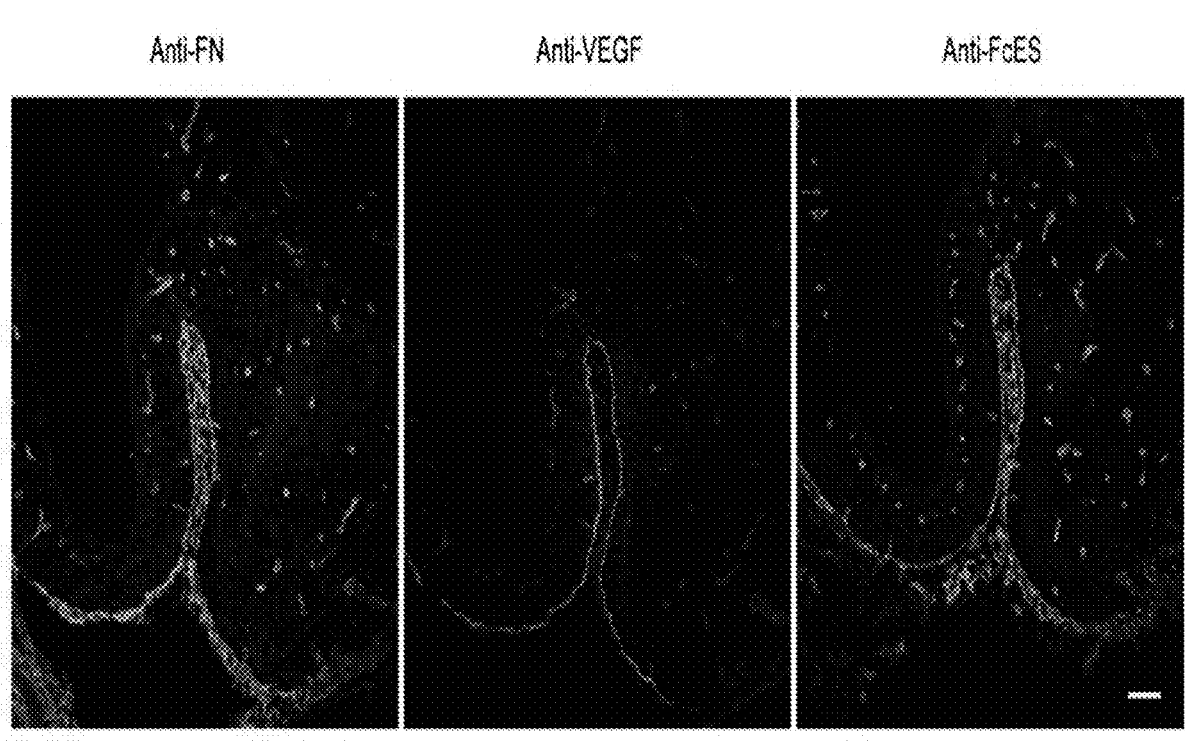

2.2 Immunohistochemistry studies demonstrate that dimeric Endostatin targets endothelial cells through fibronectin. Immunofluorescence (IF) analysis was used to verify the systemic distribution of hFc-endostatin in an ASPC-1 xenograft animal model. The distribution of exogenous oligomeric endostatin was detected, using antibody to Fc, and shown in FIG. 2A. The imaging results showed that injected oligomeric endostatin was found not only in tumor but also in heart and kidney endothelial cells. In addition to CD31 (endothelial cell) staining, the pericyte marker, α-SMA was used to confirm the interaction of endostatin with blood vessels (FIG. 2B). To examine binding of endostatin to fibronectin, hFc-endostatin treated tumor sections of xenograft models were prepared. The exogenous dimeric hFc-endostatin (hFcES) shows co-localization with endogenous fibronection (FIG. 2C). Co-localization of endogenous collagen 18 and endogenous fibronectin has also been detected (FIG. 2D). Integrin α5β1 is a receptor of fibronectin (Hynes 1992, *Cell* 69, 11). The imaging data showed that hFcES was also co-localized with integrin α5β1 (FIG. 2E). Finally, we detected co-localization of VWF, integrin α5β1 on tumor sections (FIG. 2F). These data demonstrate close proximity of dimeric-hFcES, fibronectin, integrin α5β1 and blood vessels. In addition, ex vivo E14.5 mouse brain embryonic sections were used to confirm this phenomenon. Fibronectin, VEGF and hFcES show similar binding pattern in mouse embryonic brain (FIG. 2G), confirming that VEGF is a component of this assembly.

Figure 3A:
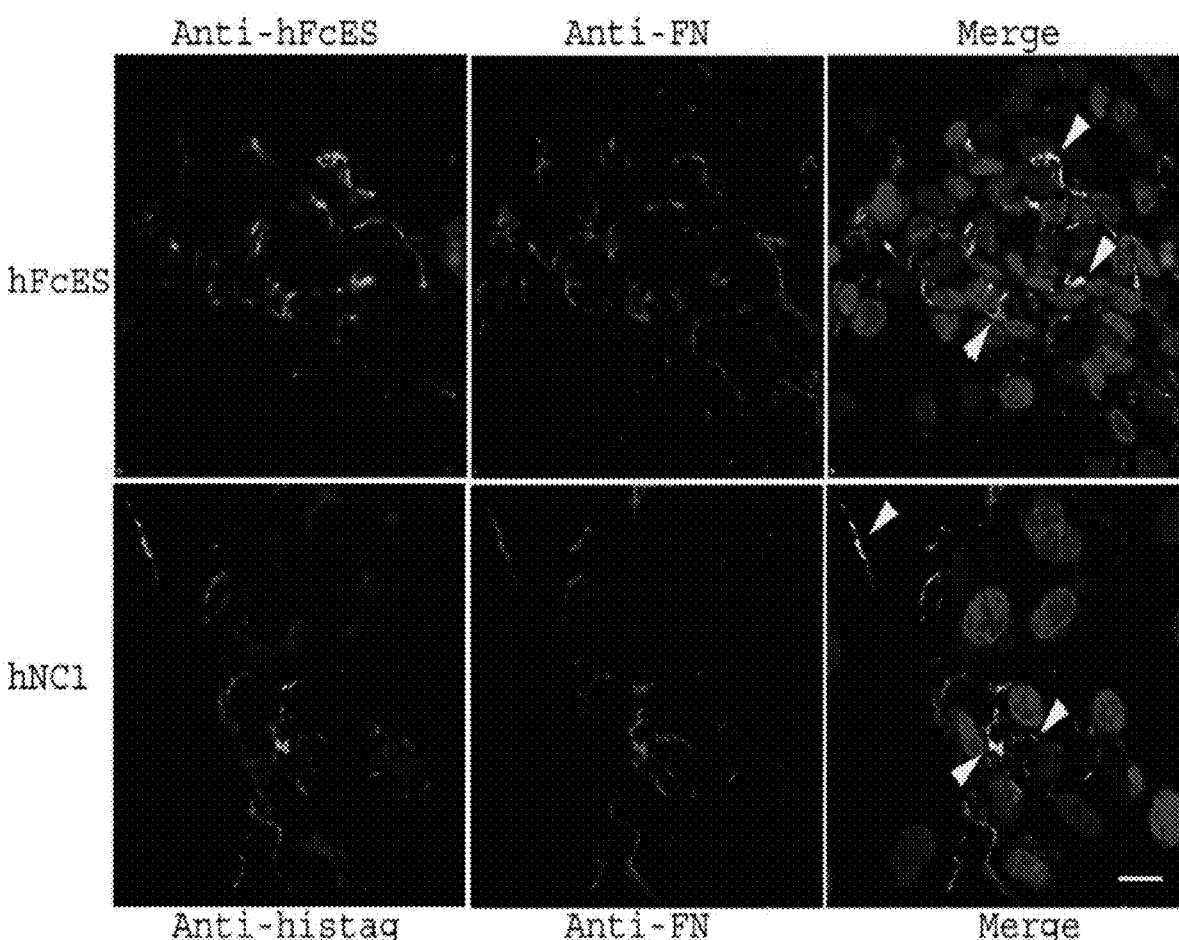
Figure 3B:
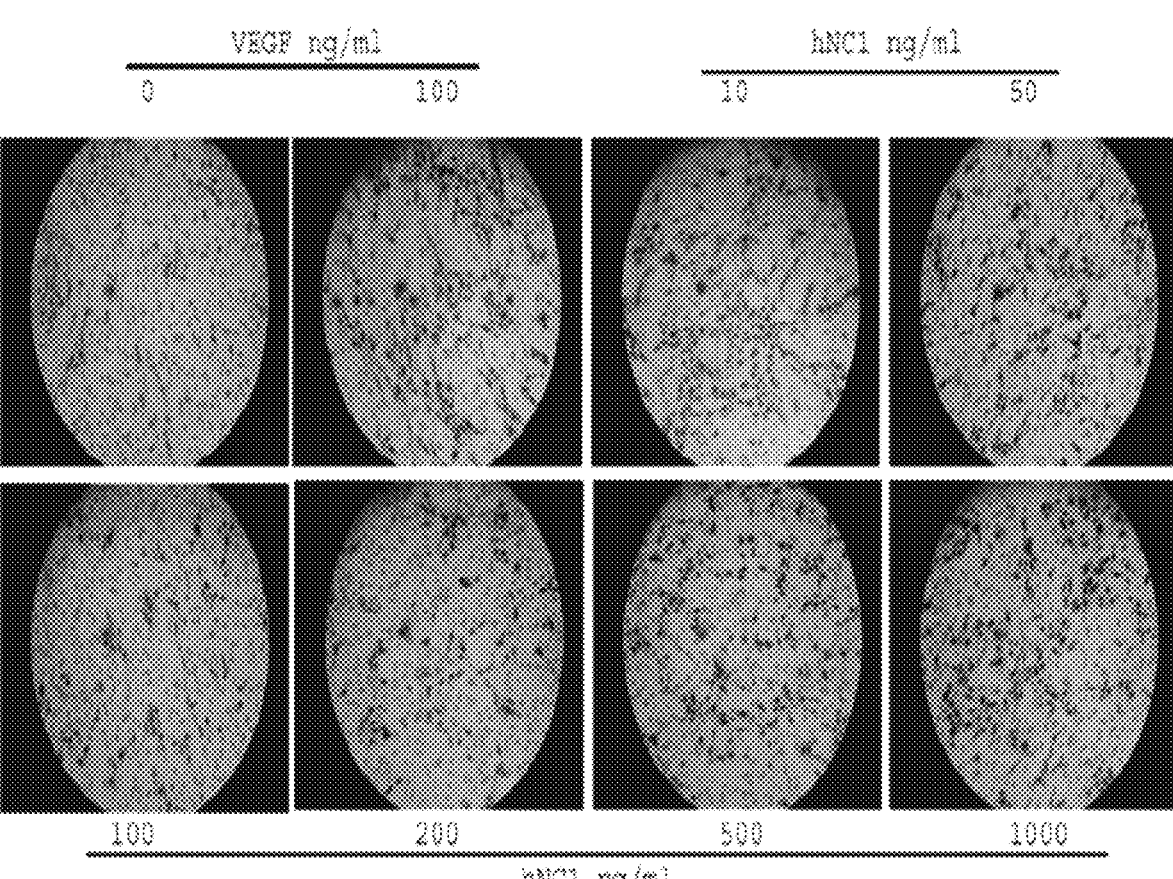
Figure 3B:
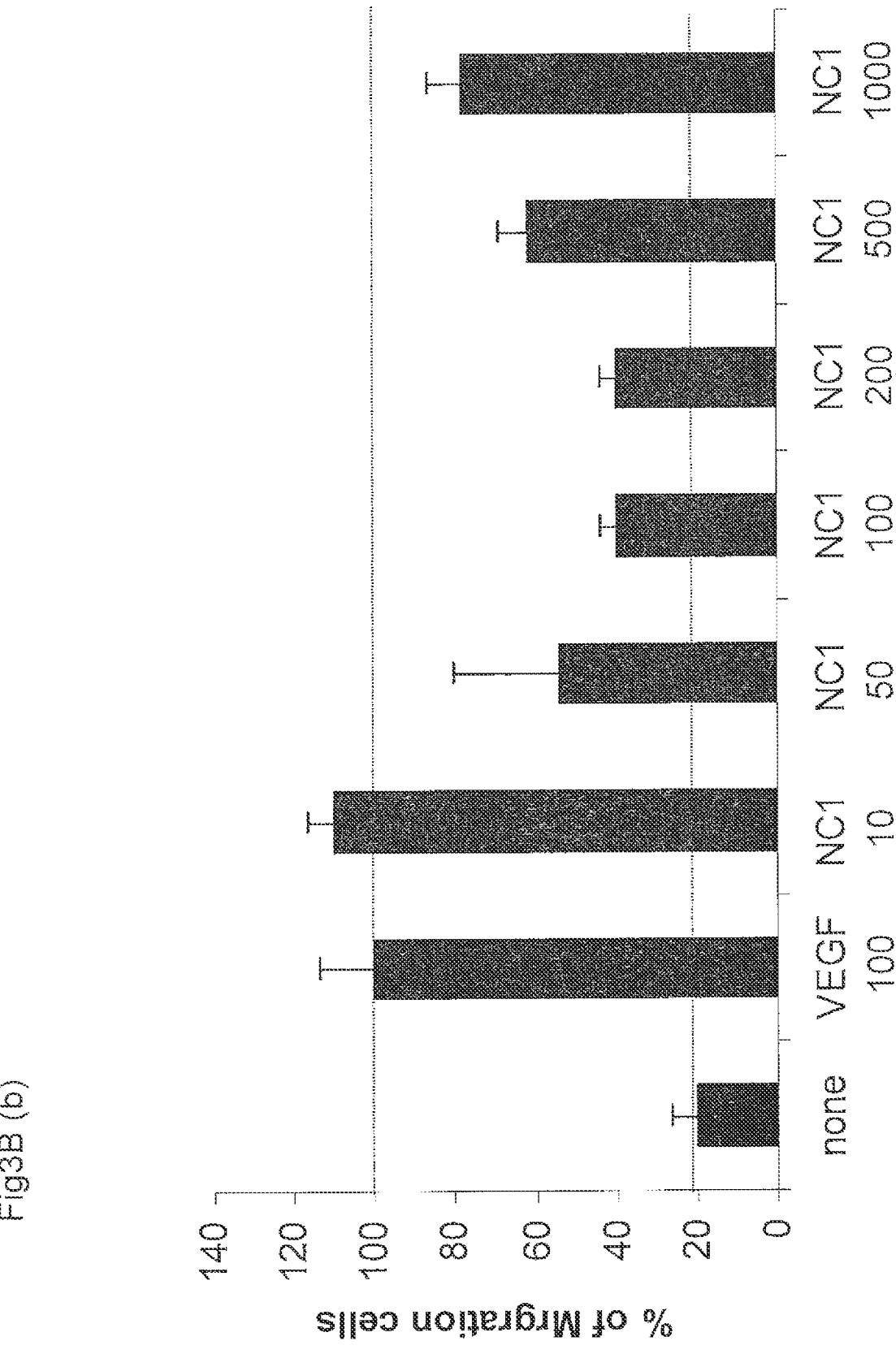
Figure 3B:
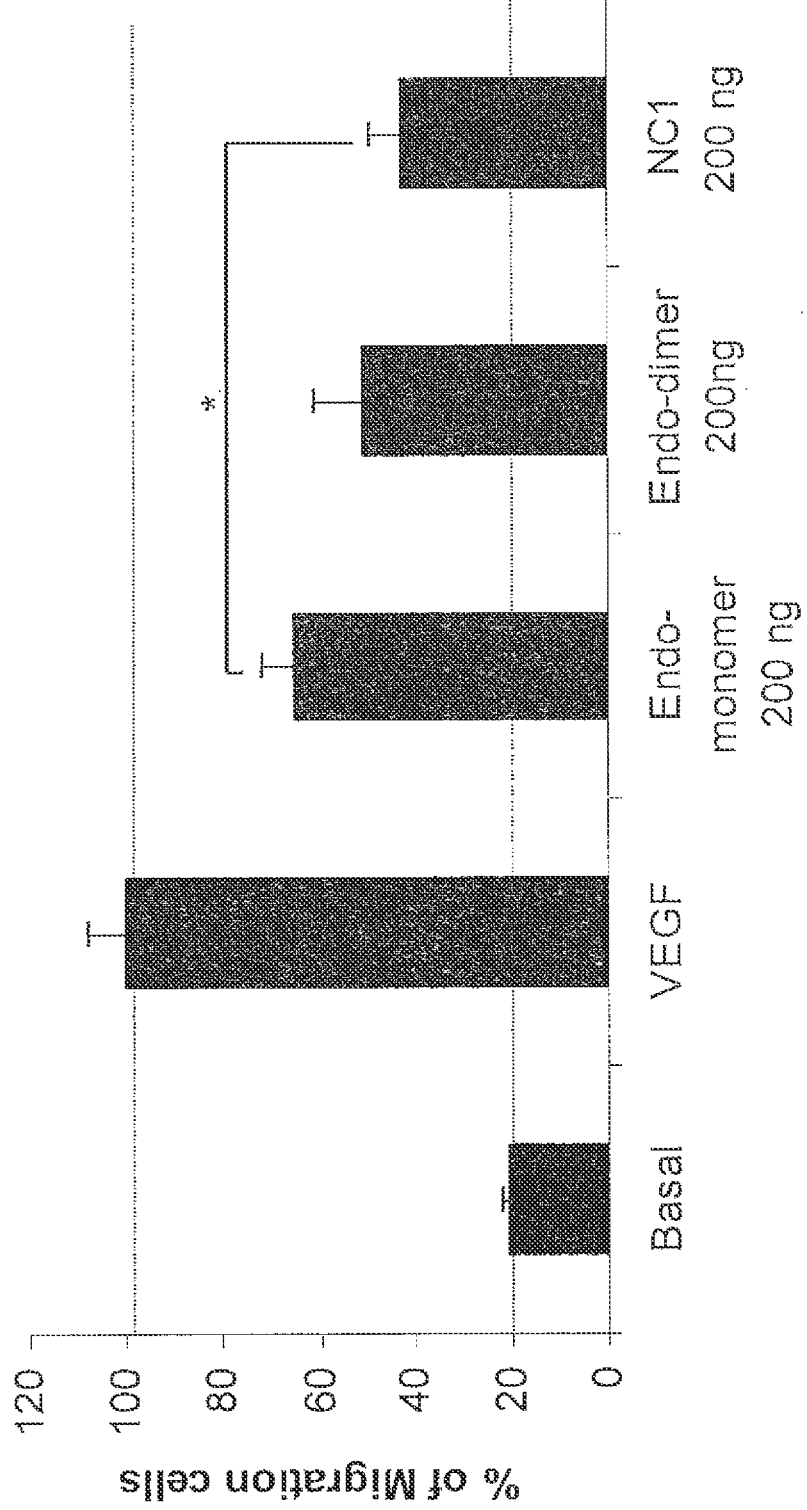

2.3 Binding of oligomeric hFc-endostatin and hNC-1 to HUVECs. Immunoflourescence technique was employed to detect endothelial cell surface binding of oligomeric endostatin and NC-1. Fc-endostatin and NC-1 showed a poor binding to HUVECS when the cells were cultured only for 24 hours (data not shown). Prolonging incubation time to 72 hours resulted in significant binding, possibly, as a consequence of fibronectin upregulation (FIG. 3A upper panel). These data suggest a critical role for fibronectin as mediator of dimeric endostatin binding to endothelial cells. 3D image showed the distributions of endostatin and fibronectin on endothelial cells.

2.4 hNC-1 inhibits endothelial cells migration. Endothelial cell migration is an important step in new blood vessel formation and tumor angiogenesis. To evaluate the effect of hNC-1 on endothelial cell migration, rhVEGF has been used to induce HUVECs migration in a transwell assay. The migration of cells has been monitored and quantified Cells migrating across the membrane were stained with blue-purple stain (FIG. 3B(*a*)) and counted. The hNC-1 inhibited VEGF-induced endothelial cell migration as a function of concentration and the dose effect followed a U-shaped curve (FIG. 3B(b)) (Lee et al., loc. cit.). NC-1 was the most potent anti-migratory agent among different endostatin molecules tested (FIG. 3B(c)).

2.5 Absence of Endostatin in human circulation. Endostatin was initially isolated from condition media of a mouse tumor cell line (EOMA). Purification of the proteins involved a number of steps. Identification of its N-terminus sequence resulted in an endostatin molecule starting at the N-terminus sequence "HTH". Both recombinant mouse and human endostatins were constructed on the basis of this N-terminus sequence (O'Reilly et al. 1997, *Cell* 88, 277).

The size of endostatin in the sera of several individuals has been investigated. To this end, a half-liter bag of PRP (platelet rich plasma) collected 4 days earlier from 1-4 individuals was obtained. Following a low RPM centrifugation to remove platelets, a high RPM was applied to obtain the serum. The serum was passed through Protein A to remove IgGs. It was then subjected to immunoprecipitation by an endostatin polyclonal antibody followed by Western analysis. A monoclonal antibody directed to endostatin was used for treating the membrane (FIG. 4). The protein markers are NC-1 and endostatin. The size of identified protein is between the two markers with several protein bands present (FIG. 4A). An identical procedure was applied to a serum from a different individual (FIG. 4B) To confirm these data, following Protein A step, affinity purification of an earlier PRP sample (different from the referred PRP bag) yielded similar size molecules (FIG. 4C). Finally, immunoprecipitation of the platelets by the same polyclonal antibody showed that the identified protein is a larger size molecule than endostatin (FIG. 4D).

These results prompted the inventors to reanalyze the earlier data with endostatin (O'Reilly et al., loc. cit). The earliest condition media employed for endostatin isolation was continuously kept at 4° C. for a long period of time (at least a month) prior to final purification step. Presence of fetal calf serum in the media can cause degradation of NC-1. Confirmation of this hypothesis was established by another group in the inventor's laboratory a year later, employing the same mouse tumor cell line (Wen et al., loc. cit.). Upon shortening the duration of protein isolation and employing a single step of purification, the major proteins were found to be mNC-1 and endostatin (Wen et al., loc. cit.). Consequently, the earlier observation of an endostatin size protein being the only product following HPLC purification, strongly supports the inventor's hypothesis that NC-1 was completely digested to an endostatin size molecule after prolonged incubation at 4° C. Additional evidence for this hypothesis comes from published data by a different group of investigators (Sasaki et al 1998, *EMBO* J 17, 4249).

Most probably, the first reported endostatin was a result of degradation taking place in the laboratory. NC-1 is the precursor of endostatin. The data of the inventors on human sera were based on the experiments performed days after collection and purification and the inventors could not avoid digestion of NC-1 to smaller fragments. The inventors conclude from these data that in contrast to mouse EOMA, 187 amino acid endostatin is absent in human serum and platelet. Some of these larger than endostatin degradation products of NC-1 may correspond to dimers which are possible candidates to be present in human circulation or results of NC-1 post collection degradation. Consequently, the present data strongly suggest that NC-1 is the most physiologically relevant molecule in human circulation.

2.6 hNC-1 suppresses tumor growth in vivo. In order to compare anti-tumor activities of NC-1 and endostatin, nude mice bearing human melanoma cell line A2058 were employed. The data are shown in FIG. 5. Two doses of clinical grade endostatin differing by 5-fold in concentration of protein (low and high doses) were used. A corresponding low dose of NC-1 showed anti-tumor activity similar to high dose of endostatin. The results demonstrate a better anti-tumor efficacy by NC-1 compared with endostatin. It cannot be ruled out the possibility that injected NC-1 becomes degraded upon entering the circulation.

2.7 Generation and Expression of a mFc-NC-1 Fusion Protein.

A murine Fc-NC-1 fusion construct comprising the non-triple helical trimerization domain (association domain), the hinge region and the endostatin domain (comprising the zinc binding site) of the NC-1 domain of mouse collagen 18 shown in SEQ ID NO: 3 has been generated and expressed in 293 kidney cells. In this construct, the Fc domain shown in SEQ ID NO: 5 is located at the N-terminus and the murine NC-1 domain (shown in SEQ ID NO. 3) at the C-terminus of said fusion protein. In addition, a linker carrying an enterokinase cleavage site has been interposed between Fc and NC-1, in order to allow for cleaving the fusion construct. It is evident to those skilled in the art that a corresponding therapeutic product for administering in patients will not have such a cleavage site. FIG. 7 shows the picture of an SDS gel of said murine Fc-NC-1 fusion construct as a function of the amount of plasmid used in transfection of 293 kidney cells under reduced and non-reduced conditions. Under reduced conditions, the product is a single chain consisting of Fc and NC-1. Under non-reduced conditions, the product is a dimer because Fc is disulfide bonded. Dimeric Fc can accommodate only two chains of NC-1 by covalent linkage. It is therefore presumed that the third chain of NC-1 which is non-covalently associated gets dissociated in the presence of SDS and, thus, is in loading sample and the gel itself. The single band in the middle of the gel is due to the endostatin marker which has a molecular weight of 20 Kd. Subsequently, said construct will be tested for anti-tumor activity and longer half-life of this protein.

2.8 Acquired Drug Resistance to Endogenous Angiogenesis Inhibitors: Endostatin

Murine Lewis Lung Carcinoma (LLC) tumors were implanted s.c. into C57/B16 mice. Tumors were treated with a murine oligomeric-NC1 fragment, mFc-endostatin, at doses indicated. LLC tumors were exposed in-vivo for a prolonged period to mFc-endostatin by sequential transplantation of tumors (up to four passages, p4) once they evade therapy and reach a size of approximately 1000-2000 mm³. Control tumors were also sequentially transplanted into new mice without mFc-endostatin treatment. Tumor volume was measured by caliper measurement (FIG. 8). After four passages, both mFc-endostatin resistant as well as control tumors were excised, total RNA was isolated and after QC hybridized on genome-wide microarrays for transcriptional analysis. Microarray data were analyzed using SUMO software package. Quantitative real-time RT-PCR was performed using Taqman technology to confirm the expression of candidate genes identified by microarray analysis.

As a result, this data shows that, in contrast to previous reports, the inventors were able to generate tumors resistant to mFc-endostatin that mimics the NC-1 effect described elsewhere herein. These tumors were generated by sequential implantation and treatment of tumors, in murine lung cancer (LLC) and human pancreatic adenocarcinoma (BxPC3) up to 4 passages. Genome-wide expression profiling revealed down regulation of fibronectin rendering tumors resistant to mFc-endostatin treatment (FIG. 9). This is in line with the inventor's observation of selective binding of oligomeric mFc-endostatin and oligomeric NC-1 to fibronectin. Therefore, analysis of fibronectin levels can be used as a prognostic marker for cancer therapy response.

Further, the inventors identified a number of compensatory pathways being activated rendering tumors resistant to Fc-endostatin therapy, in particular sequential treatment with IGF1R inhibitors seems promising, according to preliminary animal data, and CCL2 seems to constitute another promising candidate target.

2.9 Novel hybrid peptides "Superstatins" with anti-tumor activity

In the previous examples, the inventors hypothesized and provided evidence that the physiological substrate of Collagen 18 in human circulation consists of oligomers of the endostatin domain (ED) from the non-collagenous NC-1 region of collagen 18. Further, they confirmed that synthetic ED-dimer built based on fusion of endostatin to human immunoglobin Fc-region (Fc-Endostatin) binds Fibronectin (FN), whereas the monomer does not. High affinity binding of FN to VEGF was further confirmed. Taken together, the inventors proposed that oligomeric NC-1 may elicit their effects via FN binding via interference with at least two pivotal angiogenesis pathways, i.e., VEGF and integrin alpha 5 beta 1 (ITGA5B1) signaling. Moreover, they found that FN is significantly down-regulated in tumors that become resistant to oligomeric NC-1 (Fc-Endostatin) after prolonged exposure, i.e. four serial in-vivo passages. Therefore, they postulated that loss of FN might constitute a key mechanism of inherent and acquired resistance to oligomeric NC-1 substrates.

The inventors followed two strategies to provide an ultimate proof of this concept.

The first approach was to engineer a minimal peptide sequence that would mimic the key effects of the ED-FN complex. Towards this goal, the inventors selected the most active motif in the entire ED-domain consisting of a 27 amino acid-NH2-terminal region that was originally identified by Dr. Javaherian, one of the present inventors (Tjin Tham Sjin et al. 2005, Cancer Res. 65, 3656-63). Preliminary data by the present inventors indicate that this region itself may be capable of binding to VEGF and that the two histidines (Zinc binding domain) in this peptide sequence may be critical for VEGF binding. This is conceivable, because a mutated peptide in which Histidines were replaced by Alanine residues failed to compete with VEGF-ED-dimer (Fc-Endostatin) binding. On the other hand, fibronectin contains two active motifs that are critical for its binding to ITGA5B1, i.e. a PHSRN-(SEQ ID NO:20) and a RGD-dependent motif. FIG. 10 shows a schematic overview of critical motifs within the ED-domain and FN.

In order to mimic the physiological complex of oligomeric NC-1 and FN that mediated integrin signaling and other properties of the NC-1-ED, the inventors aimed to fuse these two critical motifs, i.e. the above-mentioned most active motif in the NC-1-ED domain and the integrin-binding motif of fibronectin comprising "RGD" and surrounding amino acids, and generated a hybrid peptide called Superstatin. For each peptide sequence, a human and mouse equivalent was designed, as described in more detail in Example 2.10.

In the following, data in a syngeneic murine lung cancer model (LLC) are presented using the murine Superstatin sequence:

(SEQ ID NO: 7)
HTHQDFQPVLHLVLYAVTGRGDSPASSK
NC1-ED Motif-FN-Motif hybrid

To proof that the effects are not mediated by the FN-Motif per se, a reference peptide was employed lacking the NC1-ED mimetic motif, i.e. consisting only of the FN-Motif:

(SEQ ID NO: 8)

LYAVTGRGDSPASSK.

Additional constructs containing the PHSRN (SEQ ID NO:20) instead of the RGD motif of FN, as well as constructs facilitating dimerization of the Superstatin peptide via disulfide bounds or Fc regions are currently in preparation or already under in-vivo evaluation; see Example 2.10.

Using the protypic LLC murine (C57BL6) lung cancer model, the inventors were able to show the efficacy of the murine Superstatin peptide to potently inhibit tumor growth.

As shown in FIG. 11, wild type LLC tumors (10.000 cells) were implanted s.c. in C57B16 mice. Tumors were sham treated (PBS), with the reference FN-mimetic-peptide containing only the "LYAVTGRGDSPASSK" sequence (SEQ ID NO: 8; FN motif) or with murine Superstatin (SEQ ID NO: 7) at the dose of 50 µg peptide in 100 µl PBS every 12 h s.c. (n: 5 in each group). Treatment was started 4 days after tumor implantation ("prevention trial") and continued for 24 days. Of note, during the treatment period only a single tumor grew in the Superstatin group. Two additional tumors appeared only after cessation of Superstatin therapy indicating that these hard-to-treat tumors were controlled by this therapy. Tumor size reaching 1000 mm$^2$ was considered as death event in the Kaplan-Meier analysis. Superstatin significantly prolonged survival (p<0.03 by log-rank test) as compared to control. In contrast, the FN-Motif alone (SEQ ID NO: 8) showed no significant improvement in prevention of tumor growth.

Once the efficacy of the Superstatin peptide (SEQ ID NO: 7) was confirmed, the inventors moved toward the second strategy to validate the proposed concept that FN signaling is critical for oligomeric NC-1 to exert their anti-angiogenic and anti-tumoral effects. Using a lentiviral shRNA construct against murine Fibronectin, they down-regulated FN in LLCs mimiking the natural phenotype of previously generated p4 Fc-Endostatin resistant tumors. LLC FN −/− tumor cells (100.000) were implanted in C57B16 mice and treatment with dimeric murine Fc-Endostatin vs. Superstatin was started on day 4 post implantation. Knockdown of FN rendered LLC tumors resistant to oligomeric NC-1 (Fc-Endostatin). Moreover, in analogy to the originally reported data on naturally selected p4 resistant LLC tumor cells, LLC FN−/− tumor showed a trend towards faster growth, as compared to control. In contrast, the Superstatin peptide containing both the ED-motif and the FN-motif (SEQ ID NO: 7) significantly inhibited tumor growth, as compared to control or Fc-Endostatin treated tumors (p<0.01); see FIG. 12. These data show that Superstatin activity is independent of FN availability in tumors, hence circumventing the resistance mechanism that renders tumors resistant to oligomeric NC-1.

Based on the findings in the previous examples, the inventors proposed that compensatory up-regulation of pro-tumorigenic and pro-angiogenic pathways identified might constitute a promising target to circumvent acquired tumor resistance to ED derived agents or oligomeric NC-1. Inhibition of two particular pathways, i.e. IGF1R signaling and CCL2 was proposed to be most promising due to availability of pharmacological agents already entering advanced clinical trial stages. Here, the inventors show that sequential but not concurrent administration of an IGF1R inhibitor impaired the growth of tumors that are resistant to murine Fc-Endostatin (NC-1-ED-Dimer); see FIG. 13.

Protein analysis by Western blot further confirmed enhanced IGF1R expression and phosphorylation, down-regulation of Fibronectin and up-regulation of CCL2 as the function of therapy with murine Fc-Endostatin (Endo) in passage 5 LLC tumors; see FIG. 14. Sequential treatment with IGF1R inhibitor partially reversed this phenotype.

Example 2.10: Designed Peptides

Previous data by the present inventors has demonstrated that the active motif of NC-1-ED resides in the N-terminus of the protein and can be mimicked by a 25 amino acid peptide. SEQ ID NO: 9 shows the corresponding murine sequence, whereas SEQ ID NO: 10 shows the corresponding human sequence. Furthermore, in view of the fact that the zinc binding coordinates of ED are mediated by three histidines in this peptide, the inventors have shown previously that substitution of histidines by alanines resulted in a peptide which was inactive in inhibiting tumor growth, angiogenesis and vessel permeability (Tjin Tham Sjin et al., Cancer Res. 2005, 65, 3656-63).

SEQ ID NO: 11 (murine) and SEQ ID NO: 12 (human) show the sequences of the "RGD" motif and surrounding amino acids in Fibronectin important for binding to integrin alpha 5 beta 1. In addition, the "PHSRN" motif (SEQ ID NO:20) in the integrin binding domain of Fibronectin has been found to be critical for binding of Fibronectin to ITGA5B1 (integrin alpha 5 beta 1).

Based on preliminary data by the inventors that oligomeric endostatin (NC-1) binds Fibronectin, they have generated a series of peptides which combine motifs of the mentioned endostatin N-terminal peptide with an RGD containing domain of Fibronectin:

SEQ ID NO: 7 shows the corresponding murine Superstatin sequence, whereas SEQ ID NO: 13 shows the corresponding human Superstatin sequence, i.e. the hybrid peptide sequences of the present invention.

In order to examine the importance of the Zinc-binding region of endostatin in relation to the antitumor properties of the hybrid peptide, the inventors have modified the human Superstatin (SEQ ID NO: 13) by replacing the critical histidines at positions 1 and 3 by alanines (SEQ ID NO: 14).

To test for relevance of dimerization properties of the hybrid peptides to antitumor activity, the inventors have employed an earlier reported method of endostatin dimerization (Kuo et al., 2001, JCB 152, 1233-46). By replacing glutamine at position 7 in the human Superstatin sequence (SEQ ID NO: 13) by cysteine, the hybrid peptide should form a dimer and can be tested for activity in tumor-bearing mice (SEQ ID NO: 15).

As a control for RGD binding of fibronectin to the integrin, "RGD" in the human Superstatin sequence (SEQ ID NO: 13) has been changed to "RAD", in a new hybrid peptide (SEQ ID NO: 16) to evaluate its antitumor activity, in comparison with the wild-type peptide.

Presented are the human versions of these modified peptides (denoted by "h"). The mouse versions are similar sequences (denoted by "m") and can be derived based on the sequence information provided herein.

Additional larger control peptides are currently designed containing 25 amino acids of integrin binding regions of fibronectin (SEQ ID NO: 17) to be evaluated in antitumor studies.

Finally, the human Superstatin peptide (SEQ ID NO: 13) is conjugated to the complexing agent 1,4,7,10-tetraazacyclododecane-1,4,7,10-tetraacetic acid (also known as DOTA) providing the ability to conjugate the peptide with, e.g., radionuclides such as Gallium ($^{68}$Ga) for non-invasive imaging (Positron emission tomography, PET). The inventors check currently if DOTA conjugation is affecting the efficacy of the human Superstatin peptide in-vivo in a BxPC3 human pancreatic cancer model. In case this experiment confirms the activity of the Superstatin-DOTA constructs, in-vivo PET-Imaging evaluating the potential of Superstatin-DOTA as diagnostic agent is envisioned.

The corresponding sequences of the above-indicated peptides are shown in the following Table 1:

| mP1 | HTHQDFQPVLHLVALNTPLSGGMRGI | (SEQ ID NO: 9) |
|---|---|---|
| hp1 | HSHRDFQPVLHLVALNSPLSGGMRG | (SEQ ID NO: 10) |
| mPint | LYAVTGRGDSPASSK | (SEQ ID NO: 11) |
| hPint | VYAVTGRGDSPASSK | (SEQ ID NO: 12) |
| mSUPERSTATIN | HTHQDFQPVLHLVLYAVTGRGDSPASSK | (SEQ ID NO: 7) |
| hSUPERSTATIN | HSHRDFQPVLHLVYAVTGRGDSPASSK | (SEQ ID NO: 13) |
| hPint. Endo (two H at N-terminus to A) | ASARDFQPVLHLVYAVTGRGDSPASSK | (SEQ ID NO: 14) |
| hPint. Endo (Q7 to C) | HSHRDFCPVLHLVYAVTGRGDSPASSK | (SEQ ID NO: 15) |
| hPin. Endo (G to A) | HSHRDFQPVLHLVYAVTGRADSPASSK | (SEQ ID NO: 16) |
| mPint-L | IKPGADYTITLYAVTGRGDSPASSK | (SEQ ID NO: 17) |
| Human Superstatin-DOTA | DOTA-HSHRDFQPVLHLVYAVTGRGDSPASSK-CONH2 | (SEQ ID NO: 13) |

3. Discussion

In these examples, the inventors have presented strong evidence that the molecular size of endostatin reported in literature is likely a product of protease degradation following collection of mouse cell culture media or human serum. Evidence presented by Sasaki and collaborators (loc. cit) appear to support this hypothesis. Their analysis of a human serum following two purification steps resulted in a number of endostatin-like molecules in terms of their sizes. All three reported molecules had additional amino acids at the N-termini, pointing to absence of an endostatin molecule starting with the reported histidine at the N-terminus Amino acid sequence analysis of higher molecular weight bands was not reported. Furthermore, the authors' investigation of collagen 18 distribution in different organs of mice indicated absence of endostatin size molecules in different tissue extracts (Sasaki et al., loc. cit.). The most prominent identified protein corresponded to NC-1.

The inventors have identified fibronectin as a binding protein for oligomeric endostatin (Fc-endostatin and artificial endostatin dimer) and not endostatin monomer. NC-1 and endostatin dimer have been shown previously to bind a number of ECM proteins, a property not shared by endostatin monomer (Sasaki et al., loc. cit.; Javaherian et al. 2002, *J Biol Chem* 277, 45211). However, fibronectin has distinct properties which make it unique among ECM proteins. Angiostatic peptides use plasma fibronectin to home to angiogenic vasculature (Yi et al. 2003, PNAS 100, 11435).

Fibronectin contains the sequence of amino acids RGD which allows the protein to bind to a number of integrins. Integrin α5β1 is a receptor on the cell surface which binds fibronectin. This integrin is an important mediator of angiogenesis (Hynes, loc. cit.).

Endostatin binding to two integrins αvβ3 and α5β1 was first reported in 2001 (Rehn et al. 2001, PNAS 98, 1024). Presumably, such a binding inhibits interactions of fibronectin with these integrins. Later, another group of investigators presented data indicating that endostatin only binds α5β1 (Wickstrom et al. 2002, *Cancer Res* 62, 5580). Endostatin lacks the sequence RGD. Consequently, such a binding must be mediated by other amino acids on endostatin. The present inventors have attempted to demonstrate direct binding of endostatin to α5β1 employing Elisa, immunoprecipitation and cell adhesion assays without success.

The data of the inventors point to the importance of oligomeric endostatin and NC-1 (Lee et al., loc. cit.). Starting with NC-1 trimer precursor, NC-1 is converted into a dimer following a size reduction as a result of degradation. Finally, endostatin monomer is formed upon further size reduction. The data of the inventors lend support to the hypothesis that hNC-1 and possibly dimers of molecules larger than endostatin are present in circulation. Existence of endostatin size monomer in circulation is questionable. It has been shown previously that the physiological termination of the angiogenesis process by endostatin is well coordinated (Abdollahi et al. 2004, *Mol Cell* 13, 649).

In order to incorporate the data presented here, the inventors suggest a model where fibronectin serves as template (FIG. 6) Both VEGF and NC-1 bind fibronectin. Presence of VEGF and NC-1 modulate the biological activity via interactions with integrin α5β1. The interplay of a pro-angiogenic protein (VEGF) and an anti-angiogenic protein (NC-1) may be crucial for regulating angiogenesis at the surface of the cell.

The inventor's utilization of Fc-endostatin (a dimer) has clearly demonstrated that it is far superior to ordinary endostatin (monomer) (Lee et al., loc. cit.). A much smaller dose of Fc-endostatin is required to achieve the same tumor reduction in comparison with endostatin alone (50-100 fold)

In the past, the inventors have attributed this difference to longer half-life associated with any Fc conjugated molecules. The present data of the inventors suggest that the dimeric state of endostatin in Fc-endostatin may also contribute to exhibiting better efficacy. On the other hand, following injection of NC-1 into mice, it may undergo a rapid degradation and this may account for lack of a dramatic increase in its anti-tumor effects, in comparison with endostatin. In that case, a fusion construct of NC-1 linked to a Fc domain of an immunoglobulin may turn out to be an improved reagent for anti-cancer treatment among different type of endostatin. Experiments of this type are currently in progress, see Example 2.7.

Together, these data indicate that FN is critical for anti-angiogenic and anti-tumor action of collagen 18 fragments. Superstatin, a hybrid peptide containing the critical FN motif and ED-motif was able to potently inhibit/prevent tumor growth and to reverse the resistant phenotype conferred by tumor specific down-regulation of Fibronectin. Alternatively, rational design of combination therapies and development of innovative scheduling schemes aiming to target compensatory pathways activated in Fc-Endostatin resistant tumors could pose a promising strategy to circumvent- or reverse, inherent or acquired tumor resistance.

```
                         SEQUENCE LISTING

Sequence total quantity: 20
SEQ ID NO: 1               moltype = AA   length = 1527
FEATURE                    Location/Qualifiers
source                     1..1527
                           mol_type = protein
                           organism = Mus musculus
SEQUENCE: 1
MAPDPSRRLC LLLLLLLSCR LVPASADGNS LSPLNPLVWL WPPKTSDSLE GPVSKPQNSS  60
PVQSTENPTT HVVPQDGLTE QQTTPASSEL PPEEEEEEDQ KAGQGGSPAT PAVPIPLVAP  120
AASPDMKEEN VAGVGAKILN VAQGIRSFVQ LWDEDSTIGH SAGTEVPDSS IPTVLPSPAE  180
LSSAPQGSKT TLWLSSAIPS SPDAQTTEAG TLAVPTQLPP FQSNLQAPLG RPSAPPDFPE  240
NVAEEVGLLQ LLGDPLPEKI SQIDDPHVGP AYIFGPDSNS GQVAQYHFPK LFFRDFSLLF  300
HVRPATEAAG VLFAITDAAQ VVVSLGVKLS EVRDGQQNIS LLYTEPGASQ TQTGASFRLP  360
AFVGQWTHFA LSVDGGSVAL YVDCEEFQRV PFARASQGLE LERGAGLFVG QAGTADPDKF  420
QGMISELKVR KTPRVSPVHC LDEEDDDEDR ASGDFGSGFE ESSKSHKEDT SLLPGLPQPP  480
PVTSPPLAGG STTEDPRTEE TEEDAAVDSI GAETLPGTGS SGAWDEAIQN PGRGLIKGGM  540
KGQKGEPGAQ GPPGPAGPQG PAGPVVQSPN SQPVPGAQGP PGPQGPPGKD GTPGRDGEPG  600
DPGEDGRPGD TGPQGFPGTP GDVGPKGEKG DPGIGPRGPP GPPGPPGPSF RQDKLTFIDM  660
EGSGFSGDIE SLRGPRGFPG PPGPPGVPGL PGEPGRFGIN GSYAPGPAGL PGVPGKEGPP  720
GFPGPPGPPG PPGKEGPPGV AGQKGSVGDV GIPGPKGSKG DLGPIGMPGK SGLAGSPGPV  780
GPPGPPGPPG PPGPGFAAGF DDMEGSGIPL WTTARSSDGL QGPPGSPGLK GDPGVAGLPG  840
AKGEVGADGA QGIPGPPGRE GAAGSPGPKG EKGMPGEKGN PGKDGVGRPG LPGPPGPPGP  900
VIYVSSEDKA IVSTPGPEGK PGYAGFPGPA GPKGDLGSKG EQGLPGPKGE KGEPGTIFSP  960
DGRALGHPQK GAKGEPGFRG PPGPYGRPGH KGEIGFPGRP GRPGTNGLKG EKGEPGDASL  1020
GFSMRGLPGP PGPPGPPGPP GMPIYDSNAF VESGRPGLPG QQGVQGPSGP KGDKGEVGPP  1080
GPPGQFPIDL FHLEAEMKGD KGDRGDAGQK GERGEPGAPG GGFFSSSVPG PPGPGYPGI  1140
PGPKGESIRG PPGPPGPQGP PGIGYEGRQG PPGPPGPPGP PSFPGPHRQT VSVPGPPGPP  1200
GPPGPPGAMG ASAGQVRIWA TYQTMLDKIR EVPEGWLIFV AEREELYVRV RNGFRKVLLE  1260
ARTALPRGTG NEVAALQPPL VQLHEGSPYT RREYSYSTAR PWRADDILAN PPRLPDRQPY  1320
PGVPHHHSSY VHLPPARPTL SLAHTHQDFQ PVLHLVALNT PLSGGMRGIR GADFQCFQQA  1380
RAVGLSGTFR AFLSSRLQDL YSIVRRADRG SVPIVNLKDE VLSPSWDSLF SGSQGQLQPG  1440
ARIFSFDGRD VLRHPAWPQK SVWHGSDPSG RRLMESYCET WRTETTGATG QASSLLSGRL  1500
LEQKAASCHN SYIVLCIENS FMTSFSK                                     1527

SEQ ID NO: 2               moltype = AA   length = 1516
FEATURE                    Location/Qualifiers
source                     1..1516
                           mol_type = protein
                           organism = Homo sapiens
SEQUENCE: 2
MAPYPCGCHI LLLLFCCLAA ARANLLNLNW LWFNNEDTSH AATTIPEPQG PLPVQPTADT  60
TTHVTPRNGS TEPATAPGSP EPPSELLEDG QDTPTSAESP DAPEENIAGV GAEILNVAKG  120
IRSFVQLWND TVPTESLARA ETLVLETPVG PLALAGPSST PQENGTTLWP SRGIPSSPGA  180
HTTEAGTLPA PTPSPPSLGR PWAPLTGPSV PPPSSERISE EVGLLQLLGD PPPQQVTQTD  240
DPDVGLAYVF GPDANSGQVA RYHFPSLFFR DFSLLFHIRP ATEGPGVLFA ITDSAQAMVL  300
LGVKLSGVQD GHQDISLLYT EPGAGQTHTA ASFRLPAFVG QWTHLALSVA GGFVALYVDC  360
EEFQRMPLAR SSRGLELEPG AGLFVAQAGG ADPDKFQGVI AELKVRRDPQ VSPMHCLDEE  420
GDDSDGASGD SGSGLGDARE LLREETGAAL KPRLPAPPPV TTPPLAGGSS TEDSRSEEVE  480
EQTTVASLGA QTLPGSDSVS TWDGSVRTPG GRVKEGGLKG QKGEPGVPGP PGRAGPPGSP  540
CLPGPPGLPC PVSPLGPAGP ALQTVPGPQG PPGPPGRDGT PGRDGEPGDP GEDGKPGDTG  600
PQGFPGTPGD VGPKGDKGDP GVGERGPPGP QGPPGPPGPS FRHDKLTFID MEGSGFGGDL  660
EALRGPRGFP GPPGPPGVPG LPGEPGRFGV NSSDVPGPAG LPGVPGREGP PGFPGLPGPP  720
GPPGREGPPG RTGQKGSLGE AGAPGHKGSK GAPGPAGARG ESGLAGAPGP AGPPGPPGPP  780
GPPGPGLPAG FDDMEGSGGP FWSTARSADG PQGPPGLPGL KGDPGVPGLP GAKGEVGADG  840
VPGFPGLPGR EGIAGPQGPK GDRGSRGEKG DPGKDGVGQP GLPGPPGPPG PVVYVSEQDG  900
SVLSVPGPEG RPGFAGFPGP AGPKGNLGSK GERGSPGPKG EKGEPGSIFS PDGGALGPAQ  960
KGAKGEPGFR GPPGPYGRPG YKGEIGFPGR PGRPGMNGLK GEKGEPGDAS LGFGMRGMPG  1020
PPGPPGPPGP PGTPVYDSNV FAESSRPGPP GLPGNQGPPG PKGAKGEVGP PGPPGQFPFD  1080
FLQLEAEMKG EKGDRGDAGQ KGERGEPGGG GFFGSSLPGP PGPPGPRGYP GIPGPKGESI  1140
RGQPGPPGPQ GPPGIGYEGR QGPPGPPGPP GPPSFPGPHR QTISVPGPPG PPGPPGPPGT  1200
MGASSGVRLW ATRQAMLGQV HEVPEGWLIF VAEQEELYVR VQNGFRKVQL EARTPLPRGT  1260
```

```
DNEVAALQPP VVQLHDSNPY PRREHPHPTA RPWRADDILA SPPRLPEPQP YPGAPHHSSY    1320
VHLRPARPTS PPAHSHRDFQ PVLHLVALNS PLSGGMRGIR GADFQCFQQA RAVGLAGTFR    1380
AFLSSRLQDL YSIVRRADRA AVPIVNLKDE LLFPSWEALF SGSEGPLKPG ARIFSFDGKD    1440
VLRHPTWPQK SVWHGSDPNG RRLTESYCET WRTEAPSATG QASSLLGGRL LGQSAASCHH    1500
AYIVLCIENS FMTASK                                                   1516

SEQ ID NO: 3              moltype = AA   length = 315
FEATURE                   Location/Qualifiers
source                    1..315
                          mol_type = protein
                          organism = Mus musculus
SEQUENCE: 3
AGQVRIWATY QTMLDKIREV PEGWLIFVAE REELYVRVRN GFRKVLLEAR TALPRGTGNE    60
VAALQPPLVQ LHEGSPYTRR EYSYSTARPW RADDILANPP RLPDRQPYPG VPHHHSSYVH    120
LPPARPTLSL AHTHQDFQPV LHLVALNTPL SGGMRGIRGA DFQCFQQARA VGLSGTFRAF    180
LSSRLQDLYS IVRRADRGSV PIVNLKDEVL SPSWDSLFSG SQGQLQPGAR IFSFDGRDVL    240
RHPAWPQKSV WHGSDPSGRR LMESYCETWR TETTGATGQA SSLLSGRLLE QKAASCHNSY    300
IVLCIENSFM TSFSK                                                    315

SEQ ID NO: 4              moltype = AA   length = 312
FEATURE                   Location/Qualifiers
source                    1..312
                          mol_type = protein
                          organism = Homo sapiens
SEQUENCE: 4
SGVRLWATRQ AMLGQVHEVP EGWLIFVAEQ EELYVRVQNG FRKVQLEART PLPRGTDNEV    60
AALQPPVVQL HDSNPYPRRE HPHPTARPWR ADDILASPPR LPEPQPYPGA PHHSSYVHLR    120
PARPTSPPAH SHRDFQPVLH LVALNSPLSG GMRGIRGADF QCFQQARAVG LAGTFRAFLS    180
SRLQDLYSIV RRADRAAVPI VNLKDELLFP SWEALFSGSE GPLKPGARIF SFDGKDVLRH    240
PTWPQKSVWH GSDPNGRRLT ESYCETWRTE APSATGQASS LLGGRLLGQS AASCHHAYIV    300
LCIENSFMTA SK                                                       312

SEQ ID NO: 5              moltype = AA   length = 233
FEATURE                   Location/Qualifiers
source                    1..233
                          mol_type = protein
                          organism = Mus musculus
SEQUENCE: 5
EPRGPTIKPC PPCKCPAPNL LGGPSVFIFP PKIKDVLMIS LSPIVTCVVV DVSEDDPDVQ    60
ISWFVNNVEV HTAQTQTHRE DYNSTLRVVS ALPIQHQDWM SGKEFKCKVN NKDLPAPIER    120
TISKPKGSVR APQVYVLPPP EEEMTKKQVT LTCMVTDFMP EDIYVEWTNN GKTELNYKNT    180
EPVLDSDGSY FMYSKLRVEK KNWVERNSYS CSVVHEGLHN HHTTKSFSRT PGK           233

SEQ ID NO: 6              moltype = AA   length = 232
FEATURE                   Location/Qualifiers
source                    1..232
                          mol_type = protein
                          organism = Homo sapiens
SEQUENCE: 6
EPKSSDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT    120
ISKAKGQPRE PQVYTLPPSR EEMTKNQVSL TCLVKGFYPS DIAVEWESNG QPENNYKTTP    180
PVLDSDGSFF LYSKLTVDKS RWQQGNVFSC SVMHEALHNH YTQKSLSLSP GK           232

SEQ ID NO: 7              moltype = AA   length = 28
FEATURE                   Location/Qualifiers
source                    1..28
                          mol_type = protein
                          organism = Mus musculus
SEQUENCE: 7
HTHQDFQPVL HLVLYAVTGR GDSPASSK                                       28

SEQ ID NO: 8              moltype = AA   length = 15
FEATURE                   Location/Qualifiers
source                    1..15
                          mol_type = protein
                          organism = Mus musculus
SEQUENCE: 8
LYAVTGRGDS PASSK                                                    15

SEQ ID NO: 9              moltype = AA   length = 26
FEATURE                   Location/Qualifiers
source                    1..26
                          mol_type = protein
                          organism = Mus musculus
SEQUENCE: 9
HTHQDFQPVL HLVALNTPLS GGMRGI                                        26

SEQ ID NO: 10             moltype = AA   length = 25
```

-continued

```
FEATURE               Location/Qualifiers
source                1..25
                      mol_type = protein
                      organism = Homo sapiens
SEQUENCE: 10
HSHRDFQPVL HLVALNSPLS GGMRG                                          25

SEQ ID NO: 11         moltype = AA  length = 15
FEATURE               Location/Qualifiers
source                1..15
                      mol_type = protein
                      organism = Mus musculus
SEQUENCE: 11
LYAVTGRGDS PASSK                                                     15

SEQ ID NO: 12         moltype = AA  length = 15
FEATURE               Location/Qualifiers
source                1..15
                      mol_type = protein
                      organism = Homo sapiens
SEQUENCE: 12
VYAVTGRGDS PASSK                                                     15

SEQ ID NO: 13         moltype = AA  length = 27
FEATURE               Location/Qualifiers
source                1..27
                      mol_type = protein
                      organism = Homo sapiens
SEQUENCE: 13
HSHRDFQPVL HLVYAVTGRG DSPASSK                                        27

SEQ ID NO: 14         moltype = AA  length = 27
FEATURE               Location/Qualifiers
source                1..27
                      mol_type = protein
                      organism = Homo sapiens
SEQUENCE: 14
ASARDFQPVL HLVYAVTGRG DSPASSK                                        27

SEQ ID NO: 15         moltype = AA  length = 27
FEATURE               Location/Qualifiers
source                1..27
                      mol_type = protein
                      organism = Homo sapiens
SEQUENCE: 15
HSHRDFCPVL HLVYAVTGRG DSPASSK                                        27

SEQ ID NO: 16         moltype = AA  length = 27
FEATURE               Location/Qualifiers
source                1..27
                      mol_type = protein
                      organism = Homo sapiens
SEQUENCE: 16
HSHRDFQPVL HLVYAVTGRA DSPASSK                                        27

SEQ ID NO: 17         moltype = AA  length = 25
FEATURE               Location/Qualifiers
source                1..25
                      mol_type = protein
                      organism = Mus musculus
SEQUENCE: 17
IKPGADYTIT LYAVTGRGDS PASSK                                          25

SEQ ID NO: 18         moltype = AA  length = 27
FEATURE               Location/Qualifiers
source                1..27
                      mol_type = protein
                      note = mP1
                      organism = synthetic construct
SEQUENCE: 18
HTHQDFQPVL HLVALNTPLS GGMRGIR                                        27

SEQ ID NO: 19         moltype = AA  length = 27
FEATURE               Location/Qualifiers
source                1..27
                      mol_type = protein
                      note = mP1-H1/3A
                      organism = synthetic construct
SEQUENCE: 19
```

-continued

```
ATAQDFQPVL HLVALNTPLS GGMRGIR                                    27

SEQ ID NO: 20            moltype = AA   length = 5
FEATURE                  Location/Qualifiers
source                   1..5
                         mol_type = protein
                         organism = synthetic construct
SEQUENCE: 20
PHSRN                                                            5
```

What is claimed is:

1. A peptide comprising an amino acid sequence shown in SEQ ID NO. 7 or 13.

2. The peptide of claim 1, further comprising an Fc domain of an immunoglobulin.

3. The peptide of claim 1, wherein the amino acid sequence is shown in SEQ ID NO. 7.

4. The peptide of claim 1, wherein the amino acid sequence is shown in SEQ ID NO. 13.

* * * * *